(12) United States Patent  
Leif et al.

(10) Patent No.: US 8,916,692 B2
(45) Date of Patent: Dec. 23, 2014

(54) REAGENT SYSTEM AND METHOD FOR MODIFYING THE LUMINESCENCE OF LANTHANIDE(III) MACROCYCLIC COMPLEXES

(76) Inventors: Robert C. Leif, San Diego, CA (US); Sean Yang, San Diego, CA (US); Lidia Vallarino, Richmond, VA (US)

( * ) Notice: Subject to any disclaimer, the term of this patent is extended or adjusted under 35 U.S.C. 154(b) by 1016 days.

(21) Appl. No.: 10/578,355

(22) PCT Filed: Nov. 8, 2004

(86) PCT No.: PCT/US2004/037314
§ 371 (c)(1),
(2), (4) Date: Jun. 12, 2006

(87) PCT Pub. No.: WO2005/046735
PCT Pub. Date: May 26, 2005

(65) Prior Publication Data
US 2007/0134160 A1  Jun. 14, 2007

Related U.S. Application Data

(60) Provisional application No. 60/518,605, filed on Nov. 7, 2003.

(51) Int. Cl.
*C07F 5/00* (2006.01)
*G01N 21/64* (2006.01)
*G01N 33/533* (2006.01)
*A61B 5/00* (2006.01)

(52) U.S. Cl.
CPC .......... *G01N 33/533* (2013.01); *G01N 21/6428* (2013.01); *G01N 2021/6441* (2013.01)
USPC ........................................... 534/15; 600/317

(58) Field of Classification Search
USPC ............................................................ 534/15
See application file for complete search history.

(56) References Cited

U.S. PATENT DOCUMENTS

| | | | | |
|---|---|---|---|---|
| 4,927,923 A | * | 5/1990 | Mathis et al. | 540/456 |
| 5,316,909 A | * | 5/1994 | Xu | 435/6 |
| 5,373,093 A | * | 12/1994 | Vallarino et al. | 534/15 |
| 5,696,240 A | * | 12/1997 | Vallarino et al. | 534/15 |
| 6,340,744 B1 | | 1/2002 | Leif et al. | |
| 6,750,005 B2 | * | 6/2004 | Leif et al. | 435/4 |

* cited by examiner

*Primary Examiner* — Michael G Hartley
*Assistant Examiner* — Melissa Perreira
(74) *Attorney, Agent, or Firm* — R. Scott Kimsey, Esq.; Klein DeNatale Goldner

(57) ABSTRACT

Disclosed is a spectrofluorimetrically detectable luminescent composition consisting essentially of at least one energy transfer acceptor lanthanide(III) complex having an emission spectrum maximum in the range from 300 to 2000 nanometers and a luminescence-enhancing amount of at least one energy transfer donor selected from the group consisting of a fluorophore, a lumiphore, an organic compound, a salt of an organic ion, a metal ion, a metal ion complex, or a combination thereof. Such energy transfer donor enhances the luminescence of at least one energy transfer acceptor lanthanide (III) complex, with the conditions that the emission spectrum of any energy transfer donor differs from that of its energy transfer acceptor lanthanide(III) complex; and such energy transfer donor can be dissolved to form a unitary solution in a solvent having an evaporation rate at least as great as that of water.

16 Claims, 16 Drawing Sheets

Figure 1 shows inverted images of the wells of a microtiter plate.

| EuMac | | | Abbreviation | % EtOH | % H₂O | Integrated Luminescence |
|---|---|---|---|---|---|---|
| − | + | | | | | |
|  |  | A | TTFA-25EtOH | 25 | 75 | 10,667 |
|  |  | B | TTFA-50EtOH | 50 | 50 | 8,881 |
|  |  | C | TTFA-75EtOH | 75 | 25 | 7,306 |
|  |  | D | TTFA-100EtOH | 100 | 0 | 596 |
|  |  | E | Gd(III)-TTFA-25EtOH | 25 | 75 | 27,526 |
|  |  | F | Gd(III)-TTFA-50EtOH | 50 | 50 | 31,258 |
|  |  | G | Gd(III)-TTFA-75EtOH | 75 | 25 | 27,534 |
|  |  | H | Gd(III)-TTFA-100EtOH | 100 | 0 | 11,943 |
|  |  | I | Gd(TTFA)$_3$-28EtOH | 28 | 72 | 24,409 |
|  |  | J | Gd(TTFA)$_3$-58EtOH | 58 | 42 | 33,409 |
|  |  | K | Gd(TTFA)$_3$-75EtOH | 75 | 25 | 32,588 |
|  |  | L | Gd(TTFA)$_3$-100EtOH | 100 | 0 | 31,055 |
|  |  | M | TTFA 1.45 mM EtOH | | | *Old solution |
|  |  | N | Gd(TTFA)$_3$ 1.2 mM EtOH | | | *Old solution |
|  |  | O | LEL Emulsion | | | 36,497 |
|  |  | P | LEL Emulsion | | | 36,845 |

Figure 2 shows inverted images of the wells of a microtiter plate.

*These solutions had been kept at room temperature, which resulted in their producing questionable results.

| EuMac | Well | Abbreviation | Material | Solvent | Mean EuMac -Mean Neg. Cntrl. |
|---|---|---|---|---|---|
| - + | | | | | |
| ■ | A | LEL emulsion | LEL emulsion | $H_2O$ | 190 |
| | B | Gd(III)-$H_2O$ | Gd(III) | $H_2O$ | 7.6 |
| | C | Gd(III)-MeOH | Gd(III) | MeOH | 0.6 |
| | D | Gd(III)-Isopropanol | Gd(III) | Isopropanol | 1.3 |
| | E | TTFA-$H_2O$ | TTFA | $H_2O$ | 14.8 |
| | F | TTFA-MeOH | TTFA | MeOH | 16.8 |
| | G | TTFA-Isopropanol | TTFA | Isopropanol | 11.7 |
| □ | H | Gd(III)-TTFA-$H_2O$ | Gd(III) + TTFA | $H_2O$ | 91 |
| ■ | I | Gd(III)-TTFA-MeOH | Gd(III) + TTFA | MeOH | 126 |
| | J | Gd(III)-TTFA-Isopropanol | Gd(III) + TTFA | Isopropanol | 8.5 |
| □ | K | Gd(TTFA)$_3$-$H_2O$ | Gd(TTFA)$_3$ | $H_2O$ | 67 |
| ■ | L | Gd(TTFA)$_3$-MeOH | Gd(TTFA)$_3$ | MeOH | 152 |
| | M | Gd(TTFA)$_3$-Isopropanol | Gd(TTFA)$_3$ | Isopropanol | 25 |

Figure 3 shows inverted images of the wells of a microtiter plate.

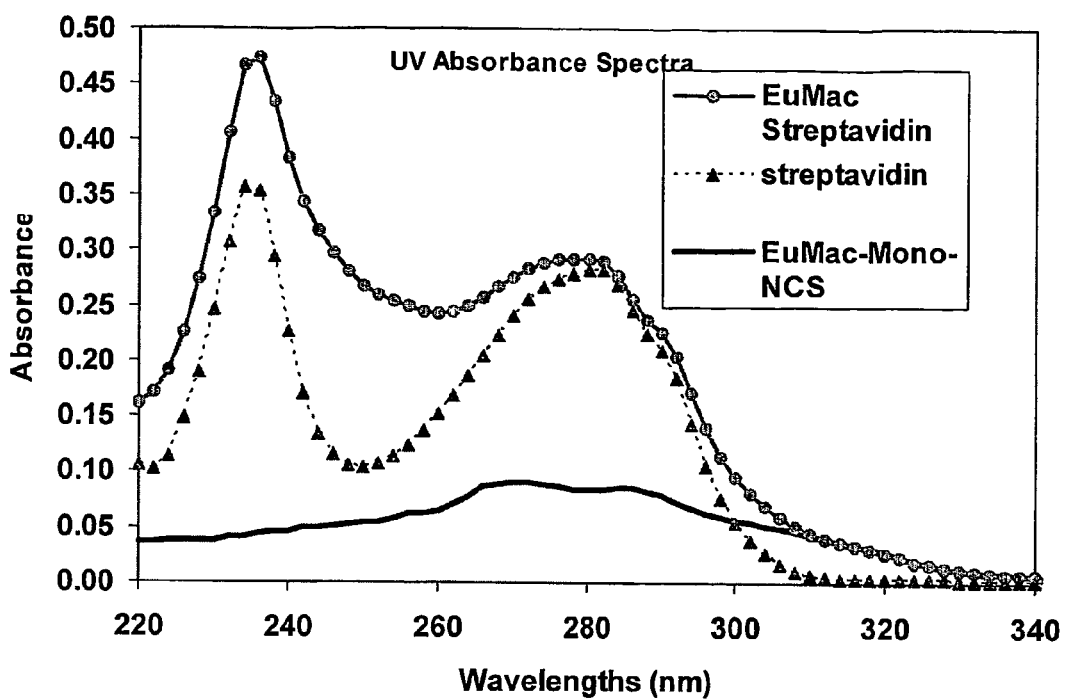
Figure 4 is a graphical presentation of the ultraviolet absorption spectra of the EuMac-mono-NCS, the EuMac coupled to streptavidin, and streptavidin.

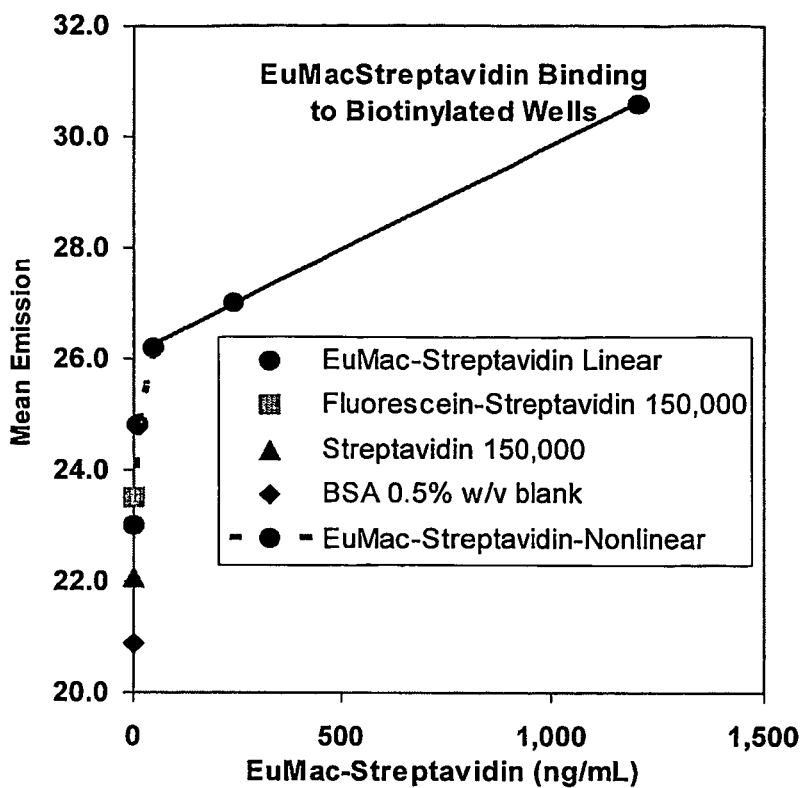
Figure 5 is a graph of the relative emission intensity versus the concentration of streptavidin added to the biotinylated well.

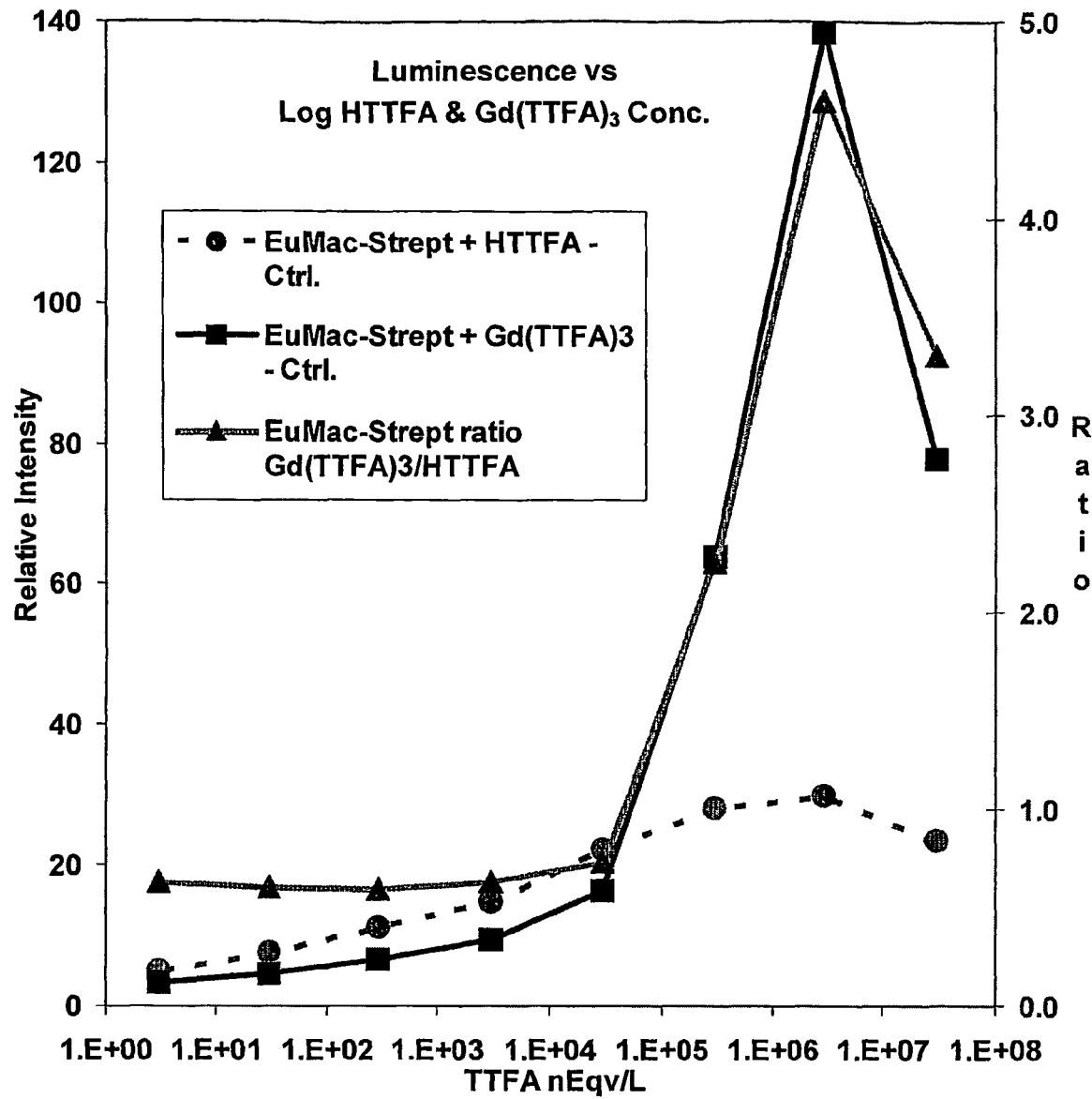
Figure 6 is a plot the concentrations of Gd(TTFA)$_3$ and HTTFA vs. relative luminescence.

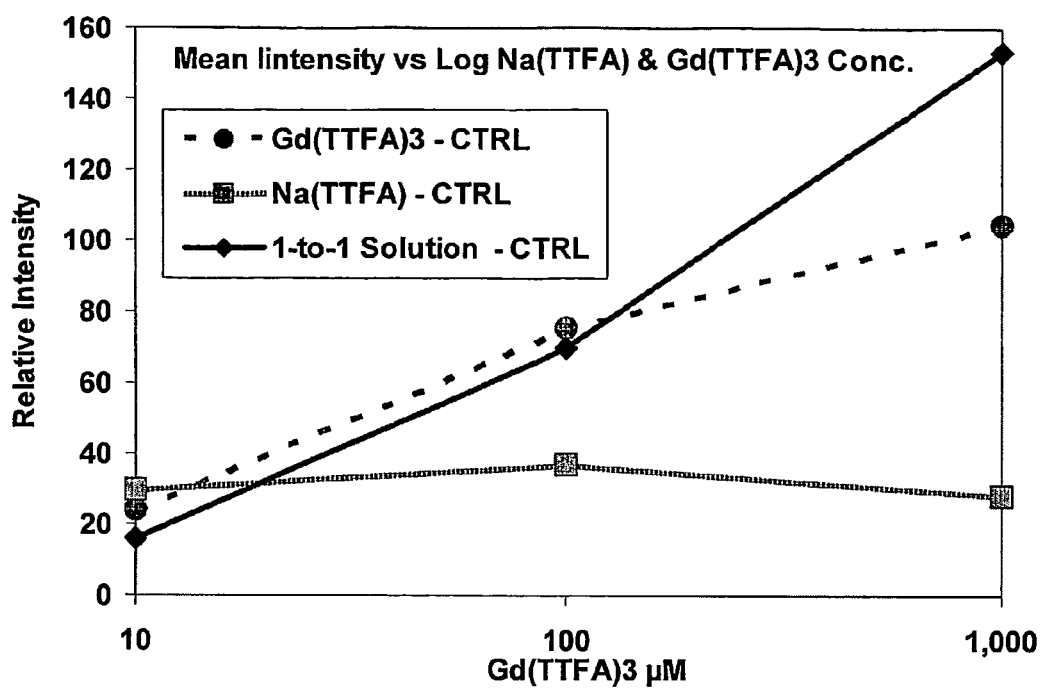
Figure 7 is a plot of the concentrations of Gd(TTFA)$_3$, Na(TTFA), and their one-to-one mixture vs. relative luminescence.

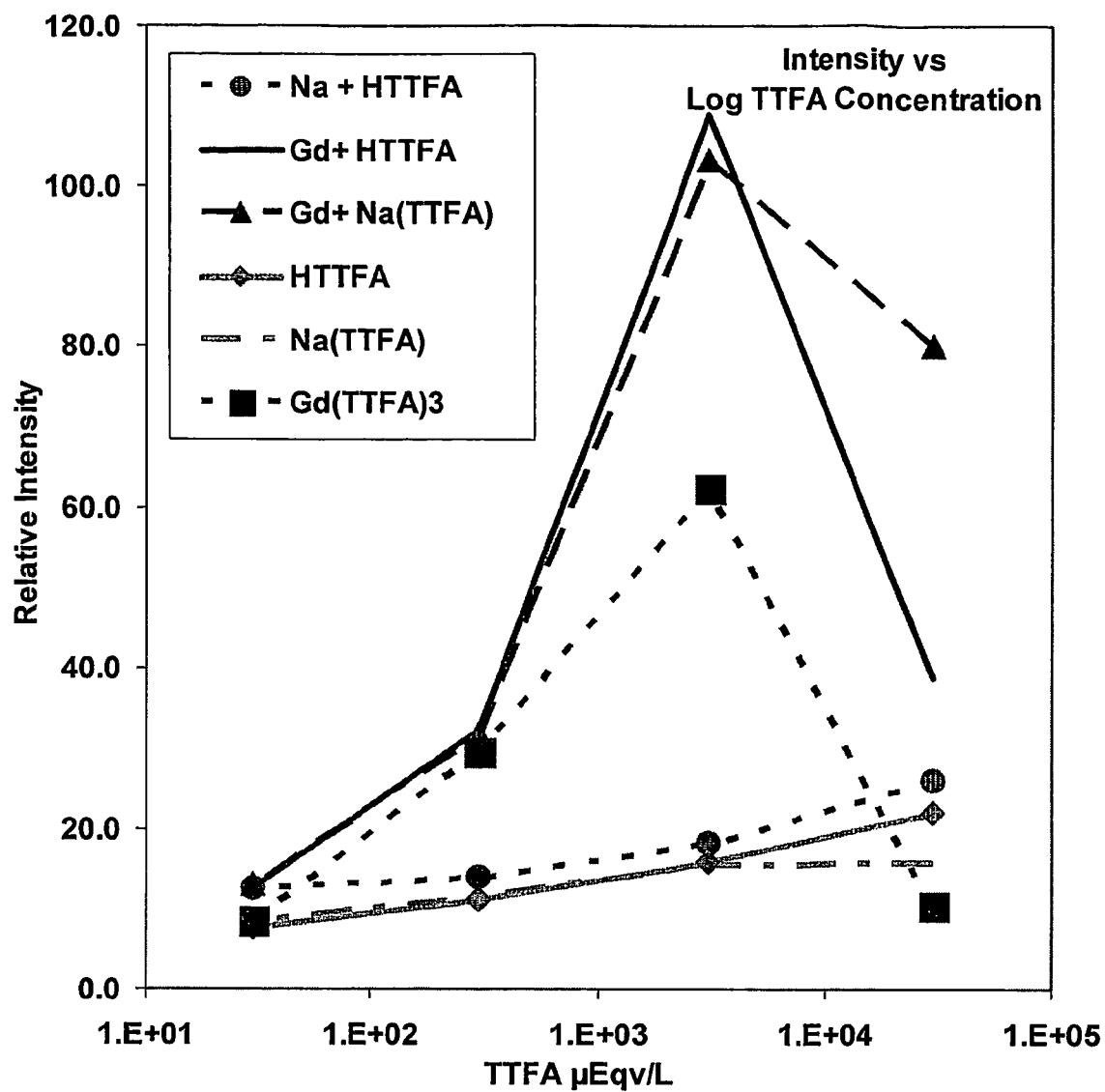
Figure 8 is a plot of the concentrations of $Gd(TTFA)_3$, $Na(TTFA)$, HTTFA, and their mixtures vs. relative luminescence.

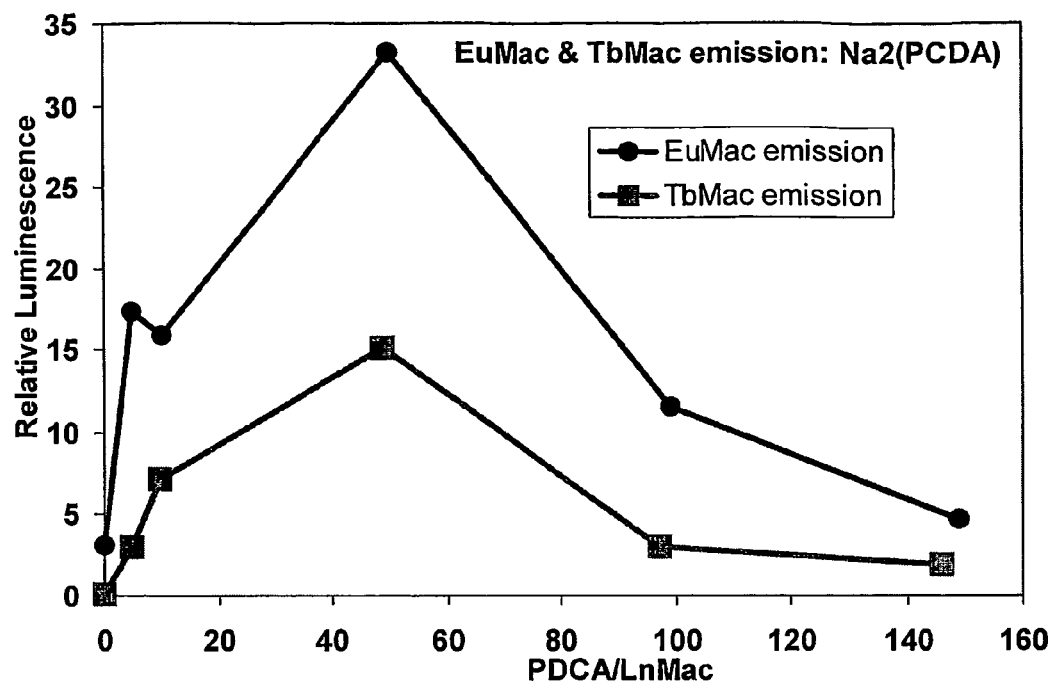
Figure 9a is a graph showing the effect of differing concentrations of $Na_2(PDCA)$ on the luminescence of two different lanthanide macrocycles..

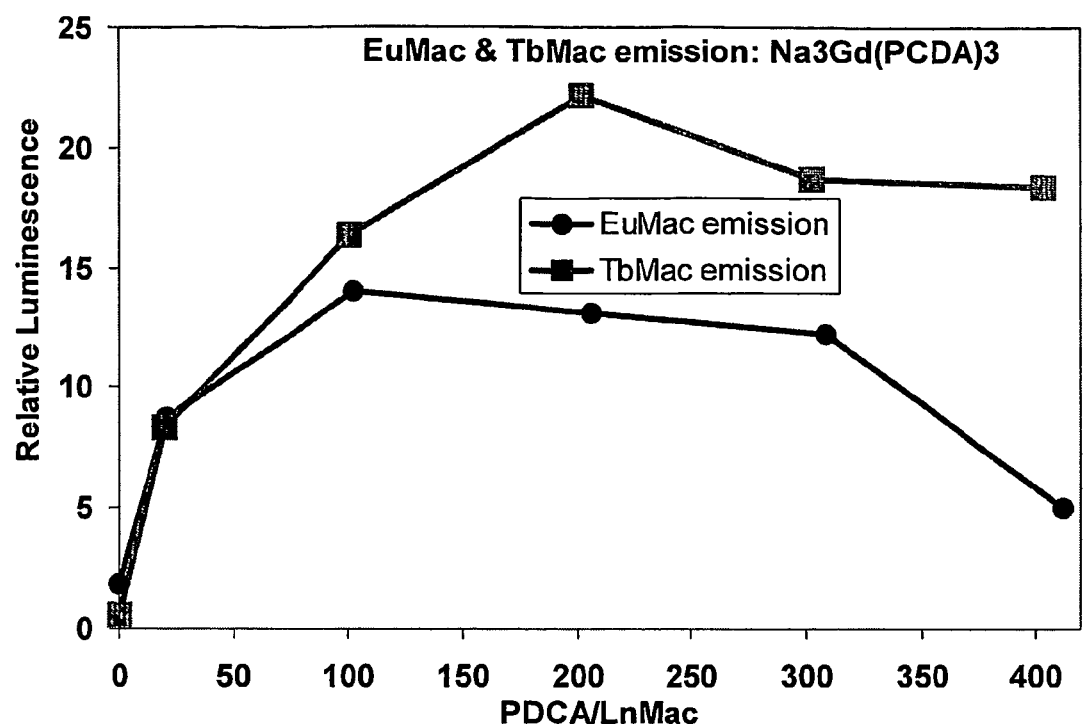
Figure 9b is a graph showing the effect of differing concentrations of $Na_3Gd(PCDA)_3$ on the luminescence of two different lanthanide macrocycles.

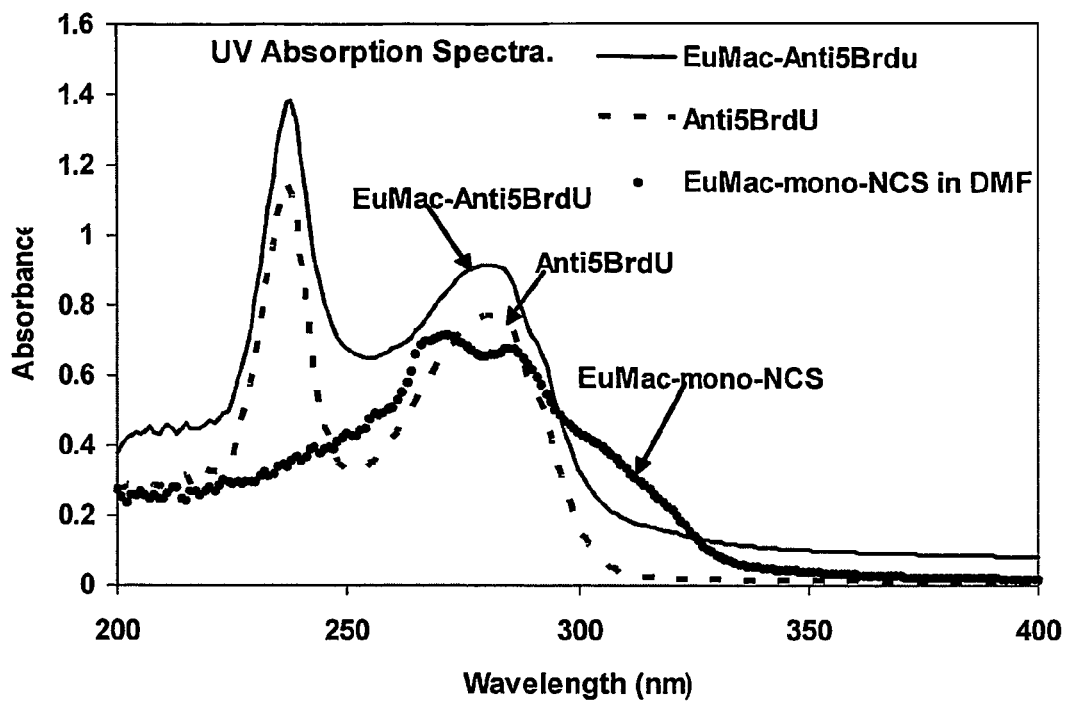
Figure 10 is a graphical presentation of the ultraviolet absorption spectra of the EuMac-mono-NCS, the EuMac coupled to anti-5-BrdU, and anti-5-BrdU.
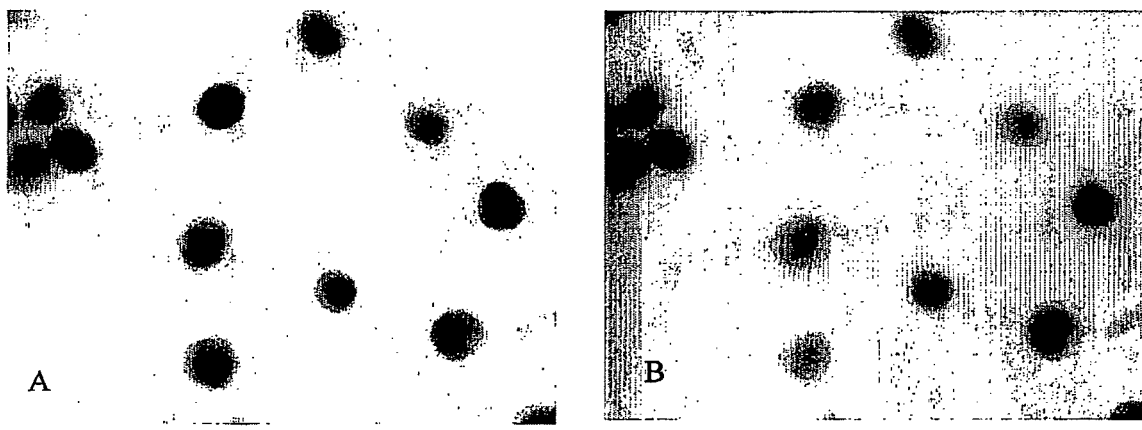
Figure 11 is a pair of inverted images of EuMac-di-NCS stained cells. A is a 5 second exposure; B is the summation of 1000 time-gated images, each exposed for 2 msec.

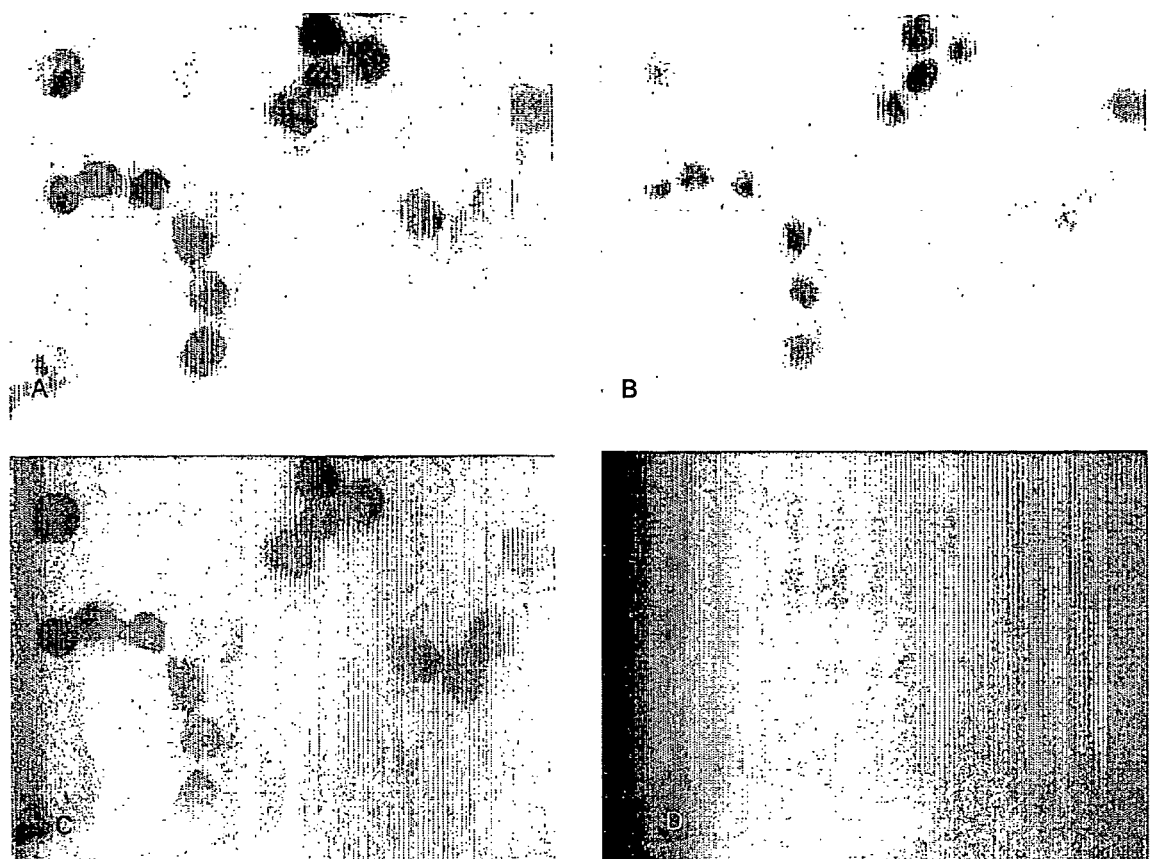
Figure 12 shows four images of a single preparation of nonapoptotic cells stained with both EuMac and DAPI.
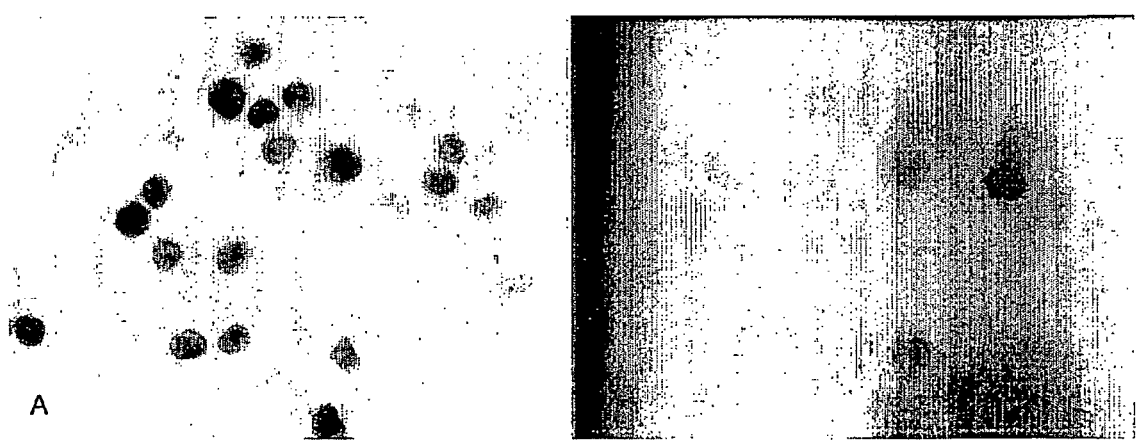
Figure 13 shows two inverted images of cells stained with SmMac-di-NCS and DAPI.

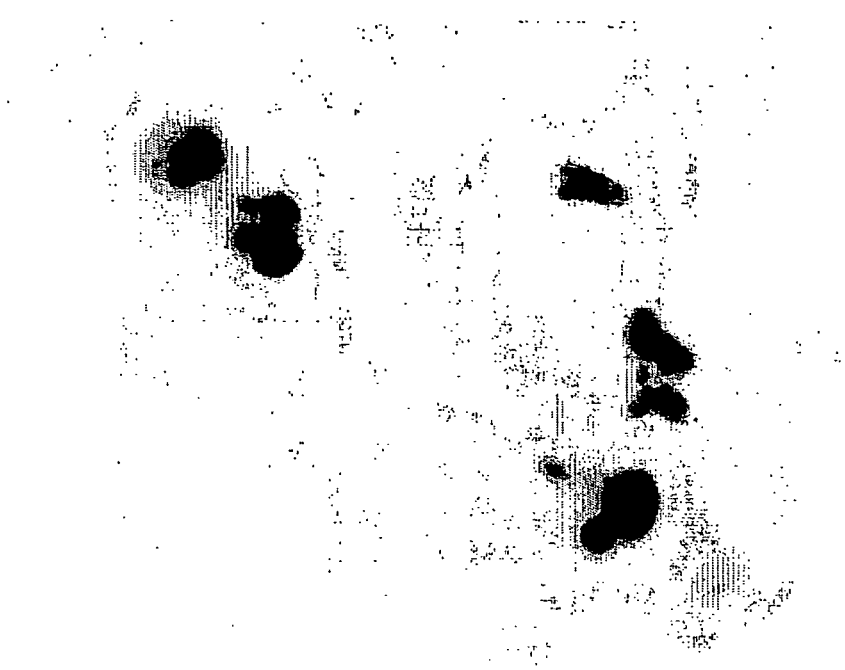
Figure 14 is an inverted image of directly stained apoptotic cells.

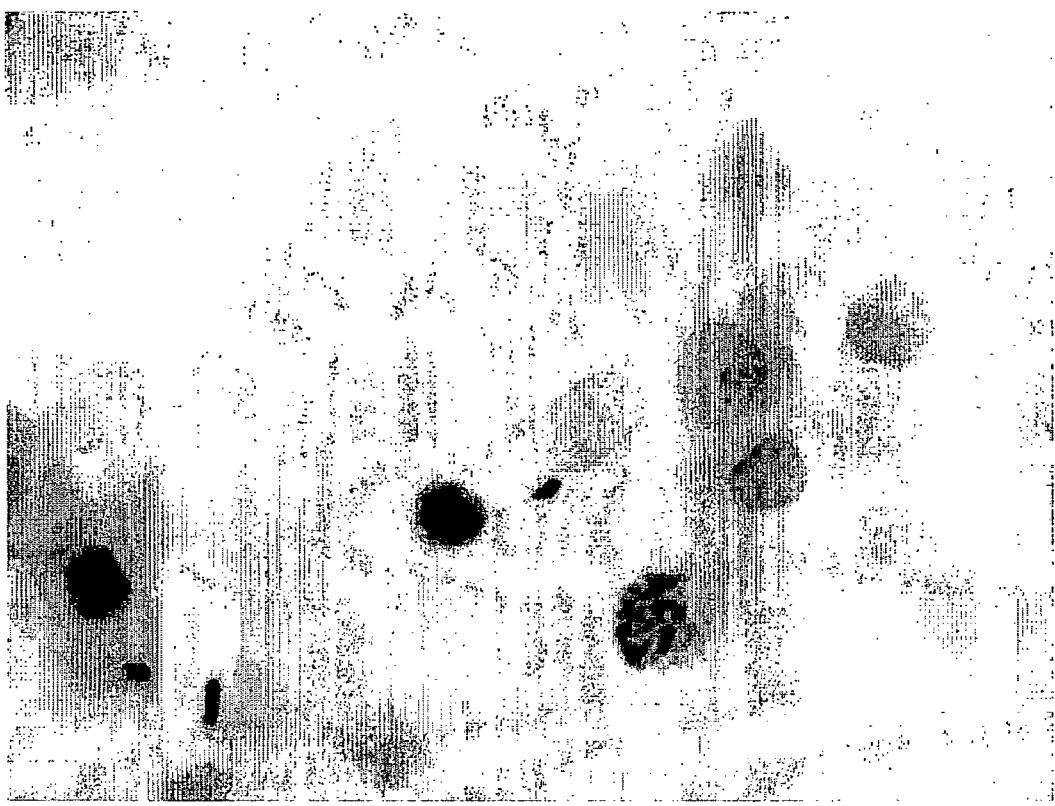
Figure 15 is an inverted image of EuMac-anti-5-BrdU stained cells in S phase.

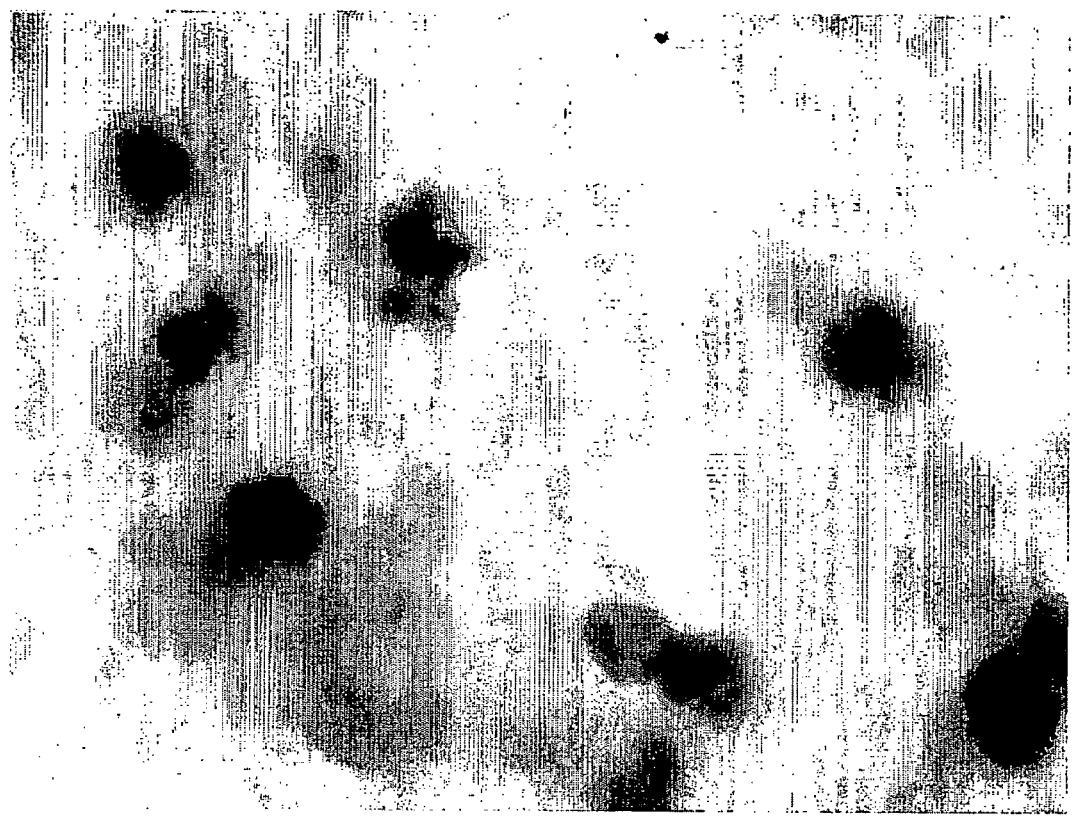
Figure 16 is an inverted image of EuMac-Streptavidin stained apoptotic cells.

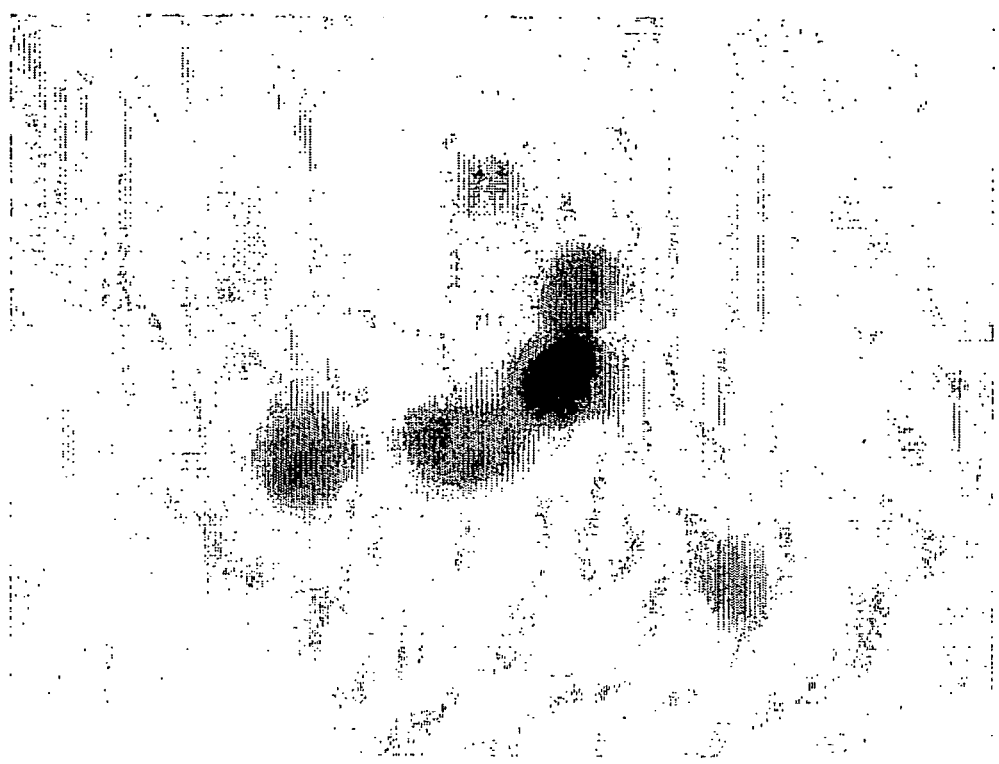
Figure 17 is an inverted image of EuMac-Streptavidin stained cells in S phase.

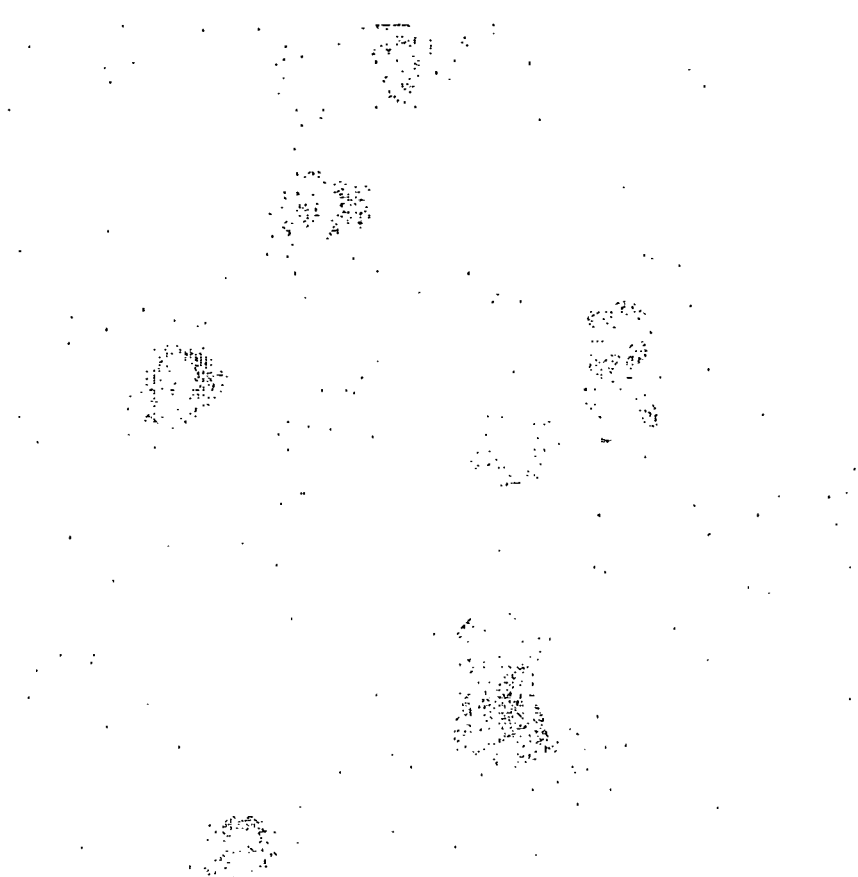
Figure 18 is an inverted image of two photon excited EuMac-di-NCS stained cells.

REAGENT SYSTEM AND METHOD FOR MODIFYING THE LUMINESCENCE OF LANTHANIDE(III) MACROCYCLIC COMPLEXES

BACKGROUND OF THE INVENTION

To facilitate understanding of the composition and method of this invention, the following definitions of terms used throughout this specification and claims are provided.

1. The term "equivalent(s)" is used in the chemical sense to describe a quantity of a specific component of a molecule or of a specific ion of a salt. Thus a 1M solution of $GdCl_3$ would contain 1 equivalent of the gadolinium ion and 3 equivalents of the chloride ion in 1 liter of solution.
2. The term "light" is used to designate any form of electromagnetic radiation, including the ultraviolet, visible, and infrared region of the spectrum.
3. The term "photon" is used to designate an individual particle of light.
4. The term "lanthanide" is used to designate any of the lanthanide elements (atomic number 57-71) as well as the lanthanide-like yttrium and the actinide elements (atomic number 89-103).
5. The term "chemical compound" follows the common usage of the field of chemistry and is used to describe any pure substance that is formed when atoms of two or more different elements combine and create a new material that has a constant composition throughout and properties that are unlike those of the constituent elements.
6. The term "complex" is used to describe any species in which a metal atom or ion is bonded to an organic moiety. Examples of complexes include the lanthanide (III) macrocycles of U.S. Pat. Nos. 5,373,093 and 5,696,240; the cryptates of U.S. Pat. Nos. 4,927,923, 5,162,508, and 5,534,622; the phthalamidyl-containing chelates of U.S. Pat. No. 6,515,113; the salicylamidyl-containing chelates of U.S. Pat. No. 6,406,297; and the chelates formed with the reaction product of diethylenetriaminepentaacetic acid dianhydride (DTPAA) and p-aminosalicylic acid of U.S. Pat. No. 4,962,045. In such a complex, each bond between the metal atom or ion and the organic moiety consists of a shared electron pair originally belonging solely to the organic moiety. Since many complexes can be isolated or identified by standard techniques, they are chemical compounds.
7. The term "ligand" is used to describe the organic moiety of a complex.
8. The term "unidentate ligand" is used to describe a molecule or ion that binds to a metal atom or ion through a single site, and more specifically through a single atom or a through the electrons of one multiple bond between a pair of atoms.
9. The term "multidentate ligand" is used to describe a molecule or ion that can bind to a metal atom or ion through two or more sites, and more specifically through two or more atoms, or through the electrons of two or more multiple bonds between pairs of atoms, or through a combination of thereof.
10. The term "eteroatom" is used to indicate any atom of a cyclic molecule or of a cyclic portion of a molecule or ion, that is not carbon.
11. The term "macrocycle" is used to describe a cyclic organic compound in which the cycle consists of nine or more members, including carbon and all eteroatoms with three or more of such atoms capable of acting as electron pair donors (ligands) toward metal atoms or ions.
12. The term "macrocyclic ligand" is used to describe a macrocycle that functions as ligand in a complex.
13. The term "lanthanide macrocycle" means a complex where one or more lanthanide atoms or ions are bound into the cavity of a macrocyclic ligand.
14. The abbreviation "LnMac" will be used to describe all of the functionalized macrocycles taught in U.S. Pat. Nos. 5,373,093 and 5,696,240.
15. The registered trademark "Quantum Dye®" is and has been used to describe all of the functionalized macrocycles taught in U.S. Pat. Nos. 5,373,093 and 5,696,240.
16. The term "unitary solution" is used to describe a homogenous solution that consists of a single phase.
17. The term "unitary luminescence enhancing solution" is used to describe a unitary solution that after evaporation of the solvent to dryness results in a solid that enhances the luminescence of an energy transfer acceptor lanthanide(III) complex by a mechanism other than completing the complexation of the lanthanide ion.
18. The term "homogeneous" is used to describe a material that has a constant composition except for the material to be measured.
19. The term "homogeneous solid composition" is used to describe a material that does not flow, contains two or more chemical species, and is homogenous.
20. The term "luminescence enhancing solid composition" is the homogeneous solid composition produced by the drying of the unitary luminescence enhancing solution.
21. The term "processed specimen" is used to describe the material present after conventional clinical or research processing.
22. The term "labeled specimen containing composition" is used to describe a composition that includes a processed specimen with one or more labels embedded in the luminescence enhancing solid composition.
23. The terms "nucleic acid material" and "nucleic acids" each refer to deoxyribonucleotides, ribonucleotides, or analogues thereof in either single- or double-stranded form. Unless specifically limited, the term encompasses nucleic acids containing known analogues of natural nucleotides that have similar properties as the reference natural or antisense nucleic acid. Thus "nucleic acids" includes but is not limited to DNA, cDNA, RNA, antisense RNA, double-stranded RNA, and oligonucleotides. A therapeutic nucleic acid can comprise a nucleotide sequence encoding a therapeutic gene product, including a polypeptide or an oligonucleotide.

Nucleic acids can further comprise a gene (e.g., a therapeutic gene), or a genetic construct (e.g., a gene therapy vector). The term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

24. The term "energy transfer donor" is used to designate any molecular or ionic species capable of transferring all or part of the energy absorbed from light to another molecular or ionic species.
25. The term "energy transfer donor metal ion" is used to designate any metal ion that is itself, or is part of a complex that serves as, an "energy transfer donor". This complex need not itself be ionic. This energy transfer can be direct or indirect if the presence of the metal ion induces another molecule or ion, including but not limited to those with which it has formed a complex, to transfer energy to another molecular or ionic species.
26. The term "energy transfer donor complex of a metal ion" is used to designate any complex of an energy transfer donor metal ion that is capable of transferring all or part of the energy absorbed from light to another molecular or ionic species.
27. The term "energy transfer acceptor" is used to designate any molecular or ionic species capable of accepting all or part of the energy absorbed from light by another molecular or ionic species.
28. The term "energy transfer acceptor lanthanide(III)" is used to designate a lanthanide(III) that accepts energy from one or more molecules or ions, and as a result of this process emits part of this energy as a photon.
29. The term "energy transfer acceptor lanthanide(III) complex" is used to designate any lanthanide(III) complex or compound that is capable of accepting energy, directly or indirectly, from an energy transfer donor and of emitting photons with energies equal to or less than the energy received.
30. The term "resonance energy transfer" is used to describe a process by which an energy transfer donor transfers energy to an energy transfer acceptor.
31. The term "RET" is an abbreviation for "resonance energy transfer".
32. The term "heterogeneous resonance energy transfer" is used to describe a process by which an energy transfer donor transfers all or part of the energy absorbed from light to an energy transfer acceptor, where the energy transfer donor and energy transfer acceptor are different molecular species.
33. The term "homogeneous resonance energy transfer" is used to describe a process by which any molecular species transfers all or part of the energy absorbed from light to another member of the same molecular species.
34. The term "columinescence" is used to describe the increase in luminescence brought about by the addition of a luminescence-enhancing amount of at least one energy transfer donor complex of a metal ion to one or more energy transfer acceptor lanthanide(III) complexes, where the emission spectrum of the energy transfer donor species differs from that of the one or more energy transfer acceptor lanthanide(III) complexes. The "term Lanthanide Enhanced Luminescence" that has been previously used is a synonym for columinescence
35. The term "columinescence solution" is used to describe a solution, the use of which results in "columinescence." The term "lanthanide enhanced luminescence solution" that has been previously used is a synonym for columinescence
36. The term "LEL solution" is an abbreviation for "lanthanide enhanced luminescence solution."
37. The term "reactive functionality" is used to mean a first atom or group capable of reacting with a second atom or group forming a covalent bond with it, as previously used in U.S. Pat. Nos. 5,373,093 and 5,696,240 to mean that both the first and second atom or group are capable of forming a covalent bond with one another. These atoms or groups include but are not limited to amine, azide, alcoholic hydroxyl, phenolic hydroxyl, aldehyde, carboxylic acid, carboxamide, halogen, isocyanate, isothiocyanate, mercapto and nitrile substituents. Functionalized alkyl, functionalized aryl-substituted alkyl, functionalized aryl, and functionalized alkyl-substituted aryl signify the respective alkyl, aryl-substituted alkyl, aryl, and alkyl-substituted aryl groups substituted with a reactive functionality.
38. A "peptide" is a polymer that is composed of monomer units that primarily are amino acids. The peptide monomer units are linked to one another by amide bonds.
39. The term "label" means the species or moiety that permits a molecule to be detected or to be affected non-destructively by a physical means.
40. The term "tag" is a synonym for "label".
41. The term "optical-label" means the species or moiety that permits a molecule to be detected by optical means including emission of photons from both singlet and triplet electronic excited states.
42. The term "labeled" designates a molecule that has formed a covalent bond with a label.
43. The term "tagged" is a synonym for "labeled".
44. The term "labeled-polymer" means a polymer to which one or more labels are attached.
45. The term "tagged-polymer" is a synonym for "labeled-polymer".
46. The term "labeled-polymer-conjugate" means a labeled-polymer where this polymer has formed a covalent bond with a molecular species other than itself or its label(s).
47. The term "tagged-polymer-conjugate" is a synonym for is a synonym for "Labeled-polymer-conjugate".
48. The term "fluorescence" means a process by which an electron of a molecule or ion that is in an electronic singlet state (a state in which the spins of all electrons are paired) absorbs the energy contained in one or more photons, with the result that this electron is elevated to a higher energy singlet state, and subsequently an electron of this molecule or ion loses energy in the form of a quantum of energy and deactivates to a lower energy state. This process does not involve a change in the electronic spin multiplicity of the molecule or ion. This quantum of energy can be in the form of an emission of a photon or transfer of energy to a neighboring molecule or ion.
49. The term "fluorophore" means a molecule or ion capable of fluorescence.
50. The term "luminescence" means all processes by which an electron of a molecule or ion absorbs the energy contained in one or more photons, with the result that this electron is elevated to a higher energy singlet state, subsequently relaxes to a lower energy triplet state, and subsequently energy is lost from an electron of this molecule or ion in the form of a quantum of energy with the concurrent deactivation of this electron to a lower state. This process involve a change of the electronic spin multiplicity of the molecule or ion. This quantum of energy can be in the form of an emission of a photon or transfer of energy to a neighboring molecule or ion.
51. The term "lumiphore" means a molecule or ion capable of luminescence.
52. The term "light absorption" means a process by which an electron in a molecule or ion absorbs the energy contained in one or more photons.

53. The term "optical-label" means a label capable of fluorescence, luminescence, or absorption.
54. The term "luminescence-label" means an optical-label that is capable of luminescence, such as a lanthanide macrocycle.
55. "The term fluorescence-label" means an optical-label that is capable of fluorescence.
56. "The term absorption-label" means an optical-label that is capable of absorption.
57. The term "specific combining pair" means a pair of molecules that forms a stable complex.
58. The term "bridging molecule" means any molecule that can be simultaneously bound to a label and a member of a specific combining pair.
59. The term "analyte" means any compound of interest, naturally occurring or synthetic, that can bind to a member of a specific combining pair that is to be quantitated.
60. An "analyte-binding species" is the member of a specific combining pair that can form a stable complex with an analyte. These analyte-binding species include but are not limited to:
    a) an antibody or antibody fragment.
        (i) Such antibodies or fragments may be defined to include polyclonal antibodies from any native source and native or recombinant monoclonal antibodies of classes IgG, IgM, IgA, IgD, and IgE; hybrid derivatives, and fragments of antibodies including Fab, Fab' and F(ab')$_2$; humanized or human antibodies; recombinant or synthetic constructs containing the complementarity determining regions of an antibody, and the like. The methods useful for construction of all such antibodies are known to those of skill in the art.
    b) a polynucleotide, polynucleotide fragment, or an oligonucleotide.
        (i) Such polynucleotides, polynucleotide fragments, or oligonucleotides include but are not limited to: deoxynucleic acids, DNAs; ribonucleic acids, RNAs; and peptide nucleic acids, PNAs.
    c) a protein that is a member of specific combining pair.
        (i) Such proteins include but are not limited to avidin, streptavidin, and their derivatives.
    d) a lectin.
61. The term "indirectly labeled" means a process where an analyte-binding species is a member of two specific combining pairs. The other member of the first specific combining pair is a labeled molecule. The other member of the second specific combining pair is an analyte. The analyte-binding species is bound to both the analyte and the labeled molecule.
62. The term "co-hybridization" means a process where two DNA samples differing in at least one property are hybridized with a third DNA.
63. The term "material" is defined to include: cells, organisms, bacteria, viruses, histological sections, organic and inorganic particulates and matter, and any other discernible material which provides diagnostic and/or analytical information whatsoever.
64. The term "microscopic analysis" is defined to be a process wherein a microscope under human and/or a machine control is used for visualization, analysis, and/or enumeration, and/or categorization, and/or photography, and/or electronic image acquisition of material.
65. The term "receiving surface member" will be used in a generic sense to describe all discrete objects which serve as substrates to support material for microscopic viewing and/or observation and/or analysis. The current, most common receiving surface member is a microscope slide, which is a glass rectangular object that is approximately 1 mm thick, 25 mm wide, and 75 mm long. These are the items conventionally referred to as microscope slides for laboratory and commercial purposes.

As used herein and in the appended statements of the invention, the singular forms "a", "and", and "the" include plural referents unless the context clearly dictates otherwise. Thus, for example, reference to "a construct" includes a plurality of such constructs, and so forth.

The term "about", as used herein when referring to a measurable value such as an amount of weight, time, dose, etc. is meant to encompass variations of in one embodiment ±20% or ±10%, in another embodiment ±5%, in another embodiment ±1%, and in still another embodiment ±0.1% from the specified amount, as such variations are appropriate to perform the disclosed methods.

The term "expression", as used herein to describe a genetic construct, generally refers to the cellular processes by which a biologically active polypeptide or biologically active oligonucleotide is produced from a DNA sequence.

The term "construct", as used herein to describe a genetic construct, refers to a composition comprising a vector used for gene therapy or other application. In one embodiment, the composition also includes nucleic acids comprising a nucleotide sequence encoding a therapeutic gene product, for example a therapeutic polypeptide or a therapeutic oligonucleotide. In one embodiment, the nucleotide sequence is operatively inserted with the vector, such that the nucleotide sequence encoding the therapeutic gene product is expressed. The term "construct" also encompasses a gene therapy vector in the absence of a nucleotide sequence encoding a therapeutic polypeptide or a therapeutic oligonucleotide, referred to herein as an "empty construct." The term "construct" further encompasses any nucleic acid that is intended for in vivo studies, such as nucleic acids used for triplex and antisense pharmacokinetic studies.

The terms "bind", "binding", "binding activity" and "binding affinity" are believed to have well-understood meanings in the art. To facilitate explanation of the present invention, the terms "bind" and "binding" are meant to refer to protein-protein interactions that are recognized to play a role in many biological processes, such as the binding between an antibody and an antigen, and between complementary strands of nucleic acids (e.g. DNA-DNA, DNA-RNA, and RNA-RNA). Exemplary protein-protein interactions include, but are not limited to, covalent interactions between side chains, such as disulfide bridges between cysteine residues; hydrophobic interactions between side chains; and hydrogen bonding between side chains.

The terms "binding activity" and "binding affinity" are also meant to refer to the tendency of one protein or polypeptide to bind or not to bind to another protein or polypeptide. The energetics of protein-protein interactions are significant in "binding activity" and "binding affinity" because they define the necessary concentrations of interacting partners, the rates at which these partners are capable of associating, and the relative concentrations of bound and free proteins in a solution. The binding of a ligand to a target molecule can be considered specific if the binding affinity is about $1\times10^4$ M$^{-1}$ to about $1\times10^6$ M$^{-1}$ or greater.

The phrase "specifically (or selectively) binds", for example when referring to the binding capacity of an antibody, also refers to a binding reaction which is determinative of the presence of the antigen in a heterogeneous population of proteins and other biological materials. The phrase "specifically (or selectively) binds" also refers to selective targeting of a targeting molecule, such as the hybridization of a RNA molecule to a nucleic acid of interest under a set of hybridization conditions as disclosed herein below.

| Table of Abbreviations | |
|---|---|
| BSA | bovine serum albumin |
| cDNA | complementary DNA |
| CIA | chloroform/isoamyl alcohol |
| CTAB | cetyltrimethylammonium bromide |
| dATP | deoxyadenosine triphosphate |
| dCTP | deoxycytidine triphosphate |
| dGTP | deoxyguanosine triphosphate |
| DMF | dimethylformamide |
| DMSO | dimethylsulfoxide |
| DNA | deoxyribonucleic acid |
| dNTP | deoxynucleotide triphosphate |
| dTTP | deoxythymidine triphosphate |
| dUTP | 2'-deoxyuridine 5'-Triphosphate |
| EDTA | ethylenediaminetetraacetic acid |
| Eqv | equivalent(s) |
| Eqv/L | equivalent(s) per Liter |
| EuMac-d-UTP | EuMac-5-deoxyuridine triphosphate |
| h or hr | hour(s) |
| $H_2PDCA$ | 2,6-pyridinedicarboxylic acid |
| HTTFA | thenoyltrifluoroacetone |
| L | liter(s) |
| LEL | Lanthanide Enhanced Luminescence |
| Ln(III) or $Ln^{3+}$ | a trivalent lanthanide cation |
| LnMac | See Definition 14. |
| LnMac-d-UTP | LnMac-5-deoxyuridine triphosphate |
| M | molar |
| M | molar |
| mg | milligram(s) |
| min | minute(s) |
| mL | milliliter(s) |
| mM | millimolar |
| mm | millimeter |

| Table of Abbreviations | |
|---|---|
| mmol | millimole(s) |
| mmol/L | millimoles per liter |
| mRNA | messenger RNA |
| msec | millisecond(s) |
| nEqv | nanoequivalent |
| ng | nanogram(s) |
| nmol | nanomole(s) |
| PB | phosphate buffer |
| PBS | phosphate buffered saline |
| PCR | polymerase chain reaction |
| PDCA | The dianion of 2,6-pyridinedicarboxylic acid |
| PEG | polyethylene glycol |

| Table of Abbreviations | |
|---|---|
| RET | Resonance Energy Transfer |
| RNA | ribonucleic acid |
| rpm | revolutions per minute |
| SDS | sodium dodecyl sulfate |
| sec | seconds(s) |
| SmMac-d-UTP | SmMac-5-deoxyuridine triphosphate |
| TbMac-d-UTP | TbMac-5-deoxyuridine triphosphate |
| TTFA | The anion of thenoyltrifluoroacetone |
| μg | microgram(s) |
| μL | microliter(s) |
| μM | micromolar |
| μmol | micromole(s) |
| μmol/L | micromoles per liter |
| μsec | microsecond(s) |

FIELD OF THE INVENTION

This invention concerns: Composition of matter and a process to enhance and/or modify the luminescence of covalently coupled optical-labels containing lanthanide(III) complexes, especially when functioning as labels for detecting members of combining pairs, and to permit the detection and quantitation of low levels of these optical-labels.

To facilitate the use of references in this text, the citations are given in full at the end. The reference number preceded by Ref. in parenthesis (Ref. number) is employed for citations. Citations to books include the first page or chapter of the section of interest. US patents are cited both by number and as references.

1. Prior Art

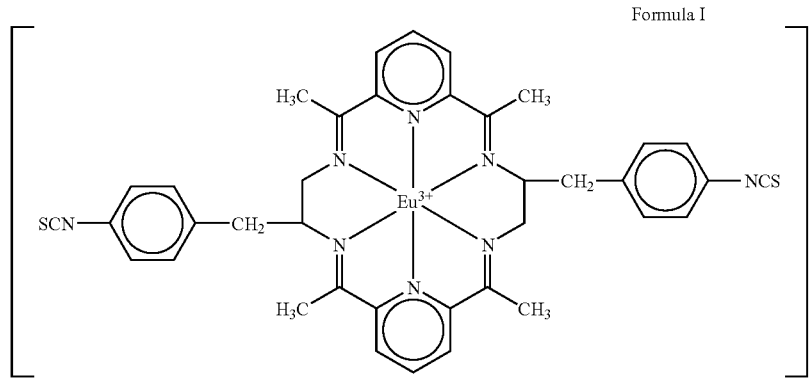

Formula I

Vallarino and Leif have reported in U.S. Pat. No. 5,373,093, 1994 (Ref. 1) and its Continuation-In-Part U.S. Pat. No. 5,696,240, 1997 (Ref. 2) on symmetrically di-functionalized water soluble macrocyclic complexes of lanthanide, actinide, and yttrium ions. A di-functionalized macrocyclic complex is represented by the schematic Formula I:

Formula I is the di-isothiocyanate derivative having the structure shown in column 10 of U.S. Pat. No. 5,373,093. Specifically, it is one of the isomers of the cationic europium macrocyclic moiety containing a 4-isothiocyanato-benzyl-substituent on each of the aliphatic side-chains. The empirical formula of the moiety is $C_{38}H_{36}N_8S_2Eu$. Its trichloride was used in liquid phase coupling reactions of this application. The organic macrocycle and its functionalized derivatives act as ligands to lanthanide, actinide and yttrium ions.

In U.S. Pat. No. 5,696,240, asymmetrically mono-functionalized water soluble macrocyclic complexes of lanthanide, actinide and yttrium ions are described. A mono-functionalized macrocyclic complex is represented by the schematic Formula II:

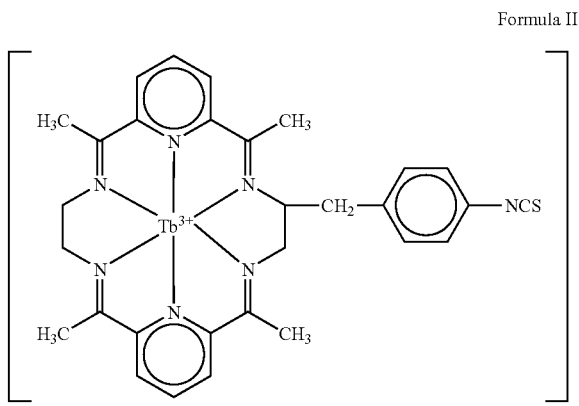

Formula II

Formula II is the mono-isothiocyanate derivative having the structure shown in Claim 13 of U.S. Pat. No. 5,696,240. Specifically, it is the cationic terbium macrocyclic moiety containing a 4-isothiocyanato-benzyl-substituent on one of the aliphatic side-chains. The empirical formula of the moiety is $C_{30}H_{31}N_7STb$.

The following abbreviations will be used to describe species having structures related to those shown in Formula I, Formula II, and subsequent Formulas.

Any and all of the metal ions selected from the group consisting of a lanthanide having atomic number 57-71, an actinide having atomic number 89-103, and yttrium having atomic number 39 will have M as their abbreviation in formulas. Specific metal ions will be given as their standard chemical symbols. The unfunctionalized, mono-functionalized and di-functionalized macrocyclic complexes will be abbreviated respectively as "Mac-un", "Mac-mono" and "Mac-di". The term "Macs" without the -un, -mono, or -di suffix will include the unfunctionalized, mono-functionalized and di-functionalized macrocyclic complexes (Mac-un, Mac-mono and Mac-di). When a specific peripheral pendant substituent having at least one reactive site (reactive functionality) is mentioned, its abbreviation will be given as a suffix. Thus, the compound shown in Formula I is abbreviated as EuMac-di-NCS. The compound shown in Formula II is abbreviated as ThMac-mono-NCS. The abbreviation, LnMac, will refer to any and all of the macrocyclic species covered by U.S. Pat. Nos. 5,373,093 and 5,696,240. These macrocyclic species are lanthanide(III) complexes. These can be referred to as compounds. In the solid state, in order to achieve electronic neutrality, they have accompanying anions, such as chlorides.

The entire disclosures of U.S. Pat. No. 5,373,093 and its Continuation-In-Part U.S. Pat. No. 5,696,240 are here incorporated by reference.

Leif et al. 1994 (Ref. 3) described the use of symmetrically di-isothiocyanate-functionalized macrocyclic complexes of a lanthanide(III) ion, which served as the light-emitting center. The isothiocyanate functionalities allow covalent coupling of the lanthanide(III) macrocycles to a biosubstrate. The Eu(III) and Tb(III) macrocyclic complexes possess a set of properties—water solubility, inertness to metal release over a wide pH range, ligand-sensitized narrow-band luminescence, large Stoke's shift, and long excited-state lifetime—that provide ease of staining as well as maximum emission signal with minimum interference from background autofluorescence. These authors stated, "The results with the $^5D_0 \rightarrow {^7F_2}$ (610-625 nm) Eu(III) transition, which is the major signal source, show that the luminescence of the EuMac-enhancer system is highly dependent upon the choice of both buffer and solvent. The emission intensity increases dramatically in the absence of those buffers that contain anions, such as carbonate, capable of competing with the β-diketonate enhancers as ligands for Eu(III). The emission intensity also increases greatly in the less hydroxylic solvents. However, vibrational deactivation by interaction with the —OH groups of solvent molecules can not be solely responsible for the energy loss, since substitution of $D_2O$ for $H_2O$ as the solvent had been reported (Ref. 4) to result only in a three-fold increase of the EuMac excited-state lifetime."

The low quantum yield of the emission of the EuMac in aqueous medium probably precludes its use as an optical-label for the observation and measurements of live cells (Ref. 3). However, this complex can be used in conventional fluorescence (luminescence) microscopy, providing the cells are mounted in the appropriate nonaqueous medium.

Leif and Vallarino have taught in U.S. Pat. No. 6,340,744 (Ref. 5) and U.S. Pat. No. 6,750,005 (Ref. 6)"A spectrofluorimetrically detectable luminescent composition comprising water, a micelle-producing amount of at least one surfactant, at least $1 \times 10^{-10}$ moles/liter of at least one energy transfer acceptor lanthanide element macrocycle compound having an emission spectrum peak in the range from 500 to 950 nanometers, and a luminescence-enhancing amount of at least one energy transfer donor compound of yttrium or a 3-valent lanthanide element having atomic number 59-71, provided that the lanthanide element of said macrocycle compound and the lanthanide element of said energy transfer donor compound are not identical."

The enhanced luminescence of compositions according to U.S. Pat. Nos. 6,340,744 and 6,750,005 permits the detection and/or quantitation of the lanthanide(III) macrocycle compounds and complexes thereof without the use of expensive and complicated time-gated detection systems. As a result, these macrocycle compounds and complexes thereof are useful as reporter molecules in immunoassays, analytical cytology, histological staining, and imaging processing.

The increase in emission intensity of the lanthanide enhanced luminescence solutions according to U.S. Pat. Nos. 6,340,744 and 6,750,005, caused by an energy transfer donor complex of a different metal ion, can also occur with functionalized derivatives of energy transfer acceptor lanthanide (III) complexes, for instance with lanthanide macrocycles containing one or more reactive functional groups at which reaction with analyte-binding species and/or analytes can take place; with reaction products of functionalized derivatives of such energy transfer acceptor lanthanide(III) complexes with such analyte-binding species and/or analytes. The analytes include small molecules of biological interest having molecular weights from 125 to 2000 daltons, such as nucleic acid bases or haptens, and large molecules of biological interest having molecular weights greater than 2000 daltons, such as proteins including antibodies, polysaccharides, or nucleic acids.

In a preferred composition according to U.S. Pat. No. 6,340,744, the energy transfer donor compound is an ionic compound of, or a complex of, gadolinium(III). The gadolinium(III) halides and especially gadolinium(III)trichloride are particularly preferred.

The enhanced luminescence composition of U.S. Pat. No. 6,340,744 exists in a micellar organization. The importance of micellar organization to the enhanced luminescence composition is demonstrated by the observation that a water-miscible polar solvent such as ethanol, when added to the characteristically cloudy and luminous composition, completely eliminates the luminescence and simultaneously turns the cloudy micellar liquid to a clear solution. Once formed in an aqueous micellar organization, the composition of U.S. Pat. No. 6,340,744 can be transferred to an immiscible non-aqueous medium and/or dried, as by evaporation or lyophilization, with preservation of its luminescence. To provide the micellar organization, the composition includes a micelle-forming amount of a surfactant.

Cetyltrimethylammonium bromide, a cationic surfactant, is used in the preferred embodiment of U.S. Pat. No. 6,340,744. The preferred concentrations for this surfactant range from $1.0 \times 10^{-4}$ to $1.0 \times 10^{-6}$ M.

The entire disclosure of U.S. Pat. Nos. 6,340,744 and 6,750,005 are here incorporated by reference.

Columinescence (LEL)

Xu and Hemmila (Ref. 7) have described a luminescence enhancement system consisting of the ternary chelates of the lanthanide ions $Eu^{3+}$, $Sm^{3+}$, $Tb^{3+}$ or $Dy^{3+}$ with PTA (Pivaloyltrifluoroacetone) and 1,10-phenanthroline (Phen) using $Y^{3+}$ as the enhancing ion. Ref 7 states, "The optimum PTA concentration for $Tb^{3+}$ detection was narrow and the fluorescence diminished rapidly at PTA concentrations above 70 µM, whereas for $Eu^{3+}$ detection the optimum PTA concentration was wider (FIG. 1), 50 µM PTA was used in subsequent experiments." The optimum concentration of 1,10-phenanthroline was 50 µM. Triton X-100 was employed as the surfactant. The greatest luminescence enhancement was produced by Y(III) at 75 µM, which was followed by Lu(III) and Gd(III). The enhancement with these two ions was essentially equal; and greater than the enhancement with La(III). The pH optimum of the columinescence solution was between 7.2 and 7.3. Increases in the ethanol concentration "decreased the $Eu^{3+}$ fluorescence but did not change the $Tb^{3+}$ fluorescence at Triton X-100 concentrations below its critical micelle concentration (0.015%)." As shown in FIG. 3 of Ref 7, The luminescence of both Eu(III) and Tb(III) decreased independently of the Triton X-100 concentration when the ethanol concentration was above 30%. The complexes of the Eu(III), Tb(III), Sm(III), and Dy(III) had excititation maxima in the range of 312 to 316 nm and emission maxima respectively at 612, 544, 647, and 574 nm. The lifetimes of the Eu(III) and Tb(III) complexes were longer and the detection limits greater than those of the Sm(III), and Dy(III).

Tong et al. (Ref. 8) have described the enhancement of the luminesce of the complex of Dy(III) with 1,6-bis(1'-phenyl-3'-methyl-5'-pyrazol-4'-one)hexanedione (BPMPHD) by the cationic surfactant cetyltrimethylammonium bromide (CTMAB) [CTAB] and Gd(III). The excitation and emission maxima were respectively 300 nm and 578 nm. The fluorescence intensity of the Dy-BPMPHD system was reported to be enhanced about sevenfold by adding CMTAB with a further eightfold enhancement by the addition of Gd(III). The necessity of a miscellular system for the columinescence effect was demonstrated by Tong et al., who stated, "that the fluorescence intensity of the system changes greatest when CTMAB is at its apparent cmc (critical miscellular concentration) indicates that the formation of micelles has a great effect on the increase in the fluorescence intensity in the system." A miscellular system was also demonstrated (Ref. 8) to be required for maximum luminescence because "The co-luminescence effect disappeared if the organic solvent concentrations were more than 70% for ethanol, 50% for acetone and 80% for dimethyl sulfoxide, when the turbid system became transparent." Tong et al. concluded, "From the effects of surfactants and solvents on the fluorescence intensity, we conclude that the co-luminescence effect only occurs in the surfactant micellar system or turbid coprecipitated system." This confirms the intermolecular energy transfer luminescence mechanism.

Tong et al. (Ref. 8) described the mechanism of columinescence as being, "Because $Gd^{3+}$ possesses a relatively stable half-filled 4f shell and the luminescence level of $Gd^{3+}$ $^6P_{7/2}$ is higher than the triplet state of BPMPHD in the complex $[Gd(BPMPHD)_2].CTMAB^+$, the energy of the latter cannot be transferred to $Gd^{3+}$, but can be transferred to the luminescence $^4F_{9/2}$ level of $Dy^{3+}$ in the $[Dy(BPMPHD)_2].CTMAB^+$ complex by intermolecular energy transfer owing to the short distance between the two complexes in the micelle." This same explanation can also be applied to the effect of Gd(III) on the EuMac, TbMac, and SmMac in a miscellular solution.

Yang et al. (Ref. 9) described luminescence studies of doped silica gels and coprecipitates in the form of powders of complexes of TTFA and phenanthroline with either 100% Eu(III) or 80% Eu(III) and 20% Gd(III). In the case of the powered complexes, the presence of the Gd(III) increased the luminescence produced by the Eu(III) in the coprecipitates by about 47% and decreased the luminescence produced by the Eu(III) in the doped silica gels by about 18%. The effect of distance on energy transfer was proposed to explain these opposite effects. It was proposed that the Gd(III) complexes were nearer to the Eu(III) powdered complexes in the coprecipitates than in the doped silica gels.

Blasse et al. (Ref. 10) described emission of a Tb(III) impurity of $La(2,2'\text{-bypyridine})_3^{3+}$. The material was prepared for luminescence spectroscopy by being "pressed in the cryostat on a bed of MgO." They reported that, "Upon measuring the emission spectrum as a function of temperature, a peculiar phenomenon occurred. A certain amount of $Tb^{3+}$ emission appeared when the ligand phosphorescence intensity decreased." As shown in FIG. 2 of Ref. 10, the Tb(III) emission rapidly increased when the temperature was raised from 4.2 K to about 100 K and then rapidly decreased to about background at 200 K. Blasse et al. stated, "This behavior of the $Tb^{3+}$ impurity emission, suggest strongly that the $^3(\pi,\pi^*)$ excited state is not localized but migrates among the several bpy (2,2'-bypyridine) groups." This migration includes the transfer of energy to the Tb(III).

The term LEL is used; rather than cofluorescence because LEL was used in the patents and publications described below. The limited stability and reproducibility of the micellar Lanthanide Enhanced Luminescence solution described by Leif and Vallarino in U.S. Pat. No. 6,340,744 (Ref. 5) and U.S. Pat. No. 6,750,005 (Ref. 6), by Bromm et al. 1999 (Ref. 11) and Quagliano et al. 2000 (Ref. 12), as well as the impairment of cellular morphology by the emulsifying agents are significant problems that have impeded commercialization. In order to have a reliable, convenient commercial product, the LEL emulsion needs to be stored and shipped, preferably in the form of a single material. However, this option has intrinsic difficulties, because the LEL emulsion is both temperature and oxygen sensitive; it also deteriorates upon prolonged storage at 4° C. At present, the LEL emulsion is prepared at the time of use by the addition of a small amount of an ethanolic solution to an aqueous solution, followed by rapid mixing. The LEL aqueous component contains $GdCl_3$, salts, buffer, detergent and gelatin. The water used for the buffer is boiled to remove oxygen prior to the addition of the ingredients. The LEL ethanolic solution contains: HTTFA, cetyltrimethylammonium bromide, and 1,10-phenanthroline. The extent of luminescence enhancement produced by this solution depends on the method of mixing, the time elapsed after mixing, and the oxygen content of the solution. The micellar solution is also sensitive to temperatures above 60° C.

Ultrasonication was explored because it had the potential of increasing the reproducibility of the luminescence enhancement by reproducibly forming a solution containing small micelles with minimal size dispersion, which should enhance the shelf-life of a one-component Columinescence solution. A Branson Model 450 Digital Sonifier with a High-intensity Cup Horn was extensively tested. The use of the water cooled Cup Horn had the significant potential advantage of permitting the LEL solution to be emulsified in a standard plastic screw-top 50 mL vial. This eliminated the problems of metal contamination from the standard ½" Horn container and of aerosol production. Unfortunately, the homogenization was often incomplete and the luminescence was decreased.

In order to create a closed, effectively cooled system, the original High-intensity Cup Horn was replaced by a flow-through ultrasonic horn. The liquid was cooled prior to its entry into the head and after it exits. However, this did not solve the problem of the decrease in luminescence resulting from ultrasonic mixing. It was concluded that the loss of intensity of the LEL solution stored as a single material was too high to be acceptable.

It was found that the addition of antioxidants and fluorescence protecting agents also caused a decrease in luminescence.

These experimental observation pointed out the shortcomings of a single material LEL solution. Therefore, the product is to be supplied as one aqueous and one ethanolic solution to be mixed at the time of use. It was also observed that the originally developed LEL solution impaired cellular morphology and did not produce significant luminescence when EuMac-streptavidin was bound to biotinylated microtiter plates. This loss of luminescence was presumably caused by the desorption of the biotin from the plastic microtiter plates. These problems were solved by replacing the trioctylphosphine oxide (TOPO) by gelatin in the LEL solution (Ref. 13).

The photo-decomposition of some component of the LEL solution (presumably, the HTTFA) resulted in a loss of luminescence. This loss could be reversed by the addition of new LEL solution, and it was noted that the rate of luminescence loss was much slower for a plastic embedded sample than for the aqueous LEL solution (Ref. 13).

Some of the content of the provisional application (Ser. No. 60518605) for this invention has been published (Ref. 14).

Europium Macrocycle Labeled Peptides

The solid phase synthesis of peptides labeled with the europium macrocycle, and capable of subsequent coupling with biologically active and/or biologically compatible molecules, has been described (Refs. 15 & 16). These europium macrocycle-labeled peptides have been specifically cleaved by an enzyme, Proteinase K, from a solid phase support. After washing and in the presence of the enhanced luminescence composition of U.S. Pat. No. 6,340,744, both the intact bead-bound peptide and the beads after enzymatic cleavage showed typical europium luminescence under UV excitation. However, the luminescence from the intact beads was strong and the luminescence from the beads after cleavage was weak. This strong luminescence demonstrated that significant amount of europium macrocycle had coupled to the peptide. The drastic difference in luminescence before and after Proteinase K hydrolysis demonstrated that the europium macrocycle-labeled part of the peptide had been released from the beads by hydrolysis.

Two Photon (Up-Conversion) Excitation of Lanthanide Luminescence

Solutions of neodymium ion, Nd(III), complexes have been recently reported (Xiao et al. Ref. 17.) to upconvert, emitting at wavelengths shorter than those employed for excitation. Since "For one color excitation the emitted light depends quadratically on the incident laser power", and the excitation wavelength was longer (590 nm) than the strongly emitted wavelengths, "located near 360 nm, 387 nm, and 417 nm" this evidently was two photon excitation. More efficient upconversion was observed with ethylenediaminetetraacetic acid (EDTA) than with dipicolinic acid (DPA), otherwise known as 2,6-pyridinedicarboxylic acid ($H_2PDCA$). These authors also studied the use of excitation by two lasers, one of which emitted between 592 and 599 nm and the other between 791 and 799 nm. The lifetime of the first excited state ($^4F_{3/2}$), produced by excitation near 800 nm, was much longer (55 to 684 ns) than the lifetime (less than 20 ns) of the emitting excited state ($^4D_{3/2}$) produced by excitation near 590 nm. The substitution of $D_2O$ for $H_2O$ reduced "the nonradiative transfer of the excited state energy of the rare earth ion to the high frequency O—H bond vibrations that exist in the $H_2O$ solution resulting in longer decay lifetimes and more efficiency."

In U.S. Pat. No. 5,698,397 (Zarling et al., Ref. 18), the definition of the label stated (Col. 10), "The label can alternatively comprise a lanthanide ion in a chelate or cage compound." In Table I (Col. 16), "various phosphor material compositions capable of up-conversion" are listed. They consist of a host material, an absorber ion, an emitter ion and the visible color of the emission.

In the section of U.S. Pat. No. 5,698,397, Evaluation of Up-converting Chelates (Col. 54), the patent teaches only the successful up-conversion of complexes that contain one species of lanthanide ion. They studied separately complexes of the single lanthanide ions, erbium(III) and neodymium(III), which "have been prepared with ethylenediaminetetraacetic acid (EDTA) and dipicolinic acid (DPA)." The patent states, "The erbium chelates were pumped using light near 793.5 nm from a Ti:sapphire laser (the excitation scheme of Macfarlane (1989) Appl. Phys. Lett 54: 2301). This approach produced upconversion but not satisfactorily, which we attribute to weak absorption for the first step due to the increase in linewidth in the chelate over the low temperature crystal used for the up-conversion laser." However, the 380 nm emission of the neodymium chelates, when they were excited in the visible at 580 nm, was obtained.

This patent teaches (Col. 30), "Energy transfer can be efficient in a crystalline host containing many rare earth ions, but not in a solution where the concentration of ions is low and the phonon structure is less constrained."

Another patent (Kardos et al., U.S. Pat. No. 6,159,686, Ref. 19) based on the same parent application states, "Rare earth chelates may be used as up-converting reporters through stepwise excitation such as shown in FIG. 5a, or in FIG. 5b (except that all levels would be in the same ion). Energy transfer from a sensitizer ion to an activator ion cannot be used in the case of a single rare earth ion." This statement is clearly contradicted by the content of the present patent.

Zarling et al. (U.S. Pat. No. 6,399,397, Ref. 18) have described the instrumentation necessary for upconversion, two photon excitation of phosphor particles. In their Experimental Examples, as demonstrated in their FIGS. 11 and 12, they observed up-conversion at a very low power density of 1,000 W/cm². Specifically, submicron particles Na(Y$_{0.80}$Yb$_{0.18}$Er$_{0.02}$)F$_4$ that had been coated with polycarboxylic acid, when excited at approximately 977 nm, emitted at 541 nm. These Authors stated that the "maximal phosphorescence appears at approximately 400 μsec. with a gradual decay to a lower, stable level of phosphorescence at about 1000 μsec."

Ligands

Two new types of luminescent lanthanide complexes have been synthesized recently by Raymond's group. The first type includes complexes (Ref. 20) of hydroxyisophthalamidylamide-based bidentate, tetradentate and higher polydentate ligands, containing a single lanthanide ion. Excitation between 350 to 360 nm produced strong emission from the europium and terbium complexes of the H22IAM ligand, which is the unfunctionalized tetradentate ligand. The second type of complexes (Ref. 21) was similarly based on ligands containing the salicylamidyl moiety. The U.S. Pat. No. 6,406,297 (Ref. 21) states that there was "one type of complex in solution"; and "the stability of this complex is low." The spectra were reported as taken in a nonaqueous solvent, acetonitrile.

Murthy and Suva (Ref. 22), herein incorporated by reference, have described ligands for europium and other lanthanide ions that form complexes with excitation maxima at wavelengths longer than 360 nm. These compounds included a β-diketone terminated at end with "a substituted aromatic, heterocyclic aromatic or substituted heterocyclic aromatic group;" and a second group "independently selected from monocyclic aryl groups, multi-cyclic aryl groups". More complex structures included a third group "selected from monocyclic aryl groups, multi-cyclic aryl groups". The peak excitation wavelengths of the europium ion complexes of their PNPD and NNPD compounds were 390 nm and 400 nm, respectively. US Patent Application 20040082768 (Ref. 22) also teaches that "it is possible to avoid hydration (of their complexes) with water molecules where one of the Aryl moieties is further substituted adjacent to the diketone substituent with an additional chelating moiety." In FIG. 4 of this patent, this moiety is shown as a methyl ester.

Jones, II, et al. U.S. Pat. No. 6,402,986 (Ref. 23), herein incorporated by reference, teaches chemical structures of ligands that form luminescent chelates with lanthanide ions, specifically europium and terbium ions. Four of these ligands were derived from 2,6-pyridinedicarboxylate and two were based upon terpyridinedicarboxylate. The proposed use of these chelates was to serve as taggants that when applied to multiple materials would provide "a multi-parameter signature for purposes of comparative light decay analysis of verification marks or features." The resistance to photodegeneration of these Eu(III) ligands by "intermittent sunlight filtered by common exterior glass light" was much higher than that of "europium complexes of the diketonate class encompassing, for example, the ligands, naphthoyltrifluoroacetonate and benzoyltrifluoroacetonate". The lifetimes of the Eu(III) and Tb(III) chelates of ligands 1 to 5 of U.S. Pat. No. 6,402,986 were all increased by imidazole and 4-methylimidazole, and iminodiacetic acid decreased the lifetimes of ligands 1 to 4. U.S. Pat. No. 6,402,986 describes the benefits of the use of poly(vinyl acetate) (PVA) with a molecular weight in the range of 10,000-500,000 KD: "Increases of 30-40 fold in luminescence intensity and lifetime are observed for ink compositions that include moderate concentrations of PVA (mM range)."

Lehn and coworkers have created functionalized cryptates which are macropolycyclic rare earth complexes (Refs 24, 25, 26) which have the advantages of a high quantum yield of fluorescence and a high molar absorption coefficient, stability, solubility in, and non-inhibition by water or other solvent or by molecules present in the medium in which the measurement. Cryptates are selectively chelated by lanthanides in solutions containing other cations.

Lehn and coworkers have created lanthanide(III) cryptates in which the lanthanide(III) ions are complexes within the three-dimensional cavity of functionalized macropolycyclic ligands termed cryptands (Refs 24, 25, 26) herein incorporated by reference. These lanthanide(III) cryptates have the advantages of a high quantum yield of luminescence, a high molar absorption coefficient, stability, solubility in water and other solvents, and resistance to decomposition or luminescence inhibition by water, other solvents, or molecules present in the medium in which the measurement is performed. The lanthanide ions are selectively complexed by cryptands in solutions containing other metal ions.

Other Lanthanide Ions

Hofstraat, US Application 20020187563 (Ref. 27) herein incorporated by reference, teaches ion-ligand complexes of the neodymium(III) ion, Nd(III), ytterbium(III) ion, Yb(III), or erbium(III) ion, Er(III), with derivatives of polyaminocarboxylic acids and pyridinedicarboxylic acid. These derivatives include sensitizing moieties derived from conventional organic fluorophores that absorb in the region of 400-1,000 nm. Excitation at 500 nm resulted in emissions from fluorexon complexes of Nd(III) (880, 1060, 1320 nm), Yb(III) (980 nm), and Er(III) (1530 nm). Both water and deuterium oxide were studied as solvents. The lifetimes of the DPTA-fluorescein and DPTA-eosin complexes of these lanthanide ions ranged from 1 to 0.5 μsec in D$_2$O and from 0.61 to 0.15 μsec in H$_2$O. These lifetimes are "about two orders of magnitude shorter than that of the prior art Eu(III) and Tb(III) complexes."

SUMMARY OF THE INVENTION

In accordance with the invention, there is provided a unitary luminescence enhancing solution that contains a solvent, an energy transfer donor and after drying in the presence of an energy transfer acceptor lanthanide ion complex results in a solid that enhances the luminescence of the energy transfer acceptor lanthanide ion complex by a mechanism other than completing the complexation of the lanthanide ion.

The energy transfer donor is at least one substance selected from the group consisting of a fluorophore, a lumiphore, or combination thereof. A fluorophore is a molecule or ion or complex capable of fluorescence, i.e. any process by which an electron of a molecule or ion that is in an electronic singlet state (a state in which the spins of all electrons are paired) absorbs the energy contained in one or more photons, with the result that this electron is elevated to a higher energy singlet state, and subsequently an electron of this molecule or ion loses energy in the form of a quantum of energy and deactivates to a lower energy state. This process does not involve a change in the electronic spin multiplicity of the molecule or ion. This quantum of energy can be in the form of an emission of a photon or transfer of energy to a neighboring molecule or ion. A lumiphore is a molecule or ion or complex capable of luminescence, i.e. any process by which an electron of a molecule or ion absorbs the energy contained in one or more photons, with the result that this electron is elevated to a higher energy singlet state, subsequently relaxes to a lower energy triplet state, and subsequently energy is lost from an electron of this molecule or ion in the form of a quantum of energy with the concurrent deactivation of this electron to a lower state. This process involve a change of the electronic spin multiplicity of the molecule or ion. This quantum of energy can be in the form of an emission of a photon or transfer of energy to a neighboring molecule or ion.

The solvent has an evaporation rate preferably at least equal to that of water. The amount of solvent is sufficient to afford a unitary solution.

In the unitary luminescence enhancing solution, the concentration of surfactant, when present, is less than the critical micellar concentration.

Also in accordance with this invention, there is provided a spectrofluorimetrically detectable solid luminescent composition consisting essentially of:

A spectrofluorimetrically detectable luminescent resonance energy transfer (from here on abbreviated RET) transparent solid composition consisting essentially of a processed specimen which includes at least one conjugate of a lanthanide ion complex and is embedded in a luminescence enhancing solid composition derived by removal of the solvent from the unitary luminescence enhancing solution. This labeled specimen containing composition consists of at least one energy transfer acceptor lanthanide ion complex having an emission spectrum with at least one maximum in the range from 300 to 2000 nanometers, and a luminescence-enhancing amount of at least one fluorophore and/or lumiphore energy transfer donor with the condition that the emission spectrum of the energy transfer donor differs from that of the energy transfer acceptor lanthanide ion complex.

The term "consisting essentially of" is used in its art-recognized sense to express that the composition is open to the inclusion of only such additional ingredients as do not adversely affect its essential properties as defined. Consequently, the presence of a surfactant in a concentration that, when the composition is liquid, is greater than the critical micelle concentration, is excluded, because surfactant in such concentration impairs the morphology of delicate objects, such as mammalian cells.

The enhanced luminescence of compositions according to the invention permits the detection and/or quantitation of the conjugates of lanthanide ion complexes with or without the use of time-gated detection systems. As a result, these lanthanide ion complexes are useful as optical-labels for analysis and quantitation. Areas of use include but are not limited to: immunoassays; genomics; proteomics; cytomics; analytical cytology; histological staining; arrays of nucleic acids, proteins, and tissue sections; and imaging processing. Accordingly, there is also provided, according to this invention, a method for analysis of an insoluble or insolubilized sample suspected of containing at least one analyte, frequently a biologically active compound, the method comprising the steps:

(a) Contacting the sample with a solution that contains an energy transfer acceptor lanthanide ion complex which is conjugated to an analyte-binding species. This conjugation to the analyte-binding species can be achieved either directly or indirectly through a bridging molecule, and/or by being a label of a labeled-polymer-conjugate of said member;

(b) Incubating the sample with the solution under binding conditions, whereby the member of the specific combining pair binds to the analyte;

(c) Usually washing the sample to remove the unbound conjugate of the member of a specific combining pair;

(d) Adding to the sample a unitary luminescence enhancing solution;

(e) Removing the solvent of the unitary luminescence enhancing solution to produce a homogeneous solid composition that includes both the energy transfer donor compound and the energy transfer acceptor complex;

(f) Subjecting the homogeneous solid composition to excitation energy in the range of 200-1500 nm, whereby enhanced luminescence in the range of 350-2000 nm is generated;

(g) Monitoring the luminescence of the homogeneous solid composition for at least one of the following:
  (1) presence and/or concentration and/or location of the energy transfer acceptor lanthanide ion complex; and
  (2) presence and/or concentration and/or location of the product of the interaction of the analyte with the energy transfer acceptor lanthanide ion complex which is conjugated to an analyte-binding species.

There is, moreover, provided a method for analysis of a first solution suspected of containing at least one analyte, frequently a biologically active compound, comprising the steps (a) Binding a member of a specific combining pair that is specific to an analyte to a receiving surface member;

(b) Washing the receiving surface member to remove any unbound member of a specific combining pair;

(c) Adding a first known volume of a first solution to a second known volume of a second solution that contains an energy transfer acceptor lanthanide ion complex which is conjugated to an analyte. This conjugation to the analyte can be achieved either directly or indirectly through a bridging molecule, and/or by being a label of a labeled-polymer-conjugate of the member;

(d) Incubating the combined solutions under binding conditions with the solid support, whereby the member of the specific combining pair binds to the analyte;

(e) Usually washing the solid support to remove the unbound analyte and analyte conjugate of the energy transfer acceptor lanthanide ion complex;

(f) Adding to the sample a unitary luminescence enhancing solution;

(g) Removing the solvent of the unitary luminescence enhancing solution to produce a homogeneous solid composition that includes both the energy transfer donor compound and the energy transfer acceptor complex;

(h) Subjecting the homogeneous solid composition to excitation energy in the range of 200-1500 nm, whereby enhanced luminescence in the range of 350-2000 nm is generated;

(i) Monitoring the luminescence of the homogeneous solid composition to measure the decrease in the emission intensity resulting from the competition of the unconjugated analyte with the conjugated analyte.

The unitary luminescence enhancing solutions according to the invention are conveniently termed unitary resonance energy transfer (RET), and when they include a complex of a second lanthanide ion, they are termed columinescence solutions. Such solutions can be directly integrated into standard histochemical and cytochemical processing. Such solutions can also be dried to afford solids which can be stored for desired periods, or they can be packaged initially as solids and later reconstituted as effective solutions by combination with solvent at the time of use.

The enhanced luminescence of the lanthanide ions and complexes thereof in the solid state, resulting from the use of either RET or its derivative, columinescence, solutions according to the invention, is believed to be caused by the absorption of one or more photons by an energy transfer donor.

and by the transfer of all or part of the absorbed energy to an energy transfer acceptor lanthanide ion complex that subsequently emits all or part of this energy as a photon, with the limitation that less than twenty percent of any light emitted by the energy transfer donor compound or ion overlaps in the wavelength with the light emitted by the lanthanide energy transfer acceptor complex.

In the Resonance Energy Transfer or its derivative, cofluorescence, of the invention, the energy transfer acceptor can be a functionalized derivative of an energy transfer acceptor lanthanide ion complex, that is, a complex substituted with reactive functional groups at which reaction with a member of a specific combining pair can take place; the energy transfer acceptor can also be a reaction product of such functionalized lanthanide ion complex with such analyte; or a polymer which contains one or more lanthanide-ion-containing complex units.

There is also provided, in accordance with this invention, a dry mixture consisting essentially of an energy transfer donor fluorophore or lumiphore, or a combination thereof; and an organic and/or biological material to which is linked through a reactive functionality an energy transfer acceptor lanthanide ion complex, provided that the lanthanide ion and a metal ion, if present in the donor, are not the same. Since this dry mixture is not diluted with one or more materials to an extent resulting in separation of the energy transfer donors from the energy acceptor lanthanide ion complex, the dried solids including the energy transfer donors act as the host material and provide the energy to the energy transfer acceptor. Since the energy transfer donor molecule, ion, and/or complex of the metal ion, while in solution, contacts and if necessary is given time to penetrate into organic and/or biological material before it is dried, the concentration of donor molecule, ion, and/or complex near the acceptor lanthanide ion complex can be much higher than that provided by a unitary solution. In the limiting case, the acceptor lanthanide ion complex is present at a minuscule concentration compared to that of the energy transfer donor.

It is a feature of this invention that the method does not require prior dissociation of the luminescence-enhanced complex before measuring its emission. Moreover, since the excitation spectra of lanthanide ion complexes and those of several DNA-specific fluorophores, including 4',6-diamidino-2-phenylindole (DAPI), occur in the same region of the ultraviolet, both types of compounds can be excited at the same wavelength, while their emission spectra occur in different regions. The organic fluorophores have broad emissions in the blue region of the spectrum with short lifetimes, whereas the enhanced luminescence of lanthanide ion complexes according to this invention occurs as very narrow emission peaks in the green, orange, red, and infrared region of the spectrum with long lifetimes. This difference allows the major emission of the enhanced luminescence composition of this invention to be unambiguously detected even when its intensity is much lower than that of the very strong emission of the DNA-specific or other organic fluorophores.

It is a further feature of the invention that the composition and method of the invention not only provide enhanced luminescence but also minimize the interfering effect of the non-specific binding of lanthanide macrocyclic complexes to substrates.

DETAILED DESCRIPTION OF THE INVENTION INCLUDING PREFERRED EMBODIMENTS

Description of Preferred Embodiments

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All patents and publications mentioned herein are incorporated herein by reference for the purpose of describing and disclosing, for example, the cell lines, constructs, and methodologies that are described in the patents and publications, which might be used in connection with the presently described invention. The patents and publications discussed throughout the text are provided solely for their disclosure prior to the filing date of the present application. Nothing herein is to be construed as an admission that the inventors are not entitled to antedate such disclosure by virtue of prior invention.

Acceptors

The energy transfer acceptor lanthanide complex ingredient of the composition of the invention is characterized by a luminescence spectrum with emission in the range from 300 to 2,000 nanometers and preferably from 350 to 1500 nanometers, following excitation in the range from 200 to 1800 nanometers and preferably from 200 to 1600 nanometers. This excitation can be from one or more photons.

When the energy transfer acceptor lanthanide complex ingredient of the composition of the invention is a macrocycle, it is characterized by kinetic stability even in very dilute aqueous solution. The complex is resistant to removal or exchange of the central metal and has counterions, or charge-balancing anions, readily exchangeable by other anions.

The macrocycle moiety of the lanthanide energy transfer acceptor macrocyclic complex has six coordinating atoms, of which at least 4 are nitrogen atoms, and the remainder are nitrogen, oxygen, or sulfur.

In particularly preferred compositions of the invention, the lanthanide energy transfer acceptor macrocyclic complex has the formula Formula III

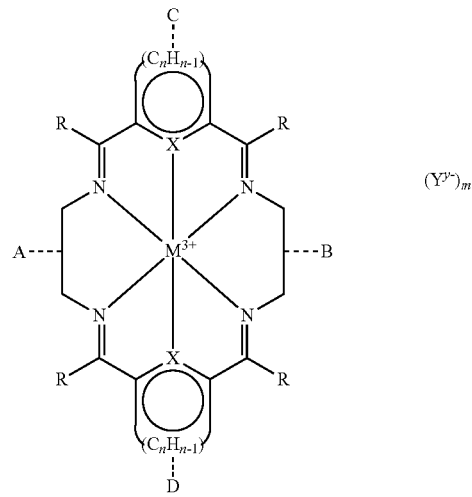

Wherein:
M is a metal ion selected from the group-consisting of a lanthanide having atomic number 57-71, an actinide having atomic number 89-103, and yttrium having atomic number 39;
R is a substituent selected from the group consisting of hydrogen, straight-chain alkyl or branched-chain alkyl; aryl-substitited alkyl, aryl, or alkyl-substituted aryl, with the proviso that such substituent does not limit the solubility of the resultant complex or otherwise interfere with the cyclization of such complex during its synthesis;

X is an atom selected from the group consisting of nitrogen, sulfur and oxygen; such atom forms a part of a ring structure selected from the group consisting of pyridine, thiophene or furan, respectively;

n is 2 or 3;

Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to luminescence;

m+ is the ionic charge of the metal ion in the macrocyclic complex, and;

y− is the ionic charge of the counterion in the macrocyclic complex.

A, B, C, and D are substituents selected from the group consisting of hydrogen, straight-chain alkyl or branched-chain alkyl; aryl-substituted alkyl, aryl, or alkyl-substituted aryl; reactive functionality, functionalized alkyl, functionalized aryl-substituted alkyl, functionalized aryl, or functionalized alkyl-substituted aryl. Straight chain and branched chain alkyl substituents at A, B, C, and/or D have from 1 to 25 carbon atoms. The reactive functionality is thereby spaced from the macrocycle as desired. Further illustrative functionalized substituents include hydroxymethyl, 4-hydroxybenzyl, 4-aminobenzyl, and 4-isothiocyanatobenzyl.

For convenience, the following abbreviations can be used to refer to compounds of Formula III.

Any and all of the metal ions selected from the group consisting of a lanthanide having atomic number 57-71, an actinide having atomic number 89-103, and yttrium having atomic number 39 will have M as their abbreviation. Specific metal ions will be given as their standard chemical symbols. The unfunctionalized, mono-functionalized and di-functionalized macrocyclic complexes will be abbreviated respectively as "Mac-un", "Mac-mono" and "Mac-di". The term "Macs" without the -un, -mono, or -di suffix will include the unfunctionalized, mono-functionalized and di-functionalized macrocyclic complexes (Mac-un, Mac-mono and Mac-di). When a specific peripheral pendant substituent having at least one reactive site (reactive functionality) is mentioned, its abbreviation will be given as a suffix. Thus the compound of Formula IV shown below, in which M is europium, each R is methyl (as shown by bond lines without termination) and each of A and B is a 4-isothiocyanatobenzyl group, is abbreviated as EuMac-di-NCS. The compound of Formula V shown below, in which M is terbium, each R is methyl, and B is a 4-isothiocyanatobenzyl group, is abbreviated as ThMac-mono-NCS, and the unfunctionalized compound of Formula VI shown below, in which M is europium, each R is methyl and each of A and B is hydrogen, is abbreviated as EuMac-un.

Formula IV

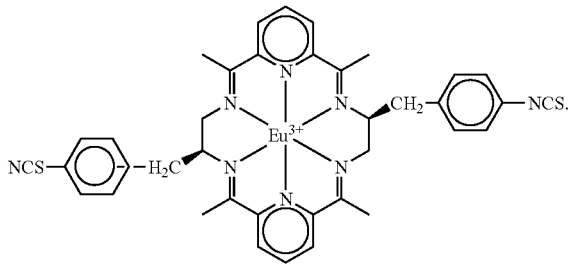

Schematic formula of a di-functionalized europium macrocyclic complex. This structure is one of the isomers of the cationic europium macrocyclic moiety containing a 4-isothiocyanato-benzyl-substituent on each of the aliphatic side-chains. The molecular formula of the moiety is $C_{38}H_{36}N_8S_2Eu$. This formula, and the following formulae that include methyl groups, adhere to the present convention of showing methyl groups as bond lines without termination.

Formula V

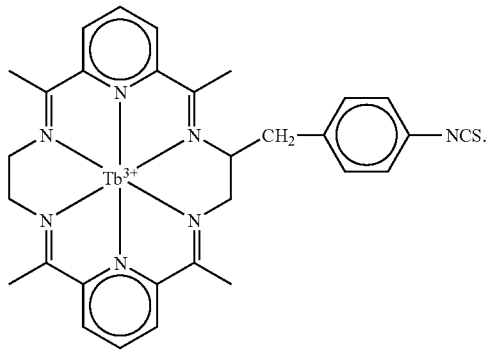

Schematic formula of a cationic mono-functionalized terbium macrocyclic complex containing a 4-isothiocyanato-benzyl-substituent on one of the aliphatic side-chains. The molecular formula of the moiety is $C_{30}H_{31}N_7STb$.

Formula VI

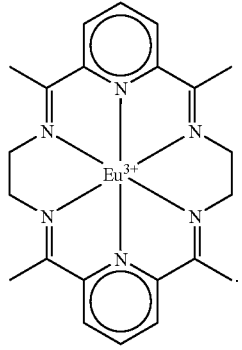

Schematic formula of a cationic unfunctionalized europium macrocyclic complex. This structure is the unfunctionalized prototype, EuMac-un.

For the synthesis of these lanthanide macrocycle complexes, including access to the required starting materials, reaction conditions, purification, and subsequent coupling reactions with compounds of biological interest, reference can be made to Vallarino et al., U.S. Pat. Nos. 5,373,093 and 5,696,240 herein incorporated by reference.

In a preferred group of compositions of this invention, at least one of the substituents A, B, C, and D of Formula III is a reactive functionality or a functionalized alkyl, functionalized aryl-substituted alkyl, functionalized aryl, or functionalized alkyl-substituted aryl group. Through these substituent groups, coupling or noncovalent binding can take place with an analyte, which can be a biologically active compound or any other compound able to interact with a functionalized substituent at A, B, C, and/or D.

Such coupling can take place directly, as in a conjugate of a LnMac with a protein or a polynucleotide linked to the LnMac through a functionalized group at A, B, C, or D.

Coupling of a functionalized group at A, B, C, or D with an analyte can also take place indirectly, by reaction between the functionalized group and a bridging/linking moiety that provides the capability for derivatization with a receptor molecule or with an entity for which there is a corresponding receptor molecule, together with controlled spacing of the substrate of biological interest relative to the macrocycle of Formula III. Thus coupling is accomplished indirectly, either by the use of a bifunctional crosslinking reagent that provides covalent binding to the substrate of biological interest, or by binding the macrocycle to another molecule that has a high affinity for the substrate. To illustrate, streptavidin can couple with a functionalized macrocycle as well as with biotin, thus providing a link between biotin and the LnMac. In another illustrative reaction, an amine-functionalized macrocyclic complex of Formula III is acylated with a reagent, such as succinic anhydride, to provide a carboxyl group which then readily either bind to the free amino groups of lysine in proteins, forming a protein/macrocycle conjugate or can through the known art (Ref. 28) be transformed into a different reactive functionality, such as a NHS ester.

The lanthanide macrocycle complexes with more than one reactive functionality, such as the EuMac-di-NCS, can be used as both labels cross-linking fixatives. They can be used to optically label and immobilize proteins and other macromolecules, including those present in gels after electrophoretic separation.

Other applications include fingerprint detection.

In a particularly preferred embodiment, a composition of the invention can include two different LnMacs energy transfer acceptors, both coupled to the same polynucleotide, or two different LnMacs energy transfer acceptors, each coupled to a different polynucleotide, having in each case luminescence enhanced according to the invention. When the two LnMacs differ in their central metal ion, as with an europium macrocycle and a samarium macrocycle, and hence differ in the wavelength of their emission peaks, the measurement of the intensity of each peak provides a measure of the concentration of each LnMac and, if both LnMacs are present, it also provides their relative ratios over a range from 500:1 to 1:500, more specifically over a range from 100:1 to 1:100.

An important application of the above effect is the measurement of relative concentrations of normal cell DNA and cancer cell DNA by coupling each of these to a different LnMac.

For further details of the coupling capabilities of functionalized macrocycles of Formula III, reference can be made to Vallarino et al. U.S. Pat. No. 5,696,240, at column 21 line 52 to column 22 line 42, here incorporated by reference.

When a functionalized macrocycle of Formula III is coupled directly or through a bridging/linking moiety to a reactive biomolecule, the resulting conjugate has the formula Formula VII

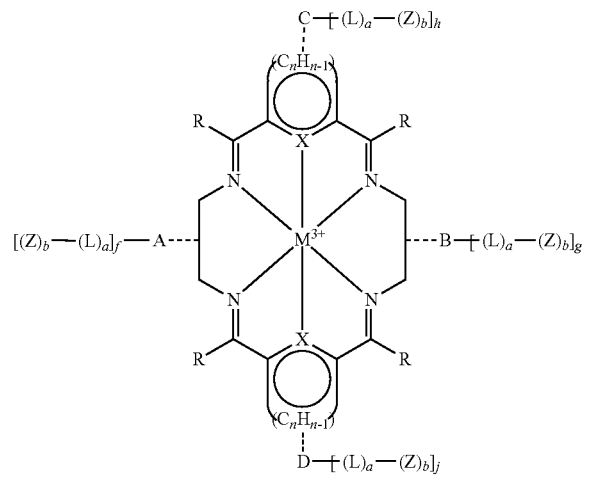

in which M, X, R, and n are as defined above; from one to two of A, B, C, and D are functionalized groups as defined above, and the remaining groups of A, B, C, and D are selected from the group consisting of hydrogen, straight-chain alkyl, branched-chain alkyl, aryl-substituted alkyl, aryl, and alkyl-substituted aryl; L is a bridging/linking moiety between the functionalized macrocycle and a biologically active compound, Z is a residue of a biologically active compound linked to L, a is zero or one, b is one, and each of f, g, h, and j is independently zero or one, provided that the sum of f, g, h, and j is either one or two.

When a functionalized macrocycle of Formula III is coupled to a bridging/linking moiety with the capability of further reacting with an analyte to form a conjugate, the resulting complex has Formula VII in which L is a bridging/linking moiety capable of coupling the functionalized macrocycle and the analyte, a is one and b is zero, and M, X, R, n, A, B, C, D, f, g, h, and j are as defined above.

As a result of the ability of analytes including reactive biomolecules to form a covalent bond with a functionalized macrocycle in a composition of this invention, as expressed by Z in Formula VII, the enhanced luminescence of the composition can serve as an analytical tool for estimating such biomolecules as analytes. Thus the analyte can be any compound of interest, naturally occurring or synthetic, for which there exists a complementary binding partner.

These analytes are conveniently grouped by molecular weights. One group of such analytes consists of compounds that have molecular weights in the range of about 125-2,000 daltons and include a wide variety of substances, which are often referred to as haptens. These compounds include:
(a) Vitamins, vitamin precursors, and vitamin metabolites including retinol, vitamin K, cobalamin, biotin, folate;
(b) Hormones and related compounds including
(i) steroid hormones including estrogen, corticosterone, testosterone, ecdysone,
(ii) aminoacid derived hormones including thyroxin, epinephrine,
(iii) prostaglandins,
(iv) peptide hormones including oxytocin, somatostatin;
(c) Pharmaceuticals including aspirin, penicillin, hydrochlorothiazide;
(d) Nucleic acid constituents including
(i) natural and synthetic nucleic acid bases including cytosine, thymine, adenine, guanine, uracil, derivatives of said bases including 5-bromouracil,
(ii) natural and synthetic nucleosides and deoxynucleosides including 2-deoxyadenosine, 2-deoxycytidine, 2-deoxythymidine, 2-deoxyguanosine, 5-bromo-2-deoxyuridine, adenosine, cytidine, uridine, guanosine, 5-bromo-uridine,
(iii) natural and synthetic nucleotides including the mono, di, and triphosphates of 2-deoxyadenosine, 2-deoxycytidine, 2-deoxythymidine, 2-deoxyguanosine, 5-bromo-2-deoxyuridine, adenosine, cytidine, uridine, guanosine, 5-bromouridine;
(e) Drugs of abuse including cocaine, tetrahydrocannabinol,
(f) Histological stains including fluorescein, DAPI;
(g) Pesticides including digitoxin;
(h) Miscellaneous haptens including diphenylhydantoin, quinidine, RDX.

Another group of analytes consists of compounds having a molecular weight of 2,000 daltons or more, including
(a) Proteins and their combinations including
(i) albumins, globulins, hemoglobin, staphylococcal protein A, alpha-fetoprotein, retinol-binding protein, avidin, streptavidin, C-reactive protein, collagen, keratin,
(ii) immunoglobulins including IgG, IgM, IgA, IgE,
(iii) hormones including lymphokines, follicle stimulating hormone, and thyroid stimulating hormone,
(iv) enzymes including trypsin, pepsin, reverse transcriptases, terminaldeoxytransferase,
(v) cell surface antigens on T- and B-lymphocytes, i.e. CD-4, CD-8, CD-20 proteins, and the leukocyte cell surface antigens, such as described in the presently employed CD nomenclature,
(vi) blood group antigens including A, B and Rh,
(vii) major histocompatibility antigens both of class 1 and class 2,
(viii) hormone receptors including estrogen receptor, progesterone receptor, and glucocorticoid receptor,
(ix) cell cycle associated proteins including protein kinases, cyclins, PCNA, p53,
(x) antigens associated with cancer diagnosis and therapy including BRCA(s) carcinoembryonic antigen, HPV 16, HPV 18, MDR, c-neu; tumor suppressor proteins, p53 and retinalblastoma,
(xi) apoptosis related markers including annexin V, bak, bcl-2, fas caspases, nuclear matrix protein, cytochrome c, nucleosorne,
(xii) toxins including cholera toxin, diphtheria toxin, and botulinum toxin, snake venom toxins, tetrodotoxin, saxitoxin,
(xiii) lectins including concanavalin, wheat germ agglutinin, soy bean agglutinin;
(b) Polysialic acids including chitin;
(c) Polynucleotides including
(i) RNAs including segments of the HIV genome, human hemoglobin A messenger RNA,
(ii) DNAs including chromosome specific sequences, centromeres, telomere specific sequences, single copy sequences from normal tissues, single copy sequences from tumors.

The biomolecule to be coupled to the macrocyclic complex for imaging or therapy is typically a species selected to carry out a specific target function. In one embodiment, the biomolecule is a monoclonal antibody or antibody fragment which is specific against a selected cell-surface target site. Such antibodies are commercially available, or are made by well-known techniques.

In a preferred embodiment, the lanthanide(III) of the energy transfer acceptor macrocyclic complex is europium, samarium, or terbium. In a particularly preferred embodiment, a composition of the invention includes an energy transfer acceptor macrocyclic complex in which the central ion is europium, a second energy transfer acceptor macrocyclic complex in which the central ion is terbium, and a third energy transfer acceptor macrocyclic complex in which the central ion is samarium. The characteristic emission peaks of the europium, terbium and samarium ions are sufficiently separated in the spectrum, so that the emission intensities of the three macrocyclic complexes can be measured in the presence of one another. As a result, three different biomolecules can be measured in the presence of one another by using an enhanced luminescence composition of the invention, whereby one biomolecule is coupled to a functionalized europium macrocycle, a second biomolecule is coupled to a functionalized terbium macrocycle, and a third is coupled to a functionalized samarium macrocycle.

Donors

The energy transfer donor transfers energy to the energy acceptor lanthanide complex. In a preferred embodiment, this donor can be a fluorophore and/or lumiphore organic moiety which upon excitation by a photon transfers energy to the lanthanide complex. An example of this is HTTFA when present in molecular concentration excess relative to the energy acceptor lanthanide complex. Alternatively, the energy transfer donor is a fluorophore and/or lumiphore ligand capable of being bound to a lanthanide metal ion or alternatively a fluorophore and/or lumiphore ligand bound to a lanthanide metal ion, or a mixture thereof. These ligands are characterized by electron donating atoms, such as oxygen, nitrogen, sulfur or phosphorus, and are able to coordinate with the energy acceptor lanthanide(III) or with energy donor gadolinium(III) or yttrium(III) ions. Preferred unbound or nonbinding fluorophore and/or lumiphore species include HTTFA or any other nonbinding species that has an extinction coefficient above 5,000 at a wavelength between 200-800 nm for single photon excitation, and twice those wavelengths (400-1600 nm) for two photon excitation.

Examples of fluorophore and/or lumiphore donors include HTTFA and $H_2$PDCA and the anions TTFA, Formula VIII, and PDCA, Formula IX, resulting from deprotoriation of these molecules. Alternatively the fluorophore and/or lumiphore energy transfer donor can be a ligand complex that includes a lanthanide(III). Examples of this are Gd(TTFA)$_3$ and Na$_3$Gd(PDCA)$_3$.

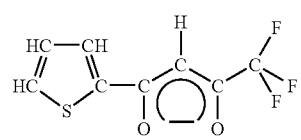

Formula VIII

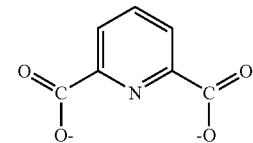

Formula IX

Non-limiting examples of energy transfer donors are the fluorophore and/or lumiphore ligands or anions formed in an acid-accepting environment by deprotonation of diketones, monocarboxylic and dicarboxylic acids and their esters, ortho-hydroxy-substituted aromatic carboxylic acids in which the oxygen atoms are positioned so as to favor homogeneous resonance energy transfer to the ligands that can form a chelate ring structure with the acceptor metal ion, and heterocyclic mono- and di-carboxylic acids in which the oxygen atoms of the carboxylate group and the heteroatom of the cyclic structure are positioned so as to favor formation of a chelate ring structure with the acceptor metal ion. Other non-limiting examples of energy transfer donors are the acids of these anionic ligands, having emissions that overlap the excitation of the energy acceptor lanthanide complex. Other non-limiting examples of energy transfer donors are the complexes of these ligands with metal ions. Preferably, these fluorophore and/or lumiphore donor metal ions are selected from the group of Gd(III), Y(III), Lu(III), and La(III). Alternatively under excitation which does not result in their emission, any of the acceptor lanthanide ions Eu(III), Sm(III), Tb(III) or Dy(III) can be employed. More preferably Eu(III) and Tb(III) can be employed.

The substitution of fluorine for hydrogen in the ligand further enhances the latter's effectiveness and removes a hydrogen atom that possibly could participate in loss of luminescence by radiationless vibrational transfer of the energy responsible for the luminescence to the surrounding solvent.

When the fluorophore and/or lumiphore ligand is a diketone, preferred ligand structures have the formula RCX(CHR')$_n$CXR'', in which:

R or R' or R'', independently at each occurrence, is an electron withdrawing group such as a hydroxy, an alkyl, a carbocyclic aromatic or heterocyclic aromatic group, a fluoroalkyl, fluoroalkylaryl, fluoroaryl, or fluoro-substituted heterocyclic aromatic group having 1 to 24 carbon atoms or R' is a hydrogen;

The concentration of these compounds or their anions, when present in the unitary luminescence enhancing solution, can range from $1\times10^{-1}$ to $1\times10^{-5}$ moles/L.

Preferred fluorophore and/or lumiphore beta-diketones have the formula RCOCH$_2$COR' in which R or R' are a alkyl, fluoroalkyl, fuoroalkylaryl, or fluoroaryl, a carbocyclic or heterocyclic aromatic group having 1 to 11 carbon atoms. Particularly preferred beta-diketones are thenoyltrifluoroacetone and hexafluoroacetylacetone. The concentration the of beta-diketone, when present in the unitary luminescence enhancing solution, can range from $1\times10^{-2}$ to $1\times10^{-5}$ moles/L.

Preferred fluorophore and/or lumiphore carboxylic acids include phthalic acid, furan-2-carboxylic acid, thiophene-2-carboxylic acid, pyridine-2-carboxylic acid (picolinic acid), furan-2,5-dicarboxylic acid, thiophene-2,5-dicarboxylic acid, pyridine-2,6-dicarboxylic acid and their lower alkyl esters, or any other carboxylic acid that has an extinction coefficient above 5,000 at a wavelength between 200-800 nm for single photon excitation, and at twice those wavelengths (400-1,600 nm) for two photon excitation.

Preferred fluorophore and/or lumiphore hydroxy-substituted aromatic carboxylic acids include salicylic acid and 2-hydroxynaphthalene-3-carboxylic acid.

Accordingly, the composition of the invention produces enhanced luminescence by the interaction in the solid state of an energy transfer acceptor lanthanide(III) macrocycle complex, as defined above, with a luminescence-enhancing amount of at least one fluorophore and/or lumiphore energy transfer donor. When the donor is an organic multidentate ligand, it can be combined in an acid-accepting environment with a metal ion to form a simple salt or a complex. The metal ion can be yttrium(III) or a 3-valent lanthanide having atomic number 59-71, preferably yttrium, lanthanum, or gadolinium. The metal ion, together with the atoms of the organic multidentate ligand to which it is coordinated, constitutes one or more five or six membered chelate ring structures.

The acid-accepting environment can be provided by any convenient inorganic or organic base such as an alkali metal base, an amine base, or a quaternary ammonium base. Suitable bases include potassium hydroxide, potassium bicarbonate, triethylamine, triethanolamine, tetraethylammonium hydroxide, and ammonia.

The organic multidentate ligand in an acid-accepting environment can also be provided as separate ingredients of the composition of the invention, such as the ligand admixed with an organic or inorganic base in stoichiometric, excess (super-stoichiometric) or deficient (sub-stoichiometric) molecular proportions.

The energy transfer donor is soluble in a solvent affording a unitary solution with the other components of the composition of the invention, as more fully defined below. The solvent is preferably an alcohol, more preferably ethanol.

The fluorophore and/or lumiphore energy transfer donor in the composition is present in a molecular concentration greater than that of the energy transfer acceptor complex. The concentration of the energy transfer donor in the unitary luminescence enhancing solution of the invention can range from $1\times10^{-1}$ to $1\times10^{-5}$ moles/L.

In a preferred composition according to the invention, the fluorophore and/or lumiphore energy transfer donor compound is an ionic compound of, or a complex of, gadolinium (III) or yttrium(III). The gadolinium(III) or yttrium(III) complexes with organic multidentate ligands are particularly preferred.

Solvent

As a liquid, the composition of the invention includes a solvent in an amount sufficient to dissolve all the components forming a unitary solution of such concentration that after evaporation the presence of the original solutes will increase the luminescence of the energy transfer acceptor lanthanide (III) complex. The solvent has an evaporation rate at least as great as that of water, to assure the ability to remove the solvent without special equipment and to obtain a dry composition containing a modest level of residual solvent that does not interfere with the luminescence of the composition, preferably less than 10% by weight, more preferably less than 1% by weight.

Suitable organic solvents include acetone, aliphatic alcohols having 1 to 3 carbon atoms, ethers such as 1,2-dimethoxyethane and 1,4-dioxane, and mixtures thereof. Methanol and ethanol are particularly preferred. Water can also be used as a solvent. The choice of solvent depends on maintenance of the desired physical characteristics of the specimen after evaporation. These include but are not limited to the morphology of microscopic objects and to the physical distribution of the enhanced luminescence ingredients on the surface of a support used in a measurement process.

Other Ingredients

The composition of the invention can include a buffer to maintain the pH within a desired range. Frequently used and preferred buffers include tris(hydroxymethyl)aminomethane, hexamethylenetetramine, and less preferred buffers include sodium and potassium bicarbonates.

The composition of the invention can include a high boiling liquid as an auxiliary solvent used in small amounts to assist in the conversion of the composition to the dry state without harmful effect. Such auxiliary solvents include toluene, xylene, pyridine, and polyethylene glycols such as PEG 1450.

The composition of the invention can include one or more solids to enhance the luminescence and/or maintain the desired physical and optical characteristics of the specimen after evaporation. Auxiliary solids that maintain the desired physical and optical characteristics by being crystallization inhibitors, and/or film formers, or binders include bovine serum albumin, polyvinyl alcohol, polyvinylpyrrolidone, solid polyethylene glycols, and plasticizers. Auxiliary solids that enhance the luminescence by being synergistic ligands include trioctylphosphine oxide and 1,10-phenanthroline.

In a preferred embodiment, the invention can include coatings that are applied subsequent to the formation of the homogeneous solid composition. These coatings include any transparent material that will transmit the excitation wavelengths and the emission wavelengths. These coatings should not dissolve an amount of any component of the unitary luminescence enhancing solution sufficient to make a significant reduction in the luminescence. In the case of analyses that involve imaging, the refractive index of the coating shall be sufficiently close to the refractive index of the specimen composition as to not significantly lower the optical resolution. These coatings include commercial dried mounting media, such as Clearium and solutions in organic solvents of plastics such as cyclo-olefins and acrylic polymers.

Functionalized Acceptor

The reaction medium in which a sample containing or suspected of containing an analyte is contacted with a functionalized complex according to this invention is preferably an aqueous solution in which the presence of foreign materials such as salts or organic solvents is limited to such concentrations as are tolerated by the analyte without denaturation, degradation, coagulation, hydrolysis, polymerization or other interfering changes. Binding conditions include such conditions of temperature, pressure, and pH as favor the reaction of the analyte with the functionalized macrocyclic complex, preferably a temperature in the range from 10° C. to 45° C., a pressure in the range from 800 to 1000 millibars, and in solutions where pH can be accurately measured, a pH in the range from 5.5 to 8.5.

The functionalized metal ion complex according the method of the invention is characterized by kinetic stability even in very dilute aqueous solution. The complex is resistant to removal or exchange of the central metal ion, and has counterions or balancing anions. Preferably the central metal ion is a lanthanide ion; and preferably the ligand of the complex is a macrocycle or a cryptate.

Support and Containers

The solid composition of the invention is preferably obtained by evaporation of a unitary solution of the energy transfer donor, solvent, and any other required components thereof. Evaporation suitably takes place in the presence of a support functioning as a container and/or vessel for the production of enhanced luminescence in the amount required for monitoring and measurement according to this invention. Suitable supports and containers include receiving surface members, such as microscope slides, cover-slips, and optical films or ribbons; microtiter wells; microtiter plates or strips; centrifuge tubes; test tubes; cuvettes; plated surfaces; and embossed surfaces.

In a preferred embodiment, the supports and containers are coated with one or more members from specific combining pairs that bind to an analyte or analyte-binding species. These coating include but are not limited to biotin, antibodies, nucleic acids, haptens, and polysaccharides.

Using Enhanced Luminescence Compositions in Analysis of Conjugates of Lanthanide Ion Complexes In analyzing in accordance with the invention, a processed specimen containing or suspected of containing an analyte is contacted with a solution that contains an energy transfer acceptor lanthanide(III) complex that is conjugated to an analyte-binding species in preferably an aqueous solution in which the presence of foreign materials, such as salts or organic solvents, is limited to such concentrations as are tolerated by the analyte under binding conditions without denaturation, degradation, coagulation, hydrolysis, polymerization or other interfering changes. Binding conditions include such conditions of temperature, pressure, and pH as favor the reaction of the analyte with the functionalized macrocyclic complex, preferably a temperature in the range from 10° C. to 45° C., a pressure in the range from 800 to 1000 millibars, a pH in the range from 5.5 to 8.5.

The functionalized energy transfer acceptor lanthanide(III) complex according to the invention is characterized by kinetic stability even in very dilute aqueous solution. The complex is resistant to removal or exchange of the central lanthanide(III), and has counterions or balancing anions readily exchanged for other anions. A detailed description of energy transfer acceptor lanthanide(III) complexes is given above in the description of the Acceptors section of the Prior Art. Preferably the ligands of the complex are fuctionalized macrocycles (Refs. 1,2) or functionalized cryptands (Refs. 24,25,26) particularly preferably are the functionalized macrocycles of U.S. Pat. Nos. 5,373,093 and 5,696,240.

The lanthanide(III), Ln(III), labeled processed specimen is then washed with a buffered aqueous solution to remove the excess of the conjugate of the energy transfer acceptor lanthanide(III) complex and prepared for treatment with the unitary luminescence enhancing solution. This treatment consists of optional air drying and optional transfer to the solvent of the unitary luminescence enhancing solution. For delicate material, such as mammalian cells, this transfer often involves a series of washes of a graded mixture of water with or without buffer and the solvent of the unitary luminescence enhancing solution.

The treated Ln(III)-labeled processed specimen is then reacted with "unitary luminescence enhancing solution, which after evaporation of the solvent results in the specimen containing composition, which is composed of the processed specimen embedded in the luminescence enhancing solid. Preferably the specimen containing composition is a transparent thin film on a support or container.

Instrumentation

A variety of instruments is commercially available according to this invention for monitoring the presence and/or concentration of the conjugate of a functionalized macrocyclic metal complex with an analyte; the presence and/or concentration of the product of the interaction of a functionalized macrocyclic metal complex with a binding material; and the presence and/or concentration of the product of the interaction of the conjugate with the binding material.

Time-gated fluorescence instrumentation can be used according to this invention; fluorescence instrumentation equipped with a continuous as opposed to pulsed light source can now also be used as a result of this invention. Such instrumentation can include: a standard manual or automated fluorescence microscope, a standard manual or automated fluorometer for reading samples including but not limited to discrete wells, microtiter trays and strips, arrays on microscope slides or other similar surfaces, and dipsticks. Also suitable is fluorescence instrumentation that measures multiple samples at a time, having a luminescence detection zone in which multiple samples can be automatically positioned. Such instrumentation can include a microtiter plate, strip, or microscope slide positioning system.

In a particularly preferred type of fluorescence instrumentation, the instrument includes the capability to image the sample being analyzed, and especially to measure the analyte at various points in the image. This can be accomplished in particular as the instrument measures, records, processes, and/or displays the spatial distribution of one or more analytes. Instrumentation with these capabilities include: the EIDAQ 100-H™ manufactured by Q3DM 10110 Sorrento Valley Road, Suite B, San Diego, Calif. 92121; the Chromoscan manufactured by Applied Imaging Corporation 2380 Walsh Avenue, Santa Clara, Calif. 95051, and the Axioplan 2 imaging manufactured by Carl Zeiss, Inc. One Zeiss Drive Thornwood, N.Y. 10594.

Among the preferred time-gated and/or continuous light source fluorescence instruments of these types can be mentioned a Varian Cary Eclipse spectrofluorometer (121 Hartwell Avenue, Lexington, Mass. 02421), an Ocean Optics USB2000-FLG Spectrofluorometer (380 Main Street, Dunedin, Fla. 34698), and a Jobin Yvon Inc. Fluorolog®-3 (3880 Park Avenue, Edison, N.J. 08820-3097).

Particularly preferred applications of the method include comparative genomic hybridization and measurement of one or more samples for an analyte on a microarray.

In an important feature of the method of the invention, the enhanced luminescence composition of the invention is formed in a dry state by evaporation of the solvent from a preformed unitary solution.

The following examples of compositions characterized by the use of energy transfer acceptor lanthanide complexes that are resistant to removal or exchange of the central metal ion, and of the use of said compositions, together with the use of unitary luminescence enhancing solutions and energy transfer donor complexes, are provided by way of illustration and not of limitation of the invention, whose scope is defined by the appended claims.

BRIEF DESCRIPTION OF THE DRAWINGS

FIG. 1 shows inverted images of the wells of a microtiter plate.

FIG. 2 shows inverted images of the wells of a microtiter plate.

FIG. 3 shows inverted images of the wells of a microtiter plate.

FIG. 4 is a graphical presentation of the ultraviolet absorption spectra of the EuMac-mono-NCS, streptavidin, and the EuMac coupled to streptavidin.

FIG. 5 is a graph of the relative emission intensity versus the concentration of streptavidin added to the biotinylated well.

FIG. 6 is a plot the concentrations of $Gd(TTFA)_3$ and HTTFA vs. relative luminescence.

FIG. 7 is a plot of the concentrations of $Gd(TTFA)_3$, Na(TTFA), and their one-to-one mixture vs. relative luminescence.

FIG. 8 is a plot of the concentrations of $Gd(TTFA)_3$, Na(TTFA), HTTFA, and their mixtures vs. relative luminescence.

FIG. 9a is a graph showing the effect of differing concentrations of $Na_2(PDCA)$ on the luminescence of two different lanthanide macrocycles.

FIG. 9b is a graph showing the effect of differing concentrations of $Na_3Gd(PDCA)_3$ on the luminescence of two different lanthanide macrocycles.

FIG. 10 is a graphical presentation of the ultraviolet absorption spectra of the EuMac-mono-NCS, anti-5-BrdU, and the EuMac coupled to anti-5-BrdU.

FIG. 11 is a pair of inverted images of EuMac-di-NCS stained cells. A is a 5 second exposure; B is the summation of 1000 time-gated images, each exposed for 2 msec.

FIG. 12 shows four images of a single preparation of non-apoptotic cells stained with both EuMac-di-NCS and DAPI.

FIG. 13 shows two inverted images of cells stained with SmMac-di-NCS and DAPI.

FIG. 14 is an inverted image of directly stained apoptotic cells.

FIG. 15 is an inverted image of EuMac-anti-5-BrdU stained cells in S phase.

FIG. 16 is an inverted image of EuMac-Streptavidin stained apoptotic cells.

FIG. 17 is an inverted image of EuMac-Streptavidin stained cells in S phase.

FIG. 18 is an inverted image of two photon excited EuMac-di-NCS stained cells.

SUMMARY OF EQUIPMENT, INSTRUMENTS, GENERAL PROCEDURES AND MATERIALS

Equipment, Instruments and General Procedures

Fluorometer-Luminometer

The emission and excitation spectra of the solids were obtained with a Varian Cary Eclipse spectrofluorometer equipped with a microplate reader accessory (Part No. 0010075300, Varian Associates, Walnut Creek Calif.)). The instrument was operated in time-gated mode. The slits and other settings of the Cary instrument were varied as required. All experiments and measurements were performed at ambient temperature unless stated otherwise.

Microscope

A Leitz MPV II fluorescence microscope equipped with a 10×0.25 NA, a 40×0.65 NA, and an infinity corrected objective high ultraviolet transmission UPL Fluorite 60 oil NA 1.25 with aperture (Olympus Part No. IUB532) objective, was employed to observe and to electronically photograph the cells. UV and blue illumination was provided by either a 100 watt Mercury-Xenon short arc or a Hamamatsu (Bridgewater, N.J.) L4634 flashlamp. The UV fluorescence was excited at 365 nm and the emitted light was observed through an Omega Optical (Brattleboro, Vt.) PloemoPak cube, UV DAPI, equipped with the following: a 365 nm narrow-band-width excitation filter (Omega 365HT25) and a 400 nm Beamsplitter (Omega 400DCLP02). The CCD optical path was optionally equipped with either a 619 nm narrow-band, 5.6 nm width at half maximum, emission filter (Omega 618.6NB5.6) or a standard DAPI 450 nm emission filter (Omega 450DF65). The SFX (fluorescein) stained cells were observed with a standard fluorescein Omega Optical Ploemo-Pak cube (Omega XF100/B/XC120 Vivid). The images were obtained with a peltier cooled, monochrome Quantitative Imaging Corp. (Burnaby, BC, Canada) Retiga-1350 EX, 12 bit ADC, CCD camera (1280×1024). According to the manufacturer's specification, this camera operates at 25° C. below ambient temperature, or ca. 0° C. The gray levels of the images were inverted for display. Darkness indicates strong luminescence.

An assembly (Ref. 13) was created to mount the flashlamp to the present Leitz MPV II microscope. The lamp mount is capable of movement in the X, Y, and Z directions. An auxiliary antireflection coated 100 mm focal length symmetric-convex synthetic fused-silica lens was inserted into the auxiliary filter holder of the epi-illumination system to decrease the optical path between the flashlamp and the rear of the objective.

The Retiga-1350 EX was strobed by a special time-delay box, which was provided by Quantitative Imaging Corp. Both the time-delay box and the flashlamp were connected directly to the pulse generator. When operated in preset number of images mode, the Retiga-1350 EX QCapture Software 1394 was set "edge high" (leading edge triggered).

When the above mentioned fluorescence microscope is used with the flashlamp, it will be referred to as the flashlamp microscope. The flashlamp microscope can operate in two modes. In one mode, when the flashlamp is continuously fired and the camera is continuously exposed, the results are essentially the same as those obtained with the mercury arc except that the exposures must be longer because of the lower average ultraviolet emission produced by the flash lamp. The second mode is time-gated. In this case, the CCD camera is only exposed subsequent to the ignition of the flashlamp. In this time-gated mode, the delay can be adjusted to eliminate the fluorescence emissions from conventional organic fluorochromes and many cellular components.

An Ultraviolet Products (UVP) (Upland, Calif.) Epi Chem II Darkroom was equipped with a 619 nm narrow-band, 5.6 nm half-width, emission filter (Omega 618.6NB5.6) and a special adaptor to mount the Retiga-1350 EX camera.

Image Manipulation

The TIFF images produced by the Retiga-1350 EX camera were manipulated with Adobe® (San Jose, Calif.) Photoshop® 7.0. All images were transformed into 8 bit gray and inverted to facilitate visualization. The conversion of a white image on a black background to a black image on a white background produces the equivalent of a conventionally stained absorbance image. The training of practitioners in the field of cytology, such as cytotechnologists and pathologists, is with absorbance images. Other manipulations of 8 or 16 bit images were performed with Fovea (Reindeer Games, Inc. Asheville, N.C.).

Most Commonly Used Materials

The vendors' addresses are given only in the description of their first product.
- (a) Tris(hydroxymethyl)aminomethane (TRIS), Ultra Pure Grade (Ameresco, Solon, Ohio, Catalog No. 0497-1 Kg).
- (b) Dimethylsulfoxide (DMSO), ACS Reagent, spectrophotometric grade (Aldrich, St. Louis, Mo., Catalog No. 15,493-9 (1996-97).
- (c) Triton X-100 (J. T. Baker, Phillipsburg, N.J., Catalog No. X198-07).
- (d) Knox Original Gelatin, Unflavored (Parsippany, N.J.).
- (e) EuMac-di-NCS was prepared according to U.S. Pat. No. 5,696,240, EXAMPLE XXIX B, step 1.
- (f) EuMac-mono-NCS was synthesized according to the procedures of Examples IX and XXXV, Step 1, of U.S. Pat. No. 5,696,240. The material used for the synthesis of the EuMac-mono-NCS from the EuMac-monoamine included: 34% EuMac-mono-amine, 66% unfunctionalized EuMac, and virtually no EuMac-diamine. Thus, in the final product the contamination by the cross-linking di-isothiocyanate was minimal. The unfunctionalized macrocycle contaminant should only act as a diluting, inert species.
- (g) 4,4,4-trifluoro-1-(2-thienyl)-1,3-butanedione (Thenoyltrifluoroacetone, HTTFA), 99% (Aldrich, Catalog No. T27006). The commercially obtained product was recrystallized twice from chloroform/diethylether/hexane using activated charcoal as decolorizing agent, dried in vacuo, and stored at 4° C. in a dark glass container.
- (h) 2,6-pyridinedicarboxylic acid, $C_7H_5O_4N$ ($H_2PDCA$), (Aldrich Chemical Co., St. Louis, Mo., Catalog No. P.6, 380-8).
- (i) High purity Gd(II)trichloride hydrate, $GdCl_3 \cdot n(H_2O)$, was prepared from the oxide, $Gd_2O_3$ 99.999% REO (Alpha Aesar, Ward Hill, Mass., Catalog No. 11289 (1999-2000), by dissolving it in 15% aqueous HCl, followed by evaporation to dryness with mild heating under reduced pressure.
- (j) Sodium azide, $NaN_3$ (Sigma, St. Louis, Mo., Catalog No. S-2002).
- (k) Hydroxylamine hydrochloride, $NH_2OH \cdot HCl$, (Sigma Catalog No. H9876).
- (l) The 1.5 M $NH_2OH \cdot HCl$ (pH8.5) solution is a 1.5 M $NH_2OH \cdot HCl$ aqueous solution that has been adjusted to pH 8.5 with NaOH.
- (m) 10×TBS-Azide is a solution (aqueous concentrate) that contains in 1 liter: 100 mMols of TRIS, 1.50 Mols of NaCl, and 77.0 mmol of $NaN_3$; the pH is adjusted to 7.4 with 12N HCl.
- (n) The TBS-Azide is an aqueous solution which contains in 1 liter: 10 mMols of TRIS, 150 mMols of NaCl, and 7.7 mMols of $NaN_3$. This solution is prepared by mixing one part 10×TBS-Azide with 9 parts water and adjusting the pH to 7.4 with 12N HCl and 1N HCl.
- (o) PEG 1,450, polyethylene glycol with average mol. wt. 1,450 (Sigma, Catalog No. P-5402).
- (p) 5% PEG-EtOH is an ethanolic solution which contains in 1 liter 50 grams of PEG 1,450.
- (q) 4',6-Diamidino-2-phenylindole dihydrochloride, DAPI (Molecular Probes, Eugene, Oreg., Catalog No. D21490).
- (r) Anti-5-BrdU, a monoclonal antibody specific for 5-BrdU, (Phoenix Flow Systems, San Diego, Calif., Catalog No. PRB1U).
- (s) Streptavidin (Prozyme, San Leandro, Calif., Catalog No. SA10).
- (t) Aminosilane treated slides (Silane-Prep Slides) (Sigma, Catalog No. S4651).
- (u) 1.5 mL Eppendorf Tubes (Fisher Scientific, Pittsburgh, Pa., Catalog No. 22 36 320-4).
- (v) Clearium Mounting Medium (Surgipath Medical Industries Inc., Richmond, Ill., Catalog No. 01100).

Example I

Preparation of High Purity Gadolinium Trichloride Hydrate and Yttrium Trichloride Hydrate A. Materials
- (a) Gadolinium oxide, $Gd_2O_3$ 99.999% (REO) (Alpha Aesar, Word Hill, Mass., Catalog No. 11289, 2001-02); and Yttrium oxide, $Y_2O_3$ 99.9999% (REO) (Alpha Aesar, Catalog No. 42864, 2001-02).
- (b) Hydrochloric acid, HCl, reagent grade, 12 molar (EMD Chemicals Inc., Gibbstown, N.J., Catalog No. HX0603P-1).
- (c) Chromerge cleaning solution, consisting of chromium oxide, $CrO_3$, in concentrated sulfuric acid (Manostat, New York, N.Y., Catalog No.}.

B. Procedure
- (a) All glassware was cleaned as follows before use: (1) Rinse with methanol/HCl (10%). (2) Rinse with distilled water and dry in oven (60° C.). (3) Rinse with Chromerge. (4) Rinse with exchange-column deionized water. (5) Dry in oven (60° C.), covered with KimWipe (Kimberly-Clark Corp. Dallas, Tex.) tissues to prevent entry of dust particles.
- (b) The oxide (of gadolinium or yttrium) was dissolved in reagent grade 3 molar aqueous HCl with mild heating (60° C.), and the resulting colorless solution was evaporated to dryness in a rotary evaporator at 60° C. under reduced pressure. The solid residue was further dried for several days in vacuo over phosphorus pentoxide and potassium hydroxide. The product was obtained as a colorless crystalline powder.

Example II

Preparation of High Purity Energy Transfer Donor $Gd(TTFA)_3 \cdot n(H_2O)$ Complex A. Materials
- (a) High purity gadolinium trichloride hydrate, $GdCl_3 \cdot 6(H_2O)$, prepared as described in EXAMPLE I.
- (b) The HTTFA of the Most Commonly Used Materials.
- (c) 2,2',2"-nitrilotriethanol (Triethanolamine, TEA), 98% (Aldrich, St. Louis, Mo., Catalog No. TS,830-0). The product was used as received.
- (d) Solvents: Column-deionized water, methanol, chloroform, hexane (all reagent grade).

(e) Decolorizing charcoal, Activated Carbon, DARCO G 60 (Aldrich, Catalog No. 24,227-6).

B Procedure (a) The gadolinium chloride, obtained as described in EXAMPLE I, was dissolved in methanol at ambient temperature. To the resulting solution, the following were added in sequence, gradually and with stirring: (1) solid HTTFA (1:3 mole ratio), and triethanolamine (TEA) (1:3 mole ratio) previously dissolved in a minimal volume of methanol. After a few minutes, a solid began to precipitate, and the mixture was refrigerated for 12 hours. The colorless crystalline solid that formed was filtered off and shown by its infrared spectrum to be the chloride of the TEA reagent. The filtered solution was diluted to six times its original volume with deionized water and a milky suspension was obtained. The mixture was refrigerated for two days. The powdery solid that formed was filtered with suction and washed by repeatedly flushing with deionized water while still on the filter under suction.

(b) The product was purified by repeated fractional crystallization from chloroform/hexane, using charcoal as decolorizing agent. It was finally obtained as a cream-colored microcrystalline powder.

(c) The novel high purity gadolinium complex thus obtained, $Gd(TTFA)_3 \cdot n(H_2O)$, was identified by infrared IR spectroscopy. The spectrum was consistent with the formula $Gd(TTFA)_3 \cdot n(H_2O)$.

(d) The creation of the pure complex eliminated the fluorescent organic impurities originally present in the HTTFA and provided the TTFA ligand as the mononegative anion.

Example III

Preparation of High Purity Energy Transfer Donor $Y(TTFA)_3 \cdot n(H_2O)$ Complex A. Materials (a) High purity yttrium trichloride hydrate, $YCl_3 \cdot 6(H_2O)$, prepared as described in EXAMPLE I.

(b) Materials b through e of EXAMPLE II.

B. Procedure (a) The procedures of EXAMPLE II are followed with the substitution of yttrium trichloride hydrate, $YCl_3 \cdot 6(H_2O)$, for $GdCl_3 \cdot 6(H_2O)$.

(b) The product is purified by repeated fractional crystallization from chloroform/hexane, using charcoal as decolorizing agent. It is finally obtained as a cream-colored micro-crystalline powder.

(c) The novel high purity yttrium complex thus obtained, $Y(TTFA)_3 \cdot n(H_2O)$ is identified by infrared IR spectroscopy. The spectrum is consistent with $Y(TTFA)_3 \cdot n(H_2O)$.

(d) The creation of the pure complex eliminated the fluorescent organic impurities originally present in the HTTFA and provided the TTFA ligand as the mononegative anion.

Example IV

Preparation of the Energy Transfer Donor $Na_3Gd(PDCA)_3$

A. Materials (a) Sodium hydroxide, NaOH, ACS Grade (EM Science, Affiliate of Merck KGaA, Darmstad, Germany, Catalog No. SX 0590-1).

(b) Gadolinium(III) oxide, $Gd_2O_3$, 99.99% (REO), (Alpha Aesar, Word Hill, Mass., Catalog No. 11290, 2001-02).

(c) The 2,6-pyridinedicarboxylic acid of the Most Commonly Used Materials.

(d) Indicating Drierite (anhydrous calcium sulfate with blue cobalt chloride as moisture indicator) (W.A. Hammond Drierite Co., Xenia, Ohio, Catalog No. 23001).

B. Procedure (a) The gadolinium oxide (0.181 g, 0.500 mmol), 2,6-pyridinedicarboxylic acid (0.501 g, 3.00 mmol) and sodium hydroxide (0.120 g, 3.00 mmol) were added to 100 mL of deionized water. The mixture was heated at reflux for one hr, after which time all solids had dissolved to give a colorless, clear solution. The solution was evaporated to dryness under pumping in a rotary evaporator and the resulting white solid was kept in a vacuum desiccator, over Drierite, for 24 hr. (Yield: 0.598 g.) The infrared spectrum of the dry product confirmed the formula $Na_3Gd(PDCA)_3 \cdot n(H_2O)$, with n=3 (estimated from the intensity of the —OH absorption of water at 3400 cm$^{-1}$). The related Eu(III) and La(III) salts have previously been described (Ref. 29).

Example V

Enhancement of EuMac Luminescence from a Poly-D-Lysine Coated Plate by the Addition of Ethanolic Columinescence Solutions A. Materials.

(a) The EuMac-di-NCS of the Most Commonly Used Materials.

(b) The EuMac-di-NCS in DMSO was prepared by dissolving the EuMac-di-NCS in DMSO to produce at 5 mg/mL (5.4 mM) solution.

(c) The HTTFA of the Most Commonly Used Materials was stored at 4° C. in a dark glass container. The stock solution was $1.00 \times 10^{-2}$ M in ethanol.

(d) Gd(III) chloride, $GdCl_3 \cdot 6H_2O$ (Alfa Aesar, Word Hill, Mass., Catalog No. 11287).

(e) 1,10-phenanthroline (Sigma-Aldrich, St. Louis, Mo., Catalog No.13,137-7).

(f) Cetyltrimethylammonium bromide (Sigma-Aldrich, Catalog No. 85,582-0).

(g) Sodium metabisulfite (Spectrum Chemicals & Laboratory Products, Gardena, Calif., Catalog No. SO182).

(h) The aqueous component of the LEL emulsion consisted of 30 mM TRIS, 1 mL/L Triton X-100 of the Most Commonly Used Materials, 150 mM NaCl, 0.10 mM $GdCl_3$, 7.69 mM $NaN_3$, 10 mM sodium metabisulfite ($Na_2S_2O_5$), and 2.5 g/L gelatin of the Most Commonly Used Materials in water.

(i) The ethanolic component of the LEL emulsion consisted of 10.81 mM HTTFA, 2.08 mM 1,10-phenanthroline and 0.19 mM cetyltrimethylammonium bromide in ethanol.

(j) The LEL emulsion Ref. 13) was produced by mixing 30 mL of the aqueous component with 1 mL of the ethanolic component.

(k) $GdCl_3$+3TTFA-EtOH was an ethanolic solution that contains per liter: 116 μmol $GdCl_3$ and 348 μmol HTTFA, (l) $Gd(TTFA)_3$-EtOH was an ethanolic solution containing per liter: 300 μmol of the $Gd(TTFA)_3$ of EXAMPLE II.

(m) 384-well Microtiter Poly-D-Lysine Plate (Greiner Bio-One, Longwood, Fla., Catalog No. 781946).

(n) The TBS-Azide of the Most Commonly Used Materials.
(o) The bicarbonate-carbonate buffer (pH 8.7) consisted of a mixture of 9 parts 1 M NaHCO$_3$ and 1 part 1 M Na$_2$CO$_3$.
(p) The wash buffer consisted of a mixture of 20 mM NaHCO$_3$ and 150 mM NaCl (pH ~8.5).

B. Procedure
(a) Each of the wells was washed twice with 100 µL wash buffer and the supernatant was removed by aspiration.
(b) Twenty µL of wash buffer was pipetted into each well.
(c) Two µL of bicarbonate-carbonate buffer was added to each well.
(d) Two µL of the EuMac-di-NCS in DMSO was added and the solution was mixed by lightly tapping against the microtiter plate wall.
(e) The microtiter plate was placed on Pipette Aid® pump (Drummond Scientific Co., Broomall, Pa.) and firmly attached with Scotch tape to permit agitation.
(f) The plate was covered with aluminum foil; the solution in the wells was incubated with agitation for 30 min and then removed.
(g) The wells were washed 5 times with 100 µL of TBS-Azide, which was removed by aspiration.
(h) 10 µL of each of the solutions shown in Table 1 were delivered into wells a, b, d, e, g, h, j, k, m, and n and their controls of the microtiter plate. Wells c, f, i, and l served as controls and did not receive any fluid.
(i) The wells were allowed to air dry overnight in the dark. No special steps were taken to minimize the ambient relative humidity.
(j) The microtiter plates were inserted into UVP Epi Chem II Darkroom and illuminated with the long UV (ca. 365 nm) bulb. Digital images were acquired with the Retiga-1350 EX camera. The emission intensity of the bottom of each well was measured with Fovea PhotoShop plug-in where "feature region" is available. The integrated optical density (IOD), which is the integral of the linear measurements and thus is a measurement of the total luminescence and autofluorescence emission, was calculated. For each pair of wells, the integrated emission of the control was subtracted from that of the EuMac labelled well.
(k) The wells in the top row of FIG. 1 had the EuMac-di-NCS coupled to their poly-D-Lysine. The wells in the bottom row are negative controls, which have not been coupled with EuMac-di-NCS.

TABLE 1

Solutions Applied to Wells

| | |
|---|---|
| a & b | Aqueous LEL |
| d & e | HTTFA in ethanol |
| g & h | GdCl$_3$ + 3TTFA-EtOH |
| j & k | Gd(TTFA)$_3$-EtOH |
| m & n | GdCl$_3$ in ethanol |

Only negative control wells (a and b bottom row) had any significant emission. This was probably due to the Eu(III) contaminant present in the GdCl$_3$. The Gd(TTFA)$_3$-EtOH negative control wells (j and k bottom row) had a faint spot in the center. The other negative control wells did not luminesce. As described in U.S. Pat. No. 6,340,744 (Ref. 5), the dry, EuMac-containing wells (a and b top row), to which the LEL (cofluorescence) emulsion had been added, luminesced brightly. The EuMac containing wells (d and e top row), to which only HTTFA had been added, luminesced weakly. The EuMac containing wells (g and h top row), to which the GdCl$_3$+3TTFA-EtOH)-EtOH had been added, luminesced moderately. The EuMac containing wells (j and k top row), to which the Gd(TTFA)$_3$-EtOH had been added, luminesced brightly. And the EuMac containing wells (m and n top row), to which the GdCl$_3$ in ethanol had been added, did not luminesce. Unexpectedly, a simple ethanolic solution of Gd(TTFA)$_3$ can replace the complex micellar solution of U.S. Pat. No. 6,340,744 (Ref. 5). Surprisingly, the use of the Gd(TTFA)$_3$ complex instead of the same amount of GdCl$_3$+3TTFA, increases the luminescence.

Example VI

Enhancement of EuMac Luminescence from a Poly-D-Lysine Coated Plate by the Addition of Ethanol-Water Columinescence Solutions A. Materials.
(a) The EuMac-di-NCS of the Most Commonly Used Materials.
(b) The LEL emulsion of the Most Commonly Used Materials.
(c) Gd-TTFA-EtOH is an ethanolic solution that contains: 116 µM GdCl$_3$ and 348 µM HTTFA.
(d) The Gd(TTFA)$_3$ of EXAMPLE II.
(e) 384-well Microtiter Poly-D-Lysine Plate (Greiner Bio-One, Longwood, Fla., Catalog No. 781946).
(f) The TBS-Azide of the Most Commonly Used Materials.

B. Procedure
(a) The procedures of EXAMPLE V were repeated with the substitution of Gd(TTFA)$_3$ in mixtures of ethanol and water for Gd(TTFA)$_3$-EtOH. In the Abbreviations shown in FIG. 2, the ethanol percentage is given as a numeric prefix to ETOH.
(b) As shown in FIG. 2, negative control wells (–), left column, (E, F, I, J, K, O, and P) had a weak emission at their periphery. Well (L) had a weak emission from its center. The strongest emissions from the EuMac stained wells (+), right column, were from the two aqueous LEL emulsion samples (O and P), three of the Gd(TTFA)$_3$-EtOH (I, J, and K) and one Gd(III)-TTFA-5OEtOH (F). The Integrated Luminescence (arbitrary units) is the difference between the luminesce of the europium macrocycle stained well and the unstained control well. Both the formation of the Gd(TTFA)$_3$ complex from the mixture of GdCl$_3$ and HTTFA, and the drying of the solutions may have been influenced by the solvent composition.

Since the formulation of the Gd(TTFA)$_3$-EtOH is relatively simple, the luminescence obtained with it is comparable to that of the aqueous columinescence solutions, and the air drying from these alcoholic solutions decrease the artifacts associated with air drying cells from aqueous solutions, the use of Gd(TTFA)$_3$-EtOH together with air drying will be very useful for cytology, histology and other determinations of analytes. The low cost of ethanol, its availability in cytology and histology laboratories, and its relative lack of toxicity are also incentives for its use.

Example VII

Enhancement of EuMac Luminescence from a Poly-D-Lysine Coated Plate by the Addition of Other Columinescence Solutions A. Materials.
(a) The EuMac-di-NCS of the Most Commonly Used Materials.

(b) The LEL emulsion of the Most Commonly Used Materials.
(c) Gd(III)-H$_2$O is an aqueous solution that contains per liter: 116 μmol GdCl$_3$.
(d) Gd-MeOH is a methanolic solution that contains per liter: 116 μmol GdCl$_3$.
(e) Gd-Isopropanol is an isopropanol solution that contains per liter: 116 μmol GdCl$_3$.
(f) TTFA-H$_2$O is an aqueous solution that contains per liter: 348 μmol HTTFA.
(g) TTFA-MeOH is a methanolic solution that contains per liter: 348 μmol HTTFA.
(h) TTFA-Isopropanol is an isopropanol solution that contains per liter: 348 μmol HTTFA.
(i) Gd-TTFA-H$_2$O is an aqueous solution that contains per liter: 116 μmol GdCl$_3$ and 348 μmol HTTFA.
(j) Gd-TTFA-MeOH is a methanolic solution that contains per liter: 116 μmol GdCl$_3$ and 348 μmol HTTFA.
(k) Gd-TTFA-Isopropanol is an isopropanol solution that contains per liter: 116 μmol GdCl$_3$ and 348 μmol HTTFA.
(l) Gd(TTFA)$_3$-H$_2$O is a saturated solution of the Gd(TTFA)$_3$ of EXAMPLE II in water.
(m) Gd(TTFA)$_3$-MeOH is a methanolic solution that contains per liter: 300 μmol of the Gd(TTFA)$_3$ of EXAMPLE II.
(n) Gd(TTFA)$_3$-Isopropanol is an isopropanol solution that contains per liter: 300 μmol of the Gd(TTFA)$_3$ of EXAMPLE II.
(o) 384-well Microtiter Poly-D-Lysine Plate (Greiner Bio-One, Longwood, Fla., Catalog No. 781946).
(p) The TBS-Azide of the Most Commonly Used Materials.

B. Procedure
(a) The procedures of EXAMPLE V were repeated with the substitution of Gd(TTFA)$_3$-MeOH, Gd(TTFA)$_3$-Isopropanol, and Gd(TTFA)$_3$-H$_2$O for Gd(TTFA)$_3$-EtOH.
(b) As shown in FIG. 3, the negative control wells (−), left column, (A, E, H, I, K, and L) had a weak emission at their periphery. The column labeled Mean EuMac— Mean Neg. Cntrl contains the mean difference between the luminescence (arbitrary units) of the EuMac-di-NCS coated well and that of the uncoated control well of each row. Although the negative control well (L) had a weak mean emission from its center (33), this was much weaker than that of the EuMac stained well (185), right column. The two strongest corrected mean emissions from the EuMac stained wells were from the aqueous LEL emulsion sample (A) and the Gd(TTFA)$_3$-MeOH (L), which were respectively 190 and 152. The aqueous formulations Gd(III)-TTFA-H$_2$O (H) and Gd(TTFA)$_3$-H$_2$O (K) showed significantly enhanced corrected mean emissions, respectively 91 and 67, versus the corrected mean emission, 14.8, of the well with only HTTFA (E). The Gd(TTFA)$_3$-MeOH sample (L) had a much stronger corrected emission than all of the other samples except for the aqueous LEL emulsion (A).

Since the formulation of the Gd(TTFA)$_3$-EtOH of EXAMPLE VI and the Gd(TTFA)$_3$-MeOH are very simple compared to that of the LEL emulsion, the alcoholic solutions evaporate much faster, and their storage characteristics are much better, both alcoholic solutions are to be preferred to an aqueous emulsion. These results could be generalized to suggest the investigation of volatile solvents that can dissolve Gd(TTFA)$_3$ or other ligand salts. For studies where surface tension and rate of evaporation are not considerations, an aqueous solution of Gd(TTFA)$_3$ might be considered since water is the least expensive of the solvents.

Example VIII

Preparation of EuMac-Streptavidin

A. Materials.
(a) The EuMac-mono-NCS of the Most Commonly Used Materials.
(b) 1 M NaHCO$_3$ adjusted to pH 9.0 with 1 M Na$_2$CO$_3$.
(c) 50 M NaHCO$_3$ (pH 8.6) made from a 1 M NaHCO$_3$ solution. No pH adjustment was required.
(d) Dimethyl Sulfoxide (DMSO), (Sigma, St. Louis, Mo., Product No. D-5879).
(e) 20 mg/mL of EuMac-mono-NCS in DMSO.
(f) The Streptavidin of the Most Commonly Used Materials.
(g) 2-(4-hydroxyphenylazo)-benzoic acid (HABA), (Aldrich, St. Louis, Mo., Catalog No. 14,803-2)
(h) The 1.5 M NH$_2$OH.HCl (pH8.5) of the most commonly used materials.
(i) G-25 XK16 column (Sephadex G-25 superfine and XK16/20 column, Amersham Pharmacia, Piscataway, N.J., part no. 17-0031-01 and 18-8773-01, respectively).
(j) Bradford Method, protein assay kit (Amresco, Solon, Ohio, product code: E535).

B. Procedure
(a) 12.5 mg of streptavidin was dissolved in 0.625 mL of 50 mM NaHCO$_3$ (pH 8.6) buffer. A protein concentration of 31.9 mg/mL was determined from the absorbance at 280 nm, measured with a Shimadzu UV 2401 PC Model No. 206-82301-92 spectrophotometer. The samples were examined in stoppered 40 μL quartz cuvettes (Starna, 16.40-Q-10).
(b) 0.315 mL of a 31.5 mg/mL streptavidin stock solution (10 mgs of streptavidin) was pipetted into a 2 mL plastic tube (Fisher Scientific, Pittsburgh Pa., Catalog No. 02-681-343) with cap (Fisher Scientific, Catalog No. 02-681-360), equipped with a micro stirring bar. To this, 0.186 mL of 50 mM HCO$_3$ was added to make a total volume of 0.5 mL and a final concentration of streptavidin of 20 mg/mL. Stirring was started and was continued during the entire experiment.
(c) 50 μL of a saturated HABA solution in 20 mM NaHCO$_3$ was added. (The pH of this HABA solution was approximately 6.9).
(d) 55 μL of 1 M NaHCO$_3$, pH 9.0, was added with stirring.
(e) 150 μL of a 20 mg/nL solution of EuMac-mono-NCS was added. The molar ratios of the streptavidin, HABA, and EuMac-mono-NCS were 1:2.2:19.4, respectively.
(f) The solution was incubated with stirring for 60 min at room temperature (~25° C.)
(g) At the end of the 60 min period, any remaining isothiocyanate was destroyed by the addition of 4 μL of the 1.5 M NH$_2$OH.HCl (pH8.5) solution.
(h) The mixture was incubated, with stirring, for an additional 30 min to complete the quenching reaction. The magnetic stirring bar was then removed and the tube was centrifuged for 2 min at 17,000 g (Hermle Z 180 Microcentrifuge) to remove any precipitate that may have formed.
(i) The clear protein solution was transferred to a 1.5 mL Eppendorf Tube of the Most Commonly Used Materials and purified by size-exclusion chromatography on a Sephadex G-25 (Amersham Biosciences, Piscataway, N.J., Catalog No. 17-0033-10) in a column 16 mm in diameter by 200 mm long, using TBS-Azide as the eluant and a UV detector.
(j) The first 10 mL fraction contained EuMac-Streptavidin. Each fraction was collected into a 15 mL disposable sterile centrifuge conical tube (Fisher Scientific, Catalog No. 05-539-5).
(k) The protein concentration of each sample was determined according to the instructions provided with the Bradford protein assay kit. The yield of protein conjugate was about 46%.
(l) The UV spectra of the conjugate and of streptavidin were obtained in TBS-Azide pH 7.25 buffer.
(m) As is shown in FIG. 4, the streptavidin conjugate had a strong absorption at 250-260 nm, and a comparison between the absorbance of the EuMac-streptavidin conjugate and that of the EuMac-mono-NCS confirmed the presence of coupled europium macrocycles. A perfect matching of the spectra would not be expected since the isothiocyanate group of the EuMac-mono-NCS is replaced during coupling by a thiourea group, and the spectrum of the EuMac-mono-NCS was obtained in DMF.

Example IX

Linearity Study of EuMac-Streptavidin Binding to Biotinylated Microwells

A. Materials
(a) The EuMac-Streptavidin of EXAMPLE VIII, diluted in the TBS-Azide of the Most Commonly Used Materials to a concentration of 0.23 mg/mL.
(b) The Streptavidin of the Most Commonly Used Materials.
(c) Fluorescein-labeled streptavidin (Phoenix Flow Systems, San Diego, Calif., Catalog No. SAFM1.
(d) Reacti-Bind Biotin Coated Microwell Strip Plates (Pierce Biotechnology, Inc., Rockford, Ill., Catalog No. 15151).
(e) Gd(TTFA)$_3$-EtOH is an ethanolic solution that contains per liter: 300 µmol of the Gd(TTFA)$_3$ of EXAMPLE II.
(f) BSA pH 7.0 is a solution that contains 0.5% w/v BSA in the TBS-Azide of the Most Commonly Used Materials.
(g) BSA pH 8.5 is a solution that contains 0.5% w/v BSA in the TBS-Azide. The final pH is 8.5.
(h) Parafilm 4 in.×125 ft. roll (Laboratory Film), (Pechiney Plastic Packaging, Menasha, Wis., Catalog No. PM-996).
B. Procedure
(a) One hundred µL of BSA pH 8.5 was added to each of the Biotin-Coated Microwells and the supernatant was removed by aspiration. A second 100 µL of BSA pH 8.5 was added. The biotinylated wells were incubated for 15 min at room temperature (26° C.) and the supernatant was removed by aspiration.
(b) The biotinylated wells were rinsed twice with 100 µL of BSA pH 7.0.
(c) A series of dilutions of the EuMac-Streptavidin conjugate were made to create solutions with 1,200, 240, 48, 9.6 and 1.92 ng/mL of the conjugate in BSA 7.0. Two control solutions, containing 150,000 ng/mL of either streptavidin or of the fluorescein conjugate of streptavidin in BSA 7.0, were also prepared.
(d) 100 µL of each of the EuMac-Streptavidin conjugate samples was added to a biotinylated well and the solutions were agitated to facilitate the binding of the streptavidin conjugates to the biotin by lightly tapping against microtiter strip wall. The microtiter strip was covered with Parafilm to prevent evaporation and incubated at room temperature (26° C.) for 40 min in the dark.
(e) The supernatants were removed and the biotinylated wells were washed 3 times with 100 µL of BSA pH 7.0, which was removed by aspiration.
(f) The biotinylated wells were allowed to dry.
(g) Two drops (~25 µL) of the Gd(TTFA)$_3$-EtOH was added to each biotinylated well.
(h) The biotinylated wells were allowed to air dry overnight in the dark.
(i) The microwell strip plates were inserted into UVP Epi Chem II Darkroom, illuminated with the long UV (ca. 365 nm) bulb, and the emission was passed through a 619 nm filter. Digital images of the strip plates were acquired with the Retiga-1350 EX camera.
(j) The image of the center 81% of the area of the biotinylated well was analyzed. The mean of the luminescence emission intensity was calculated with Fovea PhotoShop plug-in under Filter/IP*Features/Regions.
(k) In the graph of FIG. 5, the equation of the linear part of the emission intensity of EuMac-streptavidin bound to the biotinylated wells is y=0.0038x+26.064 and the linearity is $R^2$=0.9995. This demonstrates that the EuMac-labeled member of a specific combining pair can be detected and quantitated after being dried from a homogeneous solution. For unknown, possibly instrumental reasons, the first two points have a much steeper slope. The emissions of control samples of streptavidin and of fluorescein-labeled streptavidin, both at 150,000 ng/mL, and of BSA at 5 mg/mL are shown at the ordinate. Although the streptavidin-fluorescein conjugate has saturated the well, only a very small part of the long wavelength tail of the fluorescein emission passes through the 619 nm filter. The sensitivity of this assay can be improved by the use of either a time gated system and or an optimized optical system capable of gathering a larger part of the luminescent emissions. Thus, the feasibility of immunoassays and other assays involving specific combining pairs has been demonstrated.

Example X

Optimization of the Lanthanide Enhanced Luminescence of EuMac by HTTFA and Gd(TTFA)$_3$
A. Materials
(a) The EuMac-Streptavidin of EXAMPLE VIII diluted in the TBS-Azide of the Most Commonly Used Materials to a concentration of 0.05 mg/mL.
(b) Reacti-Bind Biotin Coated Microwell Strip Plates (Pierce Biotechnology, Inc., Rockford, Ill., Catalog No. 15151).
(c) The Gd(TTFA)$_3$ of EXAMPLE II was dissolved in ethanol to produce a $1.0 \times 10^{-2}$ M, or $1.0 \times 10^7$ nM, stock solution. This solution was serially diluted tenfold with ethanol to produce a series of solutions, Gd(TTFA)$_3$-EtOH solutions, with the most dilute solution being $1.0 \times 10^{-9}$ M or 1.0 nM. For these solutions, the concentration expressed as Eqv/L of TTFA anion is equal to three times the concentration expressed as molarity of Gd(TTFA)3 complex. Thus, the Gd(TTFA)3-EtOH solutions ranged from $3.0 \times 10^7$ nEqv/L to 3.0 nEqv/L of TTFA anions.
(d) A 30 mM stock solution of the HTTFA of the Most Commonly Used Materials in ethanol. This solution was serially diluted tenfold with ethanol to produce a series of solutions, HTTFA-EtOH solutions, with the most dilute solution being $3.0\times10^{-9}$ M or 3.0 nM. Each HTTFA-EtOH solution had the same enhancer concentration as its corresponding Gd(TTFA)$_3$-EtOH solution, except for the enhancer being in the molecular HTTA form instead of the mono-negative anionic TTFA form. For HTTFA, the concentration of material expressed as Eqv/L of the acid is equal to that expressed as molarity.

(e) The BSA pH 7.0 of EXAMPLE IX.
(f) The BSA pH 8.5 of EXAMPLE IX.
(g) The Parafilm of EXAMPLE IX.

B Procedure
(a) One hundred µL of BSA pH 8.5 was added to each of the wells of the Reacti-Bind Biotin Coated Microwell Strip Plates at room temperature (26° C.) and the supernatant was removed by aspiration.
(b) A second 100 µL of BSA pH 8.5 was added to each well. The wells were incubated for 15 min. at room temperature (26° C.) and the supernatant was removed by aspiration.
(c) Just prior to use, 0.05 mg/ml EuMac-Streptavidin solution was diluted with the BSA pH 7.0 solution to a final concentration of 0.5 µg/mL.
(d) 50 µL of the 0.5 µg/mL EuMac-Streptavidin solution was pipetted into each of eight biotinylated well. An equal number of control wells did not receive the EuMac-Streptavidin. Then, the microtiter strip was covered Parafilm to prevent evaporation and incubated at room temperature (25° C.) and in the dark for approximately 30 min.
(e) The supernatants were removed and the EuMac-Streptavidin and control wells were washed 3 times with 100 µL of BSA pH 7.0, which was removed by aspiration.
(f) The wells were allowed to dry at room temperature.
(g) The Gd(TTFA)$_3$-EtOH serial dilutions, from $1.0\times10^7$ nM to 1.0 nM, were added to a set of 8 wells (30 µL per well), in a sequential manner. Both EuMac-Streptavidin-coated wells and control wells were so treated.
(h) The TTFA-EtOH serial dilutions, from $3.0\times10^7$ nM to 3.0 nM, were added to another set of 8 wells (30 µL per well), in a sequential manner. Both EuMac-Streptavidin-coated wells and control wells were so treated.
(i) The microtiter strips were allowed to air dry overnight in the dark.
(j) The microtiter strips were placed into UVP Epi Chem II Darkroom and illuminated with the long UV (ca. 365 nm) bulb and the emission passed through a 619 nm filter. Digital images of the strips were acquired with the Retiga-1350 EX camera.
(k) The image of the center 81% of the area of the microwell was analyzed. The average emission intensity was calculated with Fovea PhotoShop plug-in under Filter/IP*Features/Regions. Four sets of data were measured: Gd(TTFA)$_3$-EtOH added to control wells (Ctrl. Gd(TTFA)$_3$), Gd(TTFA)$_3$-EtOH added to EuMac-Streptavidin coated wells (EuMac-Strept+Gd(TTFA)$_3$), HTTFA-EtOH added to control wells (Ctrl. HTTFA), and HTTFA-EtOH added to EuMac-Streptavidin coated wells (EuMac-Strept+HTTFA). The data are shown in Table 2. The average emission intensities for the Gd(TTFA)$_3$ solutions are shown on the left and those for the HTTFA solutions on the right. As expected because of the small europium contamination in the gadolinium, there is an increase in luminescence with concentration for the Gd(TTFA)$_3$ solutions in the control wells (Ctrl. Gd(TTFA)$_3$). The results with the HTTFA solutions in the control wells (Ctrl. HTTFA) are essentially constant. The maxima for both solutions occurred at the second highest concentration, $1.0\times10^6$ nM Gd(TTFA)$_3$ and $3.0\times10^6$ nM HTTFA. An inner filter effect is a possible explanation for the quenching of the luminescence at the highest concentration.

TABLE 2

| Gd (TTFA)$_3$ (nM) | EuMac-Strept + Gd (TTFA)$_3$ | Ctrl. Gd (TTFA)$_3$ | EuMac-Strept + Gd (TTFA)$_3$-Ctrl. | HTTFA (nM) | EuMac-Strept + HTTFA | Ctrl. HTTFA | EuMac-Strept + HTTFA-Ctrl. |
|---|---|---|---|---|---|---|---|
| $1.0\times10^7$ | 140 | 61 | 80 | $3.0\times10^7$ | 42 | 22 | 20 |
| $1.0\times10^6$ | 160 | 40 | 120 | $3.0\times10^6$ | 49 | 23 | 26 |
| $1.0\times10^5$ | 75 | 37 | 38 | $3.0\times10^5$ | 46 | 24 | 22 |
| $1.0\times10^4$ | 31 | 25 | 5 | $3.0\times10^4$ | 35 | 23 | 11 |
| $1.0\times10^3$ | 25 | 26 | −1 | $3.0\times10^3$ | 31 | 23 | 8 |
| $1.0\times10^2$ | 23 | 25 | −2 | $3.0\times10^2$ | 28 | 23 | 5 |
| $1.0\times10^1$ | 21 | 21 | −1 | $3.0\times10^1$ | 25 | 22 | 3 |
| 1.0 | 19 | 20 | 0 | 3.0 | 22 | 20 | 2 |

(l) FIG. 6 consists of plots of the EuMac-Streptavidin net luminescence (Gd(TTFA)$_3$-Ctrl. and HTTFA-Ctrl.), corrected for the background from the control wells. Only the concentration in nEqv/L of TTFA anions or HTTFA molecules is shown. In order to provide the same number of enhancers, the concentrations of the HTTFA solutions are three times those of the Gd(TTFA)$_3$. The increases in luminescence that resulted from the additions of the Gd(TTFA)$_3$ (circles) and of the HTTFA (squares) solutions are shown. The ratio (triangles) of these increases is also shown. At low concentrations of Gd(TTFA)$_3$, the luminescence of the EuMac-Streptavidin was less than that observed with a comparable concentration of HTTFA. This possibly resulted from a significant fraction of the europium macrocycles being incompletely complexed with TTFA because of the competition between the Gd(III) ions and the EuMacs for the insufficient supply of TTFA ligands. At higher concentrations, the supply of TTFA ligands from the Gd(TTFA)$_3$ was sufficient to produce cofluorescence, which was maximum for $1.0\times10^6$ nM Gd(TTFA)$_3$ with an emission intensity ratio of 4.6 between the sample with added Gd(TTFA)3 and the sample with the equivalent content of HTTFA.
(m) This experiment was repeated (data not shown) with a different lot of the EuMac-Streptavidin. The maxima for both solutions occurred again with $1.0\times10^6$ nM Gd(TTFA)$_3$ and $3.0\times10^6$ nM HTTFA, and the maximum ratio was again 4.6. For both experiments, removal of the europium contaminant present in the gadolinium used to produce Gd(TTFA)$_3$ would significantly increase this ratio.

In the solid phase, the ratio (4.6) between the luminescence intensity of samples of EuMac-Streptavidin with Gd(III) and without Gd(III), both at the same total content of TTFA, shows that the presence of Gd(III) produced a useful luminescence enhancement, although smaller than for samples of comparable concentration in the aqueous LEL emulsion. Example VII of U.S. Pat. No. 6,340,744 teaches that the presence of Gd(III) with a EuMac-avidin conjugate resulted in a "more than ten times higher (luminescence) than that of the other solutions". The simplest explanation for the unexpected decrease in luminescence intensity ratio (from 10 to 4.6) with the system considered in this Example is that the lower ratio is not the result of a diminution of energy transfer from the $Gd(TTFA)_3$ to the EuMac; but instead, is the result of resonance energy transfer (Ref. 30) by HTTFA molecules or by the excess TTFA anions, which are neither complexed with the gadolinium ion nor bound to Eu macrocycles. This energy transfer either could occur directly to the europium ion, or indirectly by homogeneous resonance energy transfer (Ref. 30) to the TTFA anions that are complexed to the europium. The evaporation of the solvent increases the concentration of the unbound HTTFA molecules and unbound TTFA anions and decreases their distance from the EuMac and its bound TTFA anions, thus favoring the energy transfer process. Thus the HTTFA containing solutions are unitary luminescence enhancing solutions.

Example XI

Optimization of the Lanthanide Enhanced Luminescence of EuMac in the Presence of TTFA Anions A. Materials
  (a) The EuMac-Streptavidin of EXAMPLE VIII diluted in the TBS-Azide of the Most Commonly Used Materials to a concentration of 0.05 mg/nL.
  (b) Reacti-Bind Biotin Coated Microwell Strip Plates (Pierce Biotechnology, Inc., Rockford, Ill., Catalog No. 15151).
  (c) The $Gd(TTFA)_3$ of EXAMPLE II was dissolved in ethanol to produce a 10,000 µM (10 mM) stock solution. This ethanolic 10 mM stock solution was prepared by dissolving 8.2 mg in 1.0 µL of ethanol. This solution was serially diluted tenfold with ethanol to produce 1000 µM, 100 µM, and 10.0 µM $Gd(TTFA)_3$-EtOH solutions.
  (d) NaTTFA was prepared by mixing the HTTFA of the Most Commonly Used Materials (1.11 g, 5.00 mmol, dissolved in 5.0 mL of anhydrous ethanol) with NaOH (0.200 g, 5.00 mmol, dissolved in 20 mL of anhydrous ethanol). The clear solution thus obtained was evaporated to dryness under reduced pressure. The residue was taken up with 5.00 mL of diethylether and 25 mL of hexane were slowly added to the resulting mixture, with stirring. After refrigeration for 12 hr, the white powdery solid that had formed was filtered off, washed with hexane, and dried in vacuo over Drierite. The IR spectrum of the product confirmed its composition.
  (e) A 30 mM stock ethanolic solution of the NaTTFA (NaTTFA-EtOH) was prepared by dissolving of (8.6 mg) in 1.174 mL of ethanol. This 30 mM NaTTFA-EtOH solution was serially diluted tenfold with ethanol to produce 3000 µM, 300 µM, and 30.0 µM NaT-TFA-EtOH solutions. Each NaT-TFA-EtOH solution had the same TTFA anion concentration as one of the $Gd(TTFA)_3$-EtOH solutions of Step (c).
  (f) Equal volumes of the $Gd(TTFA)_3$-ETOH and Na-TTFA-EtOH solutions from (c) and (e), having the same TTFA anion concentrations, were mixed together to produce corresponding Gd+Na(TTFA) solutions with the same series of concentrations.
  (g) The BSA pH 7.0 of EXAMPLE IX.
  (h) The BSA pH 8.5 of EXAMPLE IX.
  (i) The Parafilm of EXAMPLE IX.
B. Procedure
  (a) Steps (a) through (f) of the procedures of EXAMPLE X were repeated.
  (b) The 1,000 µM, 100 µM, and 10.0 µM $Gd(TTFA)_3$-EtOH solutions were added to a set of 6 wells (30 µL per well), in a sequential manner. Each solution was added to a EuMac-Streptavidin-coated well and control well.
  (c) The 3,000 µM, 300 µM, and 30.0 µM NaTTFA-EtOH solutions were added to a set of wells (30 µL per well), in a sequential manner. Each solution was added to a EuMac-Streptavidin-coated well and to a control well.
  (d) The 3,000 µEqv/L, 300 µEqv/L, and 30.0 µEqv/L Gd+Na(TTFA) solutions were added to a set of 6 wells (30 µL per well), in a sequential manner. Each solution was added to a EuMac-Streptavidin-coated well and to a control well.
  (e) Steps (i), (j), and (k) of the procedures of EXAMPLE X were repeated.
  (f) Six sets of data were measured: $Gd(TTFA)_3$-EtOH added to EuMac-Streptavidin coated wells (EuMac-Strept+$Gd(TTFA)_3$), $Gd(TTFA)_3$-EtOH added to control wells (Ctrl. $Gd(TTFA)_3$), NaTTFA-EtOH added to EuMac-Streptavidin coated wells (EuMac-Strept+NaT-TFA), NaTTFA-EtOH added to control wells (Ctrl. NaT-TFA), the Gd+Na(TTFA) solutions added to EuMac-Streptavidin coated wells (EuMac-Strept+Gd+Na (TTFA) Solution), and the Gd+Na(TTFA) solutions added to control wells (Ctrl. Gd+Na(TTFA) Solution). The data are shown in FIG. 7 and in Table 3. The results for the wells treated with the $Gd(TTFA)_3$ solutions are shown on the left and those for the wells treated with the Na(TTFA) solutions on the right of Table 3a. As expected because of the small europium contamination in the gadolinium, there is an increase in luminescence with concentration for the Ctrl. $Gd(TTFA)_3$ wells. The results for the Na(TTFA) in the Ctrl. Na(TTFA) wells are essentially constant. With the EuMac-Streptavidin coated wells, the maximum net luminescence occurred at the highest concentration, 1,000 µM, for the $Gd(TTFA)_3$ and at the second highest concentration, 300 µM, for the Na(TTFA).

TABLE 3a

| Gd $(TTFA)_3$ (µM) | EuMac-Strept + Gd $(TTFA)_3$ | Ctrl. Gd $(TTFA)_3$ | EuMac-Strept + Gd $(TTFA)_3$-Ctrl. | Na (TTFA) (µM) | EuMac-Strept + Na (TTFA) | Ctrl. Na (TTFA) | EuMac-Strept + Na (TTFA)-Ctrl. |
|---|---|---|---|---|---|---|---|
| 1,000 | 136.9 | 32.2 | 104.7 | 3,000 | 65.9 | 37.7 | 28.3 |
| 100 | 100.5 | 25.3 | 75.5 | 300 | 61.8 | 24.8 | 37.1 |
| 10 | 45.6 | 21.7 | 24.0 | 30 | 52.6 | 23.0 | 29.6 |

TABLE 3b

| Gd (TTFA)$_3$ (µM) | Na (TTFA) (µM) | EuMac-Strept + Gd + Na(TTFA) Solution | Ctrl. Gd + Na(TTFA) Solution | EuMac-Strept + Gd + Na(TTFA) Solution-Ctrl. |
|---|---|---|---|---|
| 500 | 1,500 | 188.0 | 34.9 | 153.1 |
| 50 | 150 | 100.6 | 30.7 | 69.9 |
| 5 | 15 | 43.7 | 27.8 | 16.1 |

The results for the wells treated with the Gd+Na(TTFA) solutions are shown in Table 3b. As expected because of the small europium contamination in the gadolinium, there is an increase in luminescence with concentration for the control wells. With the EuMac-Streptavidin coated wells, the maximum net luminescence occurred at the highest concentration, 1,000 µM (3,000 µEqv/L), for the Gd(TTFA)$_3$ and Gd+Na (TTFA) solutions; the maximum net luminescence occurred at the second highest concentration, 300 µM, for the NaTTFA solution. For each data point, the concentration of the TTFA anions was 3 times the concentration of the Gd(TTFA)$_3$, shown on the abscissa of FIG. 7. An inner filter effect is a possible explanation for the quenching of the luminescence at the highest concentration of Na(TTFA).

In the solid phase, the ratio (3.7) between the luminescence intensity of the EuMac-Streptavidin samples with Gd(TTFA)$_3$ and the EuMac-Streptavidin samples with Na(TTFA), both at the same total concentration of TTFA anions (3,000 µEqv/L), shows (Table 3a) the enhancement caused by gadolinium to be lower than observed in EXAMPLE X, where the ratio was 4.6. The ratio was further decreased, to a value of 2.8, when taken at the highest net intensity value for the EuMac-Streptavidin samples with Na(TTFA), corresponding to a TTFA concentration of 300 µEqv/L. At the highest concentrations of the Gd(TTFA)$_3$ (Table 3a) and Gd+Na(TTFA) solutions (Table 3b), the ratio of the luminescence intensities (104.7/153.1) was 0.7. Thus, under some conditions, lowering the concentration of the Gd(III) ion can increase the luminescence intensity.

Example VII of U.S. Pat. No. 6,340,744 teaches that the presence of Gd(III) with a EuMac-avidin conjugate in a micellar solution resulted in a "more than ten times higher (luminescence) than that of the other solutions". The simplest explanation for the unexpected decrease in luminescence intensity ratio (from 10 to 3.7) with the system considered in this Example is that the lower ratio is not the result of a diminution of energy transfer from the Gd(TTFA)$_3$ to the EuMac; but instead, is the result of resonance energy transfer (Ref. 30) by the excess TTFA anions, which are neither complexed with the gadolinium ion nor bound to Eu macrocycles. This unexpected energy transfer either could occur directly to the europium ion, or indirectly by homogeneous resonance energy transfer (Ref. 30) to the TTFA anions that are complexed to the europium ion. The evaporation of the solvent increases the concentration of the HTTFA molecules and TTFA anions, thus favoring the energy transfer process. Thus the Na(TTFA) and Gd(TTFA)$_3$ containing solutions and their mixtures are unitary luminescence enhancing solutions.

Example XII

Optimization of the Lanthanide Enhanced Luminescence of EuMac in the Presence of TTFA Anions and HTTFA A. Materials
 (a) The materials of EXAMPLE XI.
 (b) The 30 mM stock solution of the HTTFA in ethanol (HTTFA-EtOH) of EXAMPLE X was serially diluted tenfold with ethanol to produce 3000 µM, 300 µM, and 30.0 µM HTTFA-EtOH solutions. Each HTTFA-EtOH solution had the same enhancer concentration as its corresponding Gd(TTFA)$_3$-EtOH solution, except for the enhancer being in the molecular HTTA form instead of the mono-negative anionic TTFA form.
 (c) The Gd+HTTFA solutions were prepared by mixing equal volumes of the Gd(TTFA)$_3$-ETOH and HTTFA-EtOH solutions.
 (d) The Na+HTTFA solutions were prepared by mixing equal volumes of the Na(TTFA)-ETOH and HTTFA-EtOH solutions.

B. Procedure
 (a) Steps (a) through (f) of the procedures of EXAMPLE X were repeated.
 (b) The 10,000 µM, 1,000 µM, 100 µM, and 10.0 µM Gd(TTFA)$_3$-EtOH one-component solutions were each added to 3 wells (30 µL per well). Two aliquots of each solution were added to EuMac-Streptavidin-coated wells and a third to a control well.
 (c) The procedure of step (b) was repeated with the HTTFA-EtOH and NaTTFA-EtOH one-component solutions. However, since in Gd(TTFA)$_3$-EtOH there are 3 TTFA anions for each Gd(III), the concentrations of the 30 µL aliquots of the HTTFA-EtOH and Na(TTFA)-EtOH solutions were 3,000 µM, 3,000 µM, 300 µM, and 30 µM, respectively.
 (d) Three One-to-One 30,000 µEqv/L stock solutions were made by mixing equal volumes of two one-component stock solutions. The Na+HTTFA solution consisted of equal volumes of the NaTTFA-EtOH and the HTTFA-EtOH solutions. The Gd+HTTFA solution consisted of equal volumes of the Gd(TTFA)$_3$-EtOH and the HTTFA-EtOH solutions. And the Gd+Na(TTFA) solution consisted of equal volumes of the Gd(TTFA)$_3$-EtOH and the Na(TTFA)-EtOH solutions. For each of these One-to-One solutions, the concentrations of the TTFA anion, of the HTTFA molecule, or of their sum were 30,000 µEqv/L, 3,000 µEqv/L, 300 µEqv/L, and 30 µEqv/L.
 (e) The three One-to-One solutions were each added to 3 wells (30 µL per well). Two of the three aliquots of each set were added to a EuMac-Streptavidin-coated wells and the third to a control well.
 (f) Steps (i), (j), and (k) of the procedures of EXAMPLE X were repeated.
 (g) The data points from the two EuMac-Streptavidin-coated wells of each set were averaged and the luminescence from the control well was subtracted. These averaged net results are shown in Table 4 and FIG. 8. The results for the wells treated with the One-to-One solutions are shown on the left and those for the wells treated with the one-component solutions are shown on the right of Table 4. The maximum net luminescence occurred at the second highest concentration, 3,000 µEqv/L, for both One-to-One solutions containing Gd(III), namely the Gd+HTTFA and the Gd+Na(TTFA) solutions. The difference between these two values (109.0 and 103.3) is within the error of the experiment. Both of these values are greater than the maximum value (62.5) for the one-component Gd(TTFA)3 solution, which also occurs at 3,000 µEqv/L, and are over 4 times the maximum values for the HTTFA (22.0), NaTTFA (16.0), and the Na+HTTFA One-to-One solution (26.0), which occurred at the highest concentration, 30,000 µEqv/L.

TABLE 4

| TTFA µEqv/L | One-to-One Solutions | | | One-Component Solutions | | | TTFA nEqv per well |
|---|---|---|---|---|---|---|---|
| | Na + HTTFA | Gd + HTTFA | Gd + Na (TTFA) | HTTFA | Na (TTFA) | Gd (TTFA)$_3$ | |
| 30,000 | 26.0 | 38.7 | 80.0 | 22.0 | 16.0 | 10.6 | 900 |
| 3,000 | 18.3 | 109.0 | 103.3 | 16.0 | 15.8 | 62.5 | 90 |
| 300 | 14.2 | 32.1 | 31.8 | 11.3 | 11.7 | 29.6 | 9.0 |
| 30 | 12.7 | 12.7 | 13.3 | 7.9 | 8.7 | 8.8 | 0.90 |

(h) As in EXAMPLE X and in EXAMPLE XI, increasing the concentration of the TTFA anions or of the HTTFA molecules results in an increase in luminescence and the addition of Gd(III) can modulate the luminescence, in this case by increasing it. The presence of Gd(III) can also change the concentration of the TTFA anion and/or the HTTFA molecule where maximum luminescence occurs. Unexpectedly, the One-to-One mixtures of Gd(TTFA)$_3$ with either HTTFA or Na(TTFA) both have increased luminescence compared to the One-Component solutions of Gd(TTFA)$_3$ and Na(TTFA). Since at these concentrations of Na(TTFA) the ligand binding sites of the EuMac are fully saturated by TTFA ligands, the excess TTFA anions must have been a significant source of the energy emitted by the EuMac. The increase in emission resulting from the presence of the Gd(III) again provides evidence that this ion can modulate the efficiency of energy transfer from the TTFA anion and from the HTTFA molecule. The increased emission from the One-to-One mixture of Gd(TTFA)$_3$ with Na(TTFA) at the highest concentration demonstrates that changes in the ratio of cations can modulate, in this case increase, the emission from the EuMac. Unexpectedly, as shown in Table 4, the relative net luminescence of the One-Component solutions with molecular HTTFA is approximately equal to that of the NaTTFA. Thus, the excess HTTFA transfers energy by a means other than homogeneous resonance energy transfer to the EuMac. In this regard the HTTFA is behaving like a standard fluorophore or lumiphore or both. This finding opens the possibility of a new means for energy transfer to LnMacs and other energy transfer acceptor lanthanide(III) complexes, utilizing conventional including commercially available, fluorophores or lumiphores as energy transfer donors. Thus the HTTFA, Na(TTFA), and Gd(TTFA)$_3$ containing solutions and their mixtures are unitary luminescence enhancing solutions.

Example XIII

Enhancement of EuMac and TbMac Luminescence by the Addition of Methanolic Solutions Containing Na$_2$PDCA or Na$_3$Gd(PDCA)$_3$ A. Materials
(a) Sodium hydroxide, NaOH, ACS Grade (EM Science, Affiliate of Merck KGaA, Darmstad, Germany, Catalog No. SX 0590-1).
(b) The 2,6-pyridinedicarboxylic acid, H$_2$PDCA, of the Most Commonly Used Materials.
(c) Na$_2$PCDA-MeOH($10^{-3}$) is a 5.0×$10^{-3}$ M solution of Na$_2$PCDA in methanol. This solution was prepared as follows. The H$_2$PDCA (167.7 mg, 1.00 mmol) was dissolved in 25.0 mL of methanol to give a 4.03×$10^{-2}$ M solution. The NaOH (167.9 mg, 4.20 mmol) was dissolved in 100.0 mL of methanol to give a 4.20×$10^{-2}$ M solution. Then 1.25 mL of the H$_2$PDCA solution and 2.50 mL of the NaOH solution were mixed and the volume was brought up to 10.0 mL with methanol; 5.00 mL of the resulting solution were finally diluted to a total volume of 10.00 mL with methanol.
(d) Na$_2$PCDA-MeOH($10^{-4}$) is a 5.0×$10^{-4}$ M solution of Na$_2$PCDA in methanol. This was prepared by diluting 1.00 mL of the Na$_2$PCDA-MeOH($10^{-3}$) solution to a total volume of 10.0 mL with methanol.
(e) The Na$_3$Gd(PCDA)$_3$ of EXAMPLE IV.
(f) The EuMac-MeOH is a 10.5 µM solution of EuMac-un in methanol.
(g) The TbMac-MeOH is a 10.8 µM solution of ThMac-un in methanol.
(h) The Na$_3$Gd(PCDA)$^3$-MeOH($10^{-3}$) is a 3.48×$10^{-3}$ M solution of Na$_3$Gd(PCDA)$_3$ in methanol, equivalent to 1.04×$10^{-2}$ Eqv/L solution of the PDCA anions.
(i) The Na$_3$Gd(PCDA)$_3$-MeOH($10^{-4}$) is a 3.48×$10^{-4}$ M solution of Na$_3$Gd(PCDA)$_3$ in methanol, equivalent to 1.04×$10^{-3}$ Eqv/L solution of the PDCA anions.
(j) White, "U" bottomed, 96 well, microtiter plates (Thermo Electron Corp. (Franklin, Mass., part no. 7105).
(k) Culture tubes, disposable, 13×100 mm (VWR Scientific Products International, West Chester, Pa. 19380, Catalog No. 60825-414).

B. Procedure

For these studies, the EuMac-MeOH solution and TbMac-MeOH solution were employed in exactly the same manner. Hence the general term LnMac-MeOH will be employed in some of the following when describing steps in procedure that are identical and are performed separately with each LnMac-MeOH solution.
(a) 1 mL of the EuMac-MeOH solution was added to each of six test tubes (Eu set) and 1 mL of the TbMac-MeOH solution was added to each of six test tubes of another set (Tb set). The test tubes in each set were labeled 1-6 for identification. No Na$_2$PCDA-MeOH was added to Test tubes 1, which served as control. The following volumes of the Na$_2$PCDA-MeOH($10^{-4}$) solution: 100 µL, 200 µL, and 1,000 µL, were added, respectively, to test tubes 2, 3, and 4 of both the Eu and the Tb set. The following volumes of the Na$_2$PCDA-MeOH($10^{-3}$) solution: 200 µL and 300 µL, were added, respectively, to test tubes 5 and 6 of both the Eu and the Tb set. The solution in each test tube was brought up to a total volume of 2 mL with methanol, to produce two sets of six solutions each having essentially the same concentration of EuMac-un (5.05 µM) or ThMac-un (5.15 µM) and increasing concentrations of Na$_2$PCDA (0.00 µM, 25.0 µM, 50.0 µM, 251 µM, 501 µM, and 752 µM). For Na$_2$PCDA, the concentration of material expressed as Eqv/L of anion is equal to that expressed as molarity.

(b) Seven 250 mL aliquots were taken from each of the twelve Ln-Mac-Na$_2$PCDA-MeOH solutions of step (a) and added to individual wells of the U bottom plates. This resulted in an array of six sets each for EuMac-Na$_2$PCDA and TbMac-Na$_2$PCDA, each consisting of seven wells. All wells contained the same quantity of EuMac-un (1.26 nmol) or ThMac-un (1.29 nmol), but the quantity of Na$_2$PCDA increased in the order 0.0 nmol, 6.3 nmol, 12.5 nmol, 62.6 nmol, 125 nmol, and 188 nmol. For Na$_2$PCDA, the quantity of material expressed as Eqvs of anion is equal to that expressed as moles of Na$_2$PCDA. The solutions were allowed to dry by storing the plates at room temperature, in the dark, for 24 hr.

(c) 1 mL of the EuMac-MeOH solution was added to each of six test tubes (Eu set) and 1 mL of the ThMac-MeOH solution was added to each of six test tubes of another set (Tb set). The test tubes in each set were labeled 1-6 for identification. No Na$_3$Gd(PCDA)$_3$ was added to Test tubes 1, which served as control. The following volumes of the Na$_3$Gd(PCDA)$_3$(10$^{-4}$) solution: 200 μL and 1000 μL, were added, respectively, to test tubes 2 and 3 of both the Eu and the Tb set. The following volumes of the Na$_3$Gd(PCDA)$_3$(10$^{-3}$) solution: 200 μL, 300 μL, and 400 μL, were added, respectively, to test tubes 4, 5 and 6 of both the Eu and the Th set. The solution in each test tube was brought up to a total volume of 2 mL with methanol, to produce two sets of six solutions each having essentially the same concentration of EuMac-un (5.05 uM) or ThMac-un (5.15 μM) and increasing concentrations of the PCDA anion (0.0 μEqv/L, 104 μEqv/L, 520 μEqv/L, 1,040 μEqv/L, 1,560 μEqv/L, and 2,080 μEqv/L). For these solutions, the concentration expressed as Eqv/L of PCDA anion is equal to three times the concentration expressed as molarity of Na$_3$Gd(PCDA)$_3$ complex.

(d) Seven 250 μL aliquots were taken from each of the twelve five LnMac-Na$_3$Gd(PCDA)$_3$ solutions of step (c) and added to individual wells of the U bottom plates. This resulted in two arrays of six sets, each consisting of seven wells. All wells contained essentially the same quantity of EuMac-un (1.26 nmol) or TbMac-un (1.29 nmol), but the quantity of but the quantity of PCDA ligand, as part of the Na$_3$Gd(PCDA)$_3$ complex increased in the order 0.00 nEqv, 26 nEqv, 130 nEqv, 260 nEqv, 390 nEqv, and 520 nEqv. The solutions were allowed to dry by storing the plates at room temperature, in the dark, for 24 hr.

(e) The dry plates were mounted on the Cary Eclipse microplate reader and scanned. The luminescence emission spectra of the solid residues were obtained with a Varian Cary fluorometer operated in time-gated luminescence mode with a delay of 100 μsec. Fifty emission spectra were summed to produce the final spectrum. The excitation and emission slits were respectively 10 and 2.5 nm.

(f) Four sets of data were measured: EuMac-un with Na$_2$(PDCA) and with Na$_3$Gd(PDCA)$_3$, and ThMac-un with Na$_2$(PDCA) and with Na$_3$Gd(PDCA)$_3$.

(g) The emission intensity data from the aliquots of the methanolic solutions of each test tube were averaged. In FIG. 9a and FIG. 9b, the data for the EuMac-un has been reported as the average of the values between 612-621 nm and the data for the ThMac-un has been reported as the average of the values between 540-550 nm.

(h) The abscissa of FIG. 9a is the ratio between the equivalents of PDCA anions (3× the molarity of the Na$_3$Gd (PDCA)$_3$) and the moles of the lanthanide macrocycles. Unexpectedly, the presence of excess of the PDCA anion significantly increases the luminesce after both the EuMac-un and the ThMac-un (FIG. 9a) were already saturated by PDCA. The simplest possible explanation is that the excess PDCA anions, while not bound to the LnMac-un, can excite the LnMac-bound PDCA anions by homogeneous resonance energy transfer. Another possible explanation is that the unbound PDCA anions can transfer energy directly to the lanthanide ions of the LnMac-un complexes.

(i) The abscissa of FIG. 9b is the ratio between the equivalents of PDCA anions (3× the molarity of the Na$_3$Gd (PDCA)$_3$) and the moles of the lanthanide macrocycles. The ordinates (Relative Luminescence) of FIGS. 9a and 9b are in the same units. As shown in FIG. 9b, the presence of excess of the PDCA anions from the Na$_3$Gd (PDCA)$_3$ significantly increases the luminesce of the EuMac-un (circles) and the TbMac-un (squares), after both are already saturated by PDCA. This demonstrates that the excess PDCA anions in the presence of Gd(III), while not bound to the LnMac-un, can excite the LnMac-bound PDCA anions by homogeneous resonance energy transfer and/or the unbound PDCA anions can transfer energy directly to the lanthanide ions of the LnMac-un complexes.

(j) Each pair of points from the EuMac-un and the TbMac-un in the graphs of the luminescence increase resulting from the additions of the Na$_2$(PDCA) solution (FIG. 9a) and of the luminescence increase resulting from the additions of the Na$_3$Gd(PDCA)$_3$ solution (FIG. 9b) solutions shows the luminescence for samples having the same ratios of Eqv/L of PDCA anions to moles of LnMac. As opposed to the results obtained in the studies with TTFA described in Table 3a of EXAMPLE XI, the inclusion of Gd(III) decreases the luminescence enhancing effect of the PCDA anions for the EuMac-un. However, the inclusion of Gd(III) increases the luminescence of the TbMac-un while increasing the concentration of the anion required to maximize luminescence. Thus, in samples containing PDCA the replacement of the sodium cation by the gadolinium cation can selectively modulate the relative luminescence of lanthanide macrocycles. This effect may be related to the lanthanide ion, (Gd(III), modulating the energy or other property of electronic levels in the excited PDCA anion prior to the transfer of energy to the acceptor.

(k) The presence of Gd(III) resulted in an unexpected decrease of the luminescence of the EuMac and only in a small increase of the luminescence of the TbMac. This finding that excess ligand anions, in the absence of a second Ln(III) as energy transfer donor, can increase the luminescence of the energy transfer acceptor LnMac, has great utility in that it provides a new means to increase the luminescence of the bound LnMac labels without the increase in background brought about by the presence of the energy transfer donor lanthanide or other metal ion, particularly any Ln(III) contaminant. Thus the Na$_2$(PDCA) and Na$_3$Gd(PDCA)$_3$ containing solutions are unitary luminescence enhancing solutions.

Example XIV

Procedures for the Simultaneous Use of Two Lanthanide Labels

A. Materials
(a) The Gd(TTFA)$_3$-EtOH of EXAMPLE V.
(b) The Na(TTFA)-EtOH of EXAMPLE XI.
(c) The Na$_2$PCDA-MeOH of EXAMPLE XIII.

(d) The Na$_3$Gd(PDCA)$_3$-MeOH of EXAMPLE XIII.
(e) The Na$_2$(PDCA)-MeOH of EXAMPLE XIII.

B. Procedure
(a) For new types of preparations that are labeled with two or more LnMacs, the receiving surface member is covered with an amount, determined by experimentation, of a unitary luminescence enhancing solution which is then allowed to air dry. For instance, if the labels are the EuMac and the SmMac, the unitary solution contains either the Gd(TTFA)$_3$-EtOH or the Na(TTFA)-EtOH, or a mixture of the two. If the labels are the EuMac and the ThMac, the unitary solution contains either the Na$_3$Gd (PDCA)$_3$-MeOH or the Na$_2$(PDCA)-MeOH, or a mixture of the two. For each of the unitary solutions, the relationship between concentration and maximum net luminescence of the LnMac label is determined following the procedures of EXAMPLE XI, with the following substitution: a receiving surface member where a Ln-labeled-material is bound to one or more specific, relocatable positions is used instead of the wells of the Microwell Strip Plates with bound EuMac-streptavidin.

Example XV

Microscopic Visualization of LnMac Stained Cells and/or Other Materials with Excitation by Light with Emissions Below 330 nm A. Procedure
(a) Other luminescent lanthanide ions, such as terbium (III), can be visualized with a fluorescence microscope, provided that they are dried from the appropriate unitary luminescence enhancing solution. In the case of terbium (III), unitary solutions such as those described in EXAMPLE XIII are employed. Since the conditions of EXAMPLE XIII included excitation at 280 nm, the fluorescence microscope is modified so that all elements that transmit excitation light are fabricated from fused silica or materials with similar optical transmission. A light source that emits at 280 nm is employed. A 280 nm excitation filter and a dichroic mirror efficiently reflects 280 nm light and transmits light above 400 nm are used. The emission filter for Tb(III) is centered at 545 nm with a bandwidth of ±10 nm.

Example XVI

Preparation of the EuMac-Anti-5-BrdU

A. Materials
(a) The bicarbonate-carbonate buffer of the Most Commonly Used Materials.
(b) The TBS-Azide of the Most Commonly Used Materials.
(c) Dimethylformamide, DMF, Spectrophotometric Grade (Alfa Aesar, Ward Hill, Mass., Catalog No. 13808).
(d) EuMac-mono-NCS of the Most Commonly Used Materials, as solution in DMF (10.8 mg/ML).
(e) The 1.5 M NH$_2$OH.HCl (pH8.5) solution of the most commonly used materials.
(f) 5-bromo-uridine (5-BrdU), (Sigma, St. Louis, Mo., Catalog No. 5002), diluted to 3 mg/mL in H$_2$O.
(g) Coupling solution is an aqueous solution containing: 11.3 mg/mL of the anti-5-BrdU of the Most Commonly Used Materials, 150 mM NaCl, 20 mM NaHCO$_3$, and 0.05% NaN$_3$ (pH 8.5).
(h) The 50 mM NaHCO$_3$ (pH 8.6) of EXAMPLE VIII.

B. Procedure
(a) The conjugation of the EuMac-mono-NCS followed the description given in Ref. 31.
(b) 442.48 µL of the coupling solution was mixed with 44.25 µL of the 50 mM NaHCO$_3$ (pH 8.6) in a 2 mL plastic tube with cap, and equipped with a magnetic micro-stir bar. A ten molar excess of 5-BrdU (35.9 µL at 3 mg/mL) was added to the plastic vial to protect the combining site of the anti-5-BrdU. The EuMac-mono-NCS in DMF (130.66 µL of a 10.8 mg/mL solution) was then added to give a nominal (50:1) lumiphore-to-protein ratio. The solution was incubated for 60 min at room temperature, ca. 27° C.
(c) After 60 min., any remaining isothiocyanate was destroyed by the addition of 1.11 µL of the 1.5 M NH$_2$OH.HCl (pH8.5) solution (pH 8.5), corresponding to a 1:1 molar ratio to the original EuMac-mono-NCS.
(d) After an additional 30 min to complete the quenching reaction, the solution was transferred to a 1.5 mL centrifuge tube. The reaction vial was rinsed with 10 µL of TBS-Azide, and the rinse was added to the centrifuge tube. This was followed by centrifugation for 2 min at 17,000 (Hermle Z 180 M microcentrifuge) to remove any precipitate that may have formed during the conjugation.
(e) The clear solution was transferred to another vial and purified by size-exclusion chromatography on Sephadex G-25 in an XK16 column (Amersham Biosciences), using TBS-Azide as the eluent and a UV detector. The solvent front (~11 mL) containing the first absorption peak was collected in TBS-Azide and concentrated using a 10,000 molecular weight cut off filter (Millipore, Catalog No. PBGC02510) with a 3 mL stir cell (Millipore model 8003, Catalog No. 5125) under inert gas pressure. Helium was used in this experiment.
(f) The UV spectra of the conjugate and of anti-5-BrdU were obtained in TBS-Azide pH 7.25 buffer.
(g) As shown in FIG. 10, the EuMac-anti-5-BrdU conjugate had a strong absorption at 250-260 nm, and a comparison between the absorbance of the conjugate and that of the EuMac-mono-NCS confirmed the presence of coupled europium macrocycles. A perfect matching of the spectra would not be expected since the isothiocyanate group of the EuMac-mono-NCS is replaced during coupling by a thiourea group, and the spectrum of the EuMac-mono-NCS was obtained in DMF.

Example XVII

Preparation of the SmMac-Anti-5-BrdU and Other LnMac-Anti-5-BrdU

A. Materials
(a) The SmMac-mono-amine is synthesized according to the procedures of Example VIII of U.S. Pat. No. 5,696, 240, with the substitution of samarium acetate for lanthanum acetate. The SmMac-mono-amine is converted to the SmMac-mono-NCS according to the procedures of Example XXXVI B, Step 1, of U.S. Pat. No. 5,696, 240. The SmMac-mono-amine preparation used to synthesize the isothiocyanate includes: 34% SmMac-mono-amine, 66% unfunctionalized SmMac and virtually no SmMac-di-amine. Thus, the contamination of the cross-linking di-isothiocyanate is minimal. The unfunctionalized macrocycle contaminant should only act as a diluting, inert species.

B. Procedure
(a) The procedures of EXAMPLE XVI are followed with the substitution of the SmMac-mono-NCS or other LnMac-NCS for the EuMac-mono-NCS.
(b) The relative absorbance of the SmMac-anti-5-BrdU or other LnMac conjugate shows a contribution of the SmMac spectrum, in that it is higher than the absorbance of the anti-5-BrdU in the regions between 240 to 270 nm and beyond 290 mn. This shows the presence of SmMac-mono-NCS or other LnMac-mono-NCS coupled to the anti-5-BrdU.

Example XVIII

Preparation of the TbMac-Anti-5-BrdU

A. Materials
(a) The ThMac-mono-amine is synthesized according to the procedures of Example VIII of U.S. Pat. No. 5,696,240, with the substitution of terbium acetate for lanthanum acetate. The ThMac-mono-amine is converted to the TbMac-mono-NCS according to the procedures of U.S. Pat. No. 5,696,240, EXAMPLE XXXVI B, Step 1. The TbMac-mono-amine preparation that is used to synthesize the isothiocyanate used for these studies includes: 34% TbMac-monoamine, 66% unfunctionalized ThMac and virtually no ThMac-di-amine. Thus, the contamination of the cross-linking di-isothiocyanate is minimal. The unfunctionalized macrocycle contaminant should only act as a diluting, inert species.

B. Procedure
(a) The procedures of EXAMPLE XVI are followed with the substitution of the ThMac-mono-NCS for the EuMac-mono-NCS.
(b) The relative absorbance of the ThMac-anti-5-BrdU conjugate shows a contribution of the TbMac spectrum, in that it is higher than the absorbance of the anti-5-BrdU in the regions between 240 to 270 nm and beyond 290 nm. This shows the presence of ThMac-mono-NCS coupled to the anti-5-BrdU.

Example XIX

Luminescence Studies of EuMac-di-NCS Stained Cells Dried from a Gadolinium(TTFA)$_3$, Solution A. Materials.
(a) The EuMac-di-NCS of the Most Commonly Used Materials.
(b) A 134 μM solution of the Gd(TTFA)$_3$ of EXAMPLE II in ethanol, Gd(TTFA)$_3$-EtOH.
(c) The TBS-Azide of the Most Commonly Used Materials.
(d) The 1.5 M NH$_2$OH.HCl (pH8.5) solution of the Most Commonly Used Materials.
(e) HL60 (non-apoptotic) cells (Phoenix Flow Systems, San Diego, Calif., APO-BRDU™ Kit, Catalog No. CC1001).
(f) The Gd Rinse Buffer was based on the Phoenix Flow Systems rinse buffer (Ref. 32). The Gd Rinse Buffer consisted of: 10 mM TRIS, 150 mM NaCl, 0.1 mM GdCl$_3$, 0.25% (w/v) gelatin of the Most Commonly Used Materials, 7.7 mM NaN$_3$ and 0.1% v/v Triton X-100 of the Most Commonly Used Materials. After all components had been mixed, the pH was adjusted to 7.4 with HCl.
(g) The 5% PEG-EtOH solution of the Most Commonly Used Materials.
(h) Aminosilane treated slides of the Most Commonly Used Materials.
(i) Clearium Mounting Medium of the Most Commonly Used Materials.
(j) Bicarbonate buffer was an aqueous solution containing 150 mM NaCl and 20 mM NaHCO$_3$ (pH 8.6).

B. Procedure
(a) 1 mL of HL60 (non-apoptotic) cell suspensions (approximately 1×10$^6$ cells per 1 mL) was transferred to a 1.5 mL Eppendorf Tube of the Most Commonly Used Materials. The cell suspensions were centrifuged at 300 g for 5 min and the 70% (v/v) ethanol supernatant was removed by aspiration.
(b) The cell pellet was washed with 0.5 mL of TBS-Azide, centrifuged, and aspirated as before.
(c) The cell pellet was washed with 0.5 mL of bicarbonate buffer, centrifuged, and aspirated as before.
(d) The cell pellet was resuspended with 100 μL of the same buffer by pipetting up and down with a 200 μL pipette tip.
(e) 10 μL of 1 M NaHCO$_3$ pH 8.1 was added.
(f) 10 μL of EuMac-di-NCS in DMSO (3-5 mg/mL) was added and mixed by pipetting.
(g) The EuMac-di-NCS coupling solution was incubated at room temperature for 30 min in the dark.
(h) 5 μL of The 1.5 M NH$_2$OH.HCl (pH8.5) solution was added and the solution was mixed by pipetting.
(i) The reaction was quenched by incubating at room temperature for an additional 15-20 min.
(j) The cells were washed three times by addition 0.5 ML TBS-Azide, followed by centrifugation, and subsequent aspiration of supernatant.
(k) A pair of Leif Centrifugal Cytology Buckets (Ref. 33) (Newport Instruments) that fit a Beckman Coulter (Brea. Calif.) model GPR centrifuge, each of which holds 2 inserts, were assembled with aminosilane treated slides. Four chamber inserts were used.
(l) The cells were resuspended with 0.5 mL of Gd Rinse Buffer, or with the volume of buffer required to obtain the desired cell density for centrifugal cytology with the four chamber Leif Buckets.
(m) The cells were centrifuged at 300 g for 5 min in Leif Buckets and the supernatant was removed by aspiration.
(n) 100 μL of 5% PEG-EtOH solution was added to the fixative inlet of the centrifugal cytology sample chambers and sedimented onto the slide-attached cells by accelerating the centrifuge for approximately 30 sec. The supernatant was then removed by aspiration.
(o) The slides were removed from the Leif Buckets and rinsed twice with ethanol, each time tapping the slides on a paper towel to remove excess liquid. The slides were finally air dried.
(p) The cell monolayer was flooded with 2 drops of 134 μM Gd(TTFA)$_3$ in ethanol and air dried.
(q) The slide-bound cells were rinsed twice with ethanol, removing excess liquid each time, and then were allowed to air dry.
(r) 30 μL of Clearium Mounting Medium was pipetted onto the cell area, making sure that all cells were covered.
(s) The solvent was evaporated from the Clearium by mild heat generated with a heat gun.
(t) The cells were observed with a fluorescent microscope, under 365 nm excitation provided by a Hamamatsu L4634 flashlamp placed in a special housing (Ref. 13). The light passed through a UV DAPI cube, which did not include an emission filter. A removable, narrow bandpass 619 nm emission filter was located above the cube.

FIG. 11 shows two inverted images of the same field of EuMac-di-NCS stained cells that had been prepared by centrifugal cytology, treated with Gd(TTFA)$_3$-EtOH, and mounted and dried in Clearium. A 60× oil objective, NA 1.25, was used and the images were binned to 680×518 pixels. The flash lamp was used as the light source. FIG. 11A is an image of a single 5 seconds exposure of the CCD camera with the flash lamp operated at 50 Hz with a UV DAPI cube and 619 nm emission filter. FIG. 11B is the sum of one thousand 2 msec exposures of the CCD camera with the flash lamp operated at 8 Hz, a time delay of 29 μsec, and only a UV DAPI cube. A time delay system and software supplied by the manufacturer permitted the averaging of one thousand 2 msec exposures. According to the manufacturer, the Retiga-1350 EX has an approximately 9 μsec delay before opening its shutter. The total delay, 29 μsec, is the sum of camera delay and the 20 μsec delay produced by the special time-delay box. Similar time delay studies (Ref. 13) with cells stained with the fluorescein derivative, 6-(fluorescein-5-(and-6)-carboxamido)hexanoic acid succinimidyl ester (SFX mixed isomer), obtained from Molecular Probes (Eugene, Oreg., Catalog No. F-6129) have shown that this conventional organic fluorophore does not produce any detectable emission after this time-delay (data not shown). Thus, the use of a unitary luminescence enhancing solution for time-gated studies has been demonstrated.

Example XX

EuMac-di-NCS and DAPI Stained Cells

A. Materials.
(a) 4',6-Diamidino-2-phenylindole dihydrochloride, DAPI (Molecular Probes, Eugene, Oreg., Catalog No. D-1306).
(b) 10 μM DAPI solution in TBS-Azide, pH 7.4.
(c) All other materials are the same as those listed in EXAMPLE XIX B. Procedure
(a) The procedures of EXAMPLE XIX were followed and the cells were stained and mounted. The mounting medium was removed with toluene and the slide was rinsed twice with ethanol and allowed to dry.
(b) The cells were rehydrated by incubating under TBS-Azide for 5 min in a conical, graduated 50 mL tube (Fisher Scientific, part No, 05-539-6), making sure that the buffer covered the cells.
(c) The excess liquid was removed with Kimwipes and the cells were incubated with 50 μL of the 10 μM DAPI solution for 5 min.
(d) The DAPI stained cells were rinsed with TBS-Azide three times.
(e) The cells were rinsed twice with 50 μL ethanol and then air dried.
(f) Two drops of Gd(TTFA)$_3$ in ethanol (134 μM) were applied and allowed to dry.
(g) The cells were then rinsed twice with ethanol and air dried.
(h) The cells were covered with Clearium Mounting Medium and heat dried with mild heat from heat gun.

FIG. 12 shows four inverted images of the same field of cells stained sequentially with the EuMac-di-NCS and DAPI. The cells were prepared by centrifugal cytology, treated with Gd(TTFA)$_3$-EtOH, and mounted and dried in Clearium. A 60× oil objective, NA 1.25, was used and the cells were binned to 680×518 pixels. The excitation light was provided by the flashlamp and the special lamp housing (Ref. 13). Conventional images were obtained by opening the camera for a fixed time without time-gating.

Images A and B were obtained without the use of the time delay. Image A was obtained with the UV DAPI cube and the 619 nm narrow-band emission filter. The flashlamp was operated at 50 Hz and the time exposure was 40 sec. In this image, each cell is entirely stained by the EuMac-di-NCS. Image B was obtained with the UV DAPI cube and the DAPI 450 nm emission filter. The flashlamp was operated at 50 Hz and the exposure was for 8 sec. In this image, only the nucleus of the cell is stained by DAPI, which is specific for DNA. Although the light attenuation produced by the narrow band 619 nm filter decreased the light intensity, its use ensured that the image was only the result of the EuMac luminescence.

Images C and D were obtained with the use of a 29 μsec time delay. The flashlamp was operated at 8 Hz; and 760 two msec exposures were summed. Image C was obtained with the UV DAPI cube. The camera summation artifact in image (C) was reduced by the single use of the Adjust Remove background and Adjust Autolevel brightness filters from the Fovea PhotoShop plug-in (http://reindeergraphics.com). Image D was obtained with the UV DAPI cube and the DAPI 450 nm emission filter.

Except for the camera summation artifact, image (C) is identical with image (A); yet image (D) is blank. Since the DAPI emission has been extinguished after a 29 μsec delay, it can be concluded that the time-delayed image (C) only contains the europium macrocycle emission. Thus, the use of a unitary luminescence enhancing solution permits imaging including time-gated imaging of the luminescence from the EuMac and other lanthanide(III) complexes with similar lifetimes, such as the TbMac of EXAMPLE XIII, permits the simultaneous detection of conventional fluorophores such as DAPI, and permits the use of time-gating to eliminate any contamination of the EuMac emission by the strong emission produced by the conventional fluorophore.

Example XXI

SmMac-di-NCS Stained Cells

A. Materials.
(a) SmMac-di-NCS was synthesized according to U.S. Pat. No. 5,696,240, EXAMPLE XXIX B, Step 1.
(b) All other materials are the same as those listed in EXAMPLE XIX and EXAMPLE XX.

B. Procedure
The procedures of EXAMPLE XIX were followed with the substitution of the SmMac-di-NCS for the EuMac-di-NCS.

FIG. 13 shows two inverted images of SmMac stained cells that were prepared by centrifugal cytology, treated with Gd(TTFA)$_3$-EtOH, and mounted and dried in Clearium. A 60× objective, NA 1.25, was used and the images were binned to 680×518 pixels. A Hamamatsu L4634 flashlamp in a special housing was used as the light source. For FIG. 13A, the QIM-AGING Retiga-1350 EX CCD camera was kept open for 0.5 sec. with a flash rate of 50 Hz. The DAPI stained nuclei are clearly visible with good maintenance of nuclear detail. Except for one cell in the center near the top, the cytoplasm is not evident. The same microscopic field (FIG. 13B) was imaged employing a time delay of 29 μsec. FIG. 13B is the sum of eight images, each of which is the sum of one thousand 2 msec. time gated exposures with the flashlamp operated at 8 Hz. In order to avoid overflow artifacts, the Fovea Math. General filter was used to sum four pairs of images and to divide the values of the individual pixels by two. The four pairs were similarly processed to produce two pairs, which were again processed to produce one average image. The uneven background, camera artifact, was lessened by using the Fovea Remove Bkgrnd filter. The black and white levels were stretched by the use of the Fovea contrast filter to bracket the region of the monochrome distribution that contained a significant number of pixels. The luminescence of the samarium macrocycle was much weaker than that of the europium macrocycle. However, as demonstrated in EXAMPLE XX, the DAPI fluorescence is not detectable after a 29 µsec. delay; and the image consists of the total area of the SmMac-di-NCS stained cells. Thus, the use of a unitary luminescence enhancing solution permits imaging including time-gated imaging of the luminescence from the relatively weakly luminescent SmMac and other lanthanide(III) complexes with similar lifetimes, permits the simultaneous detection of conventional fluorophores such as DAPI, and permits the use of time-gating to eliminate any contamination of the SmMac emission by the strong emission produced by the conventional fluorophore.

Example XXII

Luminescence Studies of EuMac-di-NCS Stained Cells Dried from Yttrium(TTFA)$_3$ Solution A. Materials.
  (a) Y(TTFA)$_3$-EtOH is an ethanol solution containing 134 µM of the Y(TTFA)$_3$ of EXAMPLE III.
  (b) The materials of EXAMPLE XIX with the substitution of Y(TTFA)$_3$-EtOH for the Gd(TTFA)$_3$-EtOH of EXAMPLE XIX.
B. Procedure
  (a) The procedures of EXAMPLE XIX are followed with the substitution of Y(TTFA)$_3$-EtOH for the Gd(TTFA)$_3$-EtOH of EXAMPLE XIX.
  (b) The cells are observed with a fluorescence microscope under 365 nm excitation provided by a Hamamatsu L4634 flashlamp placed in a special housing (Ref. 13). The light passes through a UV DAPI cube, which does not include an emission filter. A removable, narrow band-pass 619 nm emission filter is located above the cube.

Two inverted images are obtained of the same field of EuMac-di-NCS stained cells that are prepared by centrifugal cytology, treated with Y(TTFA)$_3$-EtOH, and mounted and dried in Clearium. A 60× oil objective, NA 1.25, is used and the images are binned to 680×518 pixels. The flash lamp is used as the light source. A first image of a single 5 sec exposure of the CCD camera is obtained with the flash lamp operated at 50 Hz with a UV DAPI cube and 619 nm emission filter. A second image is the sum of sufficient 2 msec exposures of the CCD camera with the flash lamp operated at 8 Hz, a time delay of 29 µsec, and with only a UV DAPI cube. A time delay system and software supplied by the manufacturer permits the averaging of one thousand 2 msec exposures. According to the manufacturer, the Retiga-1350 EX has an approximately 9 µsec delay before opening its shutter. The total delay, 29 µsec, is the sum of camera delay and the 20 µsec delay produced by the special time-delay box. The conventional first and time-delayed second images are very similar. Thus, cofluorescence occurs with the substitution of yttrium (III) for gadolinium(III).

Example XXIII

Preparation of EuMac-Anti-5-BrdU Directly Stained Apoptotic Cells

A. Materials.
  (a) The EuMac-Anti-5-BrdU of EXAMPLE XVI.
  (b) The gelatin of the Most Commonly Used Materials.
  (c) The NaN$_3$ of the Most Commonly Used Materials.
  (d) The Triton X-100 of the Most Commonly Used Materials.
  (e) PFS Wash buffer (Phoenix Flow Systems, San Diego, Calif., Catalog No. ABWB13).
  (f) PBS-Azide is an aqueous solution containing 10 mM NaH$_2$PO$_4$, 150 mM NaCl, and 0.05% NaN$_3$.
  (g) The Gd rinse buffer of EXAMPLE XIX.
  (h) The Gd(TTFA)$_3$-EtOH of EXAMPLE XIX
  (i) The 5% PEG-EtOH solution of the Most Commonly Used Materials.
  (j) Fluorescein labeled anti-5-BrdU (Phoenix Flow systems, San Diego, Calif., Fluorescein-PRB-1 monoclonal antibody, Catalog No. ABFM18).
  (k) Positive and negative control apoptotic cells (Phoenix Flow Systems, San Diego, Calif., APO-BRDU™ Kit, Catalog Nos. CC1002 and CC1001, respectively).
  (l) The aminosilane treated slides of the Most Commonly Used Materials.
  (m) The Clearium Mounting Medium of the Most Commonly Used Materials.
B. Procedure
  (a) This direct staining procedure was based on the standard technique described in the Phoenix Flow Systems APO-BRDU™ Kit (Ref. 32). Parallel flow cytometry measurements with fluorescein labeled anti-5-BrdU permitted direct quality control for all of the reagents except the EuMac-mono-NCS labeled anti-5-BrdU. Parallel centrifugal cytology preparations were made with the fluorescein labeled proteins. The cells were allowed to air-dry from the ethanol, because the low surface tension of ethanol produces minimal morphological distortion.
  (b) A pair of Leif Centrifugal Cytology Buckets (Ref. 33) (Newport Instruments) that fit a Beckman Coulter (Brea. Calif.) model GPR centrifuge, each of which holds 2 inserts, were assembled with aminosilane treated slides. Four chamber inserts were used.
  (c) The DNA Labeling solution was prepared according to the APO-BrdU Protocol (Ref. 32).
  (d) 1 mL aliquots of the positive control cell suspensions (approximately 1×10$^6$ cells per 1 mL) were transferred to 12×75 mm Fisher Scientific flow cytometry centrifuge tubes. The positive control cell suspensions were centrifuged at 300 g for 5 min before removing the 70% (v/v) ethanol supernatant by aspiration.
  (e) The cells were washed twice with 1 mL of Phoenix Flow Systems wash buffer (Ref. 32). Each wash was carried out by centrifugation at 300 g for 5 min and the supernatant was removed by aspiration.
  (f) The apoptotic breaks were tailed with 5-BrdU by addition of 50 µL of DNA Labeling solution and incubation at 37° C. for 60 min.
  (g) The cells were then washed twice by centrifugation for 5 min with 0.5 mL of Gd rinse buffer, and the supernatant was removed as before.
  (h) The cell pellet was resuspended in 0.1 mL of a solution containing 40 µg/mL of EuMac-anti-5-BrdU in Gd rinse buffer. The tubes were wrapped with aluminum foil and incubated in the dark for 30 min at room temperature.

(i) After the 30 min incubation, 0.5 mL of the Gd Rinse Buffer was added to the staining solution. The cell suspension was centrifuged and the supernatant removed, as before.
(j) The wash treatment of step (i) was repeated.
(k) The cells were resuspended with 0.5 mL of Gd Rinse Buffer, or with the volume of buffer required to obtain the desired cell density for centrifugal cytology with the four chamber Leif Buckets.
(l) The cells were centrifuged at 300 g for 5 min in Leif Buckets and the supernatant was removed by aspiration.
(m) 100 µL of the 5% PEG-EtOH solution was added to the fixative inlet of the centrifugal cytology sample chambers and sedimented onto the slide-attached cells by accelerating the centrifuge for approximately 30 sec. The supernatant was then removed by aspiration.
(n) The slides were removed from the Leif Buckets, rinsed twice with ethanol and air dried.
(o) The cell monolayer was flooded with 2 drops of 134 µM Gd(TTFA)$_3$-EtOH and air dried.
(p) The slide-bound cells were rinsed twice with ethanol, removing excess liquid each time, and air dried.
(q) 30 µL Clearium Mounting Medium was pipetted onto the cell area, making sure that all cells were covered.
(r) The solvent was removed from the Clearium by mild heat generated with a heat gun.
(s) The cells were observed with a fluorescent microscope under 365 nm excitation provided by continuous illumination with a 100 watt mercury-xenon arc. The light passed through a UV DAPI cube, which did not include an emission filter, and then through a narrow band-pass 619 nm emission filter located above the cube. The exposure was 30 sec. A 60× oil objective, NA 1.25, was used and the image of the cells was binned to 640×518 pixels. The image shown in FIG. 14 was slightly over exposed in order to show the unlabeled cells.
(t) Therefore, as demonstrated by the detection of apoptosis, it has now been possible with only minimal changes from presently existing protocols to produce preparations of cells directly stained with europium labeled antibodies, and to obtain intensified emission from the stained cells after drying from a unitary luminescence enhancing solution containing a different lanthanide ion, in the presence of an amount of TTFA ligand in excess of that needed to complex with the EuMacs. The use of ethanol as the low surface tension solvent, ethanol, of the unitary luminescence enhancing solution and absence of the detergent required for formation and maintenance of the previous micellar Lanthanide Enhanced Luminescence solution (Refs. 5,6) resulted in the morphology of the cells remaining intact.

Example XXIV

Preparation of SmMac-Anti-5-BrdU or Other LnMac-anti-5-BrdU Directly Stained Apoptotic Cells A. Materials.
  (a) The SmMac-Anti-5-BrdU of EXAMPLE XVII or other LnMac-anti-BrdU.
B. Procedure
  (a) The procedures of EXAMPLE XXII are followed with the substitution of the of SmMac-Anti-5-BrdU or other LnMac-Anti-5-BrdU for EuMac-Anti-5BrdU.
  (b) The SmMac-Anti-5-BrdU labeled cells are observed with a fluorescence microscope under 365 nm excitation provided by continuous illumination with a 100 watt mercury-xenon arc. The light is passed through a LV DAPI cube, which does not include an emission filter, and then through a 630 to 660 nm, half maximum cut-off points, band-pass emission filter located above the cube. Test images are made to determine the optimum exposure time. A 60× oil objective, NA 1.25, is used and the image of the cells is binned to 640×518 pixels. The black and white levels of the image are stretched by the use of the Fovea contrast filter to bracket the region of the monochrome distribution that contains a significant number of pixels and are adjusted to weakly show the unlabeled cells.
  (c) Therefore, as demonstrated by the detection of apoptosis, it has now been possible with only minimal changes from presently existing protocols to produce preparations of cells directly stained with antibodies labeled with samarium(III) and to intensify their emission after drying from a unitary luminescence enhancing solution containing a different lanthanide ion in the presence of an amount of TTFA ligand in excess of that needed to complex with the EuMacs. The use of a low surface tension solvent, ethanol, permits air drying without impairing the morphology of the cells.
  (d) Alternatively, the composition of the unitary luminescence enhancement solution is optimized according to the procedures of EXAMPLE XIII.
  (e) Alternatively, the other LnMac-Anti-5-BrdU labeled cells are visualized according to the procedures of EXAMPLE XV.
  (f) Or, alternatively, an enhancer for terbium(III) or other lanthanide ion that excites above approximately 325 nm, and is suitable for use as a constituent of a unitary luminescence enhancing solution, can be employed with conventional microscope optics.

The use of ethanol as the low surface tension solvent, ethanol, of the unitary luminescence enhancing solution and absence of the detergent required for formation and maintenance of the previous micellar Lanthanide Enhanced Luminescence solution (Refs. 5,6) results in the morphology of the cells remaining intact.

Example XXV

Preparation of EuMac-Anti-5-BrdU Directly Stained S Phase Cells

A. Materials.
  (a) The EuMac-Anti-5-BrdU of EXAMPLE XVI.
  (b) The following components of the Phoenix Flow Systems (San Diego, Calif.) ABSOLUTE-S™ (Ref. 34):
    (i) 5-BrdU tailed cells, which are the Phoenix Flow Systems' Post UV irradiation reaction control cells, Part Number ASPC11. These cells have already formed DNA breaks that are tailed with 5-BrdU in the presence of TdT.
    (ii) Wash Buffer, Part Number ASWB15.
    (iii) Reaction Buffer, Part Number ASRXB16.
    (iv) TdT Enzyme, Part Number ASTD17.
    (v) Br-dUTP, Part Number ASBU18.
    (vi) The Fluorescein labeled anti-5-BrdU of EXAMPLE XXIII.
  (c) The Gd rinse buffer of EXAMPLE XIX.
  (d) The 5% PEG-EtOH solution of the Most Commonly Used Materials.
  (e) The Clearium Mounting Medium of the Most Commonly Used Materials.

B. Procedure

This direct staining procedure was based on the SBIP™ (Strand Break Induced Photolysis) technique (Ref. 35) described in the Phoenix Flow Systems ABSOLUTE-S™ Kit (Ref. 34). Parallel flow cytometry measurements with fluorescein labeled anti-5-BrdU permitted direct quality control for all of the reagents except the EuMac-mono-NCS labeled anti-5-BrdU. Parallel centrifugal cytology preparations were made with the fluorescein labeled antibody. The cells were allowed to air-dry from ethanol, because the low surface tension of ethanol produces minimal morphological distortion.

This protocol started with photolysis of the BrdU labeled DNA and is followed by tailing by the addition of 5-BrdU with terminal deoxytransferase.

(a) The 5-BrdU incorporated cells were resuspended by swirling the container containing the cells.

(b) 1 mL of the 5-BrdU incorporated cells was transferred to 12×75 mm tubes.

(c) The cells were centrifuged for 5 min. at 300 g followed by the removal of the supernatant by aspiration, being careful not to disturb the cell pellet.

(d) 2 mL of the Wash Buffer was added; the cells were resuspended and centrifuged for 5 min at 300 g, followed by the removal of the supernatant by aspiration, being careful not to disturb the cell pellet.

(e) The pellet was resuspended in 0.5 mL of Wash Buffer, making sure to free any cells that may have adhered to the tube sides during washing.

(f) The tube containing the cells was placed on the irradiating surface of the light box and illuminated for 5 min on high setting using a Fotodyne UV21 DNA transilluminator (Fotodyne inc., Hartland, Wis.).

(g) After illumination, 1 mL of Wash Buffer was added to the tubes; the cells were resuspended and then centrifuged for 5 min at 300 g, and the supernatant removed by aspiration, being careful not to disturb the cell pellet.

(h) The DNA Labeling Solution was prepared according to the vendor's instructions, depending on the number of assays being performed as described in the reference (Ref. 34). For example, 100 µL of TdT Reaction Buffer, 7.5 µL of TdT Enzyme, 80 µL of BrdUTP and 322.5 µL of distilled $H_2O$ were mixed together for a total volume of 510 µL.

(i) The photolysis induced breaks were tailed with 5-BrdU by the addition of 50 µL of DNA Labeling solution, and incubated for 60 min at 37° C. in a temperature controlled water bath. The cells were resuspended by shaking every 15 min.

(j) The cells were washed twice by centrifugation for 5 min with 0.5 mL of Gd rinse buffer, and the supernatant removed as before.

(k) The cell pellet was resuspended in 0.1 mL of 40 µg/mL of EuMac-anti-5-BrdU; the tubes were wrapped with aluminum foil and incubated in the dark for 30 min at room temperature.

(l) After the 30 min incubation, 0.5 mL of Gd Rinse Buffer was added to the staining solution. The cell suspension was centrifuged and the supernatant removed, as before.

(m) The wash treatment of step (1) was repeated.

(n) A pair of Leif Centrifugal Cytology Buckets (Ref. 33) (Newport Instruments) that fit a Beckman Coulter (Brea. Calif.) model GPR centrifuge, each of which holds 2 inserts, were assembled with aminosilane treated slides. Four chamber inserts were used.

(o) The cells were resuspended with 0.5 mL of Gd rinse buffer, or with the volume of buffer required to obtain the desired the cell density for centrifugal cytology with the four chamber Leif Buckets.

(p) The cells were centrifuged at 300 g for 5 min in Leif Buckets and the supernatant was removed by aspiration.

(q) 100 µL of 5% PEG-EtOH solution was added to the fixative inlet of the centrifugal cytology sample chambers and sedimented onto the slide-attached cells by centrifugation. The supernatant was then removed by aspiration.

(r) The slides were removed from the Leif Buckets, rinsed twice with ethanol and air dried.

(s) The cell monolayer was flooded with 2 drops of 134 µM $Gd(TTFA)_3$ in ethanol and air dried.

(t) The slide-bound cells were rinsed twice with ethanol, removing excess liquid each time, and air dried.

(u) 30 µL Clearium Mounting Medium was pipetted onto the cell area, making sure all cells were covered.

(v) The solvent was removed from the Clearium by mild heat generated with a heat gun.

(w) The cells were observed with a fluorescence microscope equipped with the 60× oil immersion lens. The 365 nm excitation was provided by continuous illumination with a 100 watt mercury-xenon arc. The exposure was for 30 sec. The light passed through a UV DAPI cube, which did not include an emission filter. A removable narrow band-pass 619 nm emission filter was mounted before the camera. The image shown in FIG. 15 was slightly overexposed to show the small dark granules in some of the cells, which are the islands of initial DNA synthesis. The image of the cells was binned to 680×518 pixels.

(x) Therefore, as demonstrated by the detection of S phase, it has now been possible with only minimal changes from presently existing protocols to produce preparations of cells directly stained with europium-labeled antibodies and to intensify their emission after drying from a unitary luminescence enhancing solution containing a different lanthanide ion.

The use of ethanol as the low surface tension solvent, ethanol, of the unitary luminescence enhancing solution and absence of the detergent required for formation and maintenance of the previous micellar Lanthanide Enhanced Luminescence solution (Refs. 5,6) resulted in the excellent morphology of the cells including the visualization of the islands of initial DNA synthesis.

Example XXVI

Preparation of SmMac-Anti-5-BrdU or Other LnMac-anti-5-BrdU Directly Stained S Phase Cells A. Materials (a) The SmMac-Anti-5-BrdU of EXAMPLE XVII or other LnMac-anti-5-BrdU.

A. Procedures.

(a) The procedures of EXAMPLE XXV are followed with the substitution of the SmMac-Anti-5-BrdU or other LnMac-anti-5-BrdU for the EuMac-Anti-5BrdU.

(b) The SmMac-Anti-5-BrdU labeled cells are observed with a fluorescence microscope equipped with the 60× oil immersion lens. The 365 nm excitation is provided by continuous illumination with a 100 watt mercury-xenon arc. Test images are made to determine the optimum exposure time. The light is passed through a UV DAPI cube, which does not include an emission filter. A removable 630 to 660 nm, half maximum cut-off points, band-pass emission filter is mounted before the camera. After the black and white levels are stretched by the use of the Fovea contrast filter to bracket the region of the monochrome distribution containing a significant number of pixels, the resulting image shows small dark granules in some of the cells. These are the islands of initial DNA synthesis. The image of the cells is binned to 680×518 pixels.

(c) Therefore, as demonstrated by the detection of S phase, it has now been possible with only minimal changes from presently existing protocols to produce preparations of cells directly stained with samarium-, europium- or other lanthanide-labeled antibodies, and to intensify their emission after drying from a unitary luminescence enhancing solution containing a different lanthanide ion.

(d) Alternatively, the other LnMac-Anti-5-BrdU labeled cells are visualized according to the procedures of EXAMPLE XV.

(e) Or, alternatively, an enhancer for terbium(III) or other lanthanide ion that excites above approximately 325 nm, and is suitable for use as a constituent of a unitary luminescence enhancing solution, can be employed with conventional microscope optics.

Example XXVII

Preparation of SmMac-Streptavidin

A. Materials.
(a) The SmMac-mono-NCS of EXAMPLE XVII.
(b) The 1.5 M $NH_2OH.HCl$ (pH 8.5) of the most commonly used materials.
(c) The Streptavidin of EXAMPLE VIII.

B. Procedure
(a) The procedures of EXAMPLE VIII are followed with the substitution of the SmMac-mono-NCS for the EuMac-mono-NCS.
(b) The UV spectrum of the conjugate has a strong absorption at 260 nm, which shows the presence of SmMac coupled to streptavidin.

Example XXVIII

Preparation of EuMac-Streptavidin Stained Apoptotic Cells to Which Biotin-Anti-5-BrdU had Been Bound A. Materials.
(a) The EuMac-Streptavidin of EXAMPLE VIII.
(b) Biotin-anti5-BrdU, the biotin conjugate of anti5-BrdU (Phoenix Flow Systems, San Diego, Calif., Catalog No. PRBBIOA).
(c) Materials b through m of EXAMPLE XXIII.

B. Procedure
(a) 1 mL aliquots of the control cell suspensions (approximately $1×10^6$ cells per 1 mL) were transferred to 12×75 mm Fisher Scientific or 1.5 mL Eppendorf tube (Brinkmann Instruments, Westbury, N.Y., Catalog No. 22 36 320-4) flow cytometry centrifuge tubes of the Most Commonly Used Materials. The positive control cell suspensions were centrifuged at 300 g for 5 min to remove the 70% (v/v) ethanol supernatant by aspiration.
(b) The cells were washed twice by centrifugation at 300 g for 5 min with 1 mL of the Phoenix Flow Systems wash buffer, followed by removal of the supernatant by aspiration.
(c) The apoptotic breaks were tailed with 5BrdU by addition of 50 µL of DNA Labeling solution and incubation at 37° C. for 60 min
(d) The cells were then washed twice by centrifugation for 5 min with 0.5 mL of Gd rinse buffer. The supernatant removed as before.
(e) The cell pellet was resuspended in 0.1 mL of 10 µg/mL Biotin-anti5-BrdU, the tubes were wrapped with aluminum foil and incubated in the dark for 30 min at room temperature.
(f) The biotin labeled cell suspension was washed twice with 0.5 mL Gd Rinse Buffer by centrifugation at 300 g for 5 min and the supernatant removed by aspiration, being careful not to disturb the cell pellet.
(g) The cell pellet was resuspended in 0.1 mL of a 40 µg/mL EuMac-Streptavidin staining solution, the tubes wrapped with aluminum foil, and incubated in the dark for 30 min at room temperature.
(h) After the 30 min incubation, 0.5 mL Gd Rinse Buffer was added to the staining solution. The cell suspension was centrifuged and the supernatant removed, as before.
(i) The wash treatment of step (h) was repeated.
(j) The cells were resuspended with 0.5 mL of Gd Rinse Buffer, or with the volume required to obtain the desired cell density for centrifugal cytology with the four chamber Leif Buckets.
(k) The cells were centrifuged at 300 g for 5 min. in Leif Buckets and the supernatant removed by aspiration.
(l) 100 µL of 5% PEG-EtOH solution was added to the fixative inlet of the centrifugal cytology sample chambers and sedimented onto the slide-attached cells by accelerating the centrifuge for approximately 30 sec. The supernatant was then removed by aspiration.
(m) The slides were removed from the Leif Buckets, rinsed twice with ethanol and air dried.
(n) The cell monolayer was flooded with 2 drops of 134 µM $Gd(TTFA)_3$-EtOH and air dried.
(o) The slide-bound cells were rinsed twice with ethanol, removing excess liquid each time, and air dried.
(p) 30 µL Clearium Mounting Medium was pipetted onto the cell area, making sure all cells were covered.
(q) The solvent was removed from the Clearium by mild heat generated with a heat gun.
(r) The cells were observed with a fluorescence microscope under 365 nm excitation provided by continuous illumination with a 100 watt mercury-xenon arc. The light passed through a UV DAPI cube, which did not include an emission filter, and then through a narrow band-pass 619 nm emission filter located above the cube. The exposure was 30 sec. A 60× oil objective, NA 1.25, was used and the images of the cells were binned to 640×518 pixels. The image shown in FIG. 16 is slightly over exposed in order to show the unlabeled cells.
(s) Therefore, as demonstrated by the detection of apoptosis, it has now been possible with only minimal changes from presently existing protocols to produce preparations of cells indirectly labeled with europium-labeled antibodies, and to intensify their emission after drying from a unitary luminescence enhancing solution containing a different lanthanide ion. The use of ethanol as the low surface tension solvent, ethanol, of the unitary luminescence enhancing solution and absence of the detergent required for formation and maintenance of the previous micellar Lanthanide Enhanced Luminescence solution (Refs. 5,6) resulted in the maintenance of the morphology of the cells.

Example XXIX

Preparation of EuMaC-Streptavidin Stained S Phase Cells to Which Biotin-Anti-5-BrdU has Been Bound A. Materials
(a) The EuMac-Streptavidin of EXAMPLE VIII.
(b) Biotin-anti5-BrdU, the biotin conjugate of anti5-BrdU (Phoenix Flow Systems, San Diego, Calif., Catalog No. PRBBIOA).
(c) Materials b through e of EXAMPLE XXV B. Procedure This indirect staining procedure was based on the direct SBIP™ (Strand Break Induced Photolysis) technique (Ref. 35) described in the Phoenix Flow Systems ABSOLUTE-S™ Kit (Ref. 34). This protocol starts with photolysis of the BrdU labeled DNA and is followed by tailing by the addition of 5-BrdU with terminal deoxytransferase.
(a) Procedures a through j of EXAMPLE XXV.
(b) Procedures e through q of EXAMPLE XXVIII.
(c) The cells were observed with a fluorescence microscope under 365 nm excitation provided by continuous illumination with a 100 watt mercury-xenon arc. The light passed through a UV DAPI cube, which did not include an emission filter, and then through a narrow band-pass 619 nm emission filter located above the cube. The exposure was 10 sec. A 60× oil objective, NA 1.25, was used and the image of the cells was binned to 640×518 pixels. The image is shown in FIG. 17.
(d) Therefore, as demonstrated by the detection of S phase, it has now been possible with only minimal changes from presently existing protocols to produce preparations of cells indirectly labeled with antibodies labeled with europium or other lanthanide ion and to intensify their emission after drying from a unitary luminescence enhancing solution containing a different lanthanide ion. The use of ethanol as the low surface tension solvent, ethanol, of the unitary luminescence enhancing solution and absence of the detergent required for formation and maintenance of the previous micellar Lanthanide Enhanced Luminescence solution (Refs. 5,6) resulted in the maintenance of the morphology of the cells

Example XXX

Measurement of Human Follicle Stimulating Hormone (FSH) in the Dry State

The procedures of Example XI of U.S. Pat. No. 6,340,744 (Ref. 5) are modified by the substitution of TRIS for hexamethylenetetramine, HMTA, and of the Gd(TTFA)$_3$-EtOH of EXAMPLE V for the optimized-cofluorescence matrix, followed by removal of the solvent.

A. Materials
(a) The EuMac-mono-NCS of the Most Commonly Used Materials.
(b) A monoclonal antibody, M94167, specific for the P-subunit of human FSH, commercially available from Fitzgerald Industries International, Inc., Concord, Mass., Catalog No. 10-F25, 1999.
(c) A monoclonal antibody, M607109, that recognizes a compatible epitope on human-FSH not located on the β-subunit of human FSH, commercially available from Fitzgerald Industries International, Inc., Catalog No. 10-F15. 1999.
(d) Intact human Follicle Stimulating Hormone (hFSH), commercially available from Fitzgerald Industries International, Inc., Catalog No. 30-AF25, 1999.
(e) Washing Buffer: In a IL volumetric flask, the following are added: 50 mmol (6 g) of the TRIS of the Most Commonly Used Materials), 154 mmol (9 g) of sodium chloride (Aldrich, St. Louis, Mo., Catalog No. 204439), 0.5 mL of Tween 20 (Aldrich, Catalog No. 27,434-8), and 900 mL of water. The solution is adjusted to pH 7.75 with hydrochloric acid and water is added to bring the volume to 1 L.
(f) Assay Buffer: In a 1 L volumetric flask, the following are added: 50 mmol (6 g) of TRIS of the Most Commonly Used Materials, 154 mmol (9 g) of sodium chloride (Aldrich, Catalog No. 204439), 5 g of bovine serum albumin (Sigma, St. Louis, Mo., Catalog No. B 4267), 0.5 g of bovine IgG (Sigma, Catalog No. I 5506), 0.1 g of Tween 40 (Aldrich, Catalog No. 27,435-6), and 900 mL of water. The solution is adjusted to pH 7.75 with hydrochloric acid and water is added to bring the volume to 1 L.

B. Procedure
(a) The derivatization, or conjugation, of the EuMac-mono-NCS with the M607109 monoclonal antibody is achieved by the procedures described in EXAMPLE XVI, with the replacement of the anti-5-BrdU of the Most Commonly Used Materials by the monoclonal antibody M607109. The europium-labeled M607109 is centrifuged for 2 min. at 17,000 g (Hermle Z 180 Microcentrifuge) to remove any antibody aggregates, and stored at 4° C. until use.
(b) Polystyrene microtiter strips (Immuno Module Maxisorp; Nalge Nunc International, Naperville, Ill., Catalog. No. 469914) are coated overnight, at 4° C., with 2 µg of the M94167 monoclonal antibody in 100 µL of PBS per well. Subsequently, the strips are incubated for 45 min at 37° C. with 200 mL of PBS containing bovine senum albumin (10 g/L) and then washed four times with the washing buffer.
(c) Graded amounts of the antigen (hFSH) in 100 µL of Assay Buffer are added to the M94167-coated wells and allowed to react on an orbit shaker at 500 rpm for 90 min at 22° C.
(d) The plates are washed six times with the washing buffer.
(e) 25 ng of europium-labeled M607109 in 100 µL of assay buffer are added to each well and the strips are incubated for 30 min at 22° C. on an orbit shaker (500 rpm).
(f) The plates are washed six times with the washing buffer.
(g) 100 µL of Gd(TTFA)$_3$-EtOH are added to each well and allowed to react with the intact europium-labeled M607109 for 10 min on an orbit shaker (500 rpm).
(h) The wells are air dried and the bottoms are cut-out
(i) The fluorescence is measured for 5 sec in a SLM-8000 fluorometer with the emission monochromator set at 618 nm and the emission slit adjusted to have a 10 nm band width at half maximum. The excitation is at 365 nm with a 16 nm band width at half maximum.
(j) The signal to noise ratio at 8 ng/L of FSH is higher than 1,000 and the maximum concentration measurable by the SLM-8000 exceeds 10,000 ng/L. Thus, the performance of the system described here is better than immunoenzymetric and immunoradiometric assays, even though it is slightly inferior to time-resolved immunofluorescence assays.
(k) In contrast to the examples given in Soini et al., U.S. Pat. No. 4,587,233, Method for Quantitative Determination of a Biospecific Affinity Reaction, 1986; and to the description of similar uses of lanthanide luminescent labels in I. Hemmila et al. (1994) (Ref. 37), because of the use of a unitary luminescence enhancing solution the analyte of this invention can be measured in a conventional fluorometer without requiring the additional steps of removal of the lanthanide(III) from a first complex and the formation of a second complex in solution prior to measurement. The performance of the system described here can be improved to be better than that of the DELFIA reagents which are optimized for the Arcus 1230. The signal is enhanced by the coating of the sample with $Gd(TTFA)_3$. Since the emitting species is bound to a solid surface, the depth of focus and optical volume of an instrument can be minimized, which in turn minimizes background noise from the solution.

Example XXXI

Time-Gated Measurement of Human Follicle Stimulating Hormone (FSH) in the Dry State A. Procedure
(a) The procedures of EXAMPLE XXX are repeated through step (g).
(b) The wells are air dried.
(c) The microtiter tray is mounted on Varian Cary Eclipse microplate reader accessory. Time-resolved fluorescence is measured for 1 sec in a Varian Cary Eclipse spectrofluorometer in time-gated mode. The emission monochromator is set at 618 nm and the emission slit adjusted to have a 10 nm band width at half maximum. The excitation is at 365 nm with a 16 nm band width at half maximum.
(d) In contrast to the examples given in Soini et al., U.S. Pat. No. 4,587,233, Method for Quantitative Determination of a Biospecific Affinity Reaction, 1986; and to the description of similar uses of lanthanide luminescent labels in I. Hemmila et al. (1994) (Ref. 37), because of the use of a unitary luminescence enhancing solution the analyte of this invention can be measured in a conventional fluorometer without requiring the additional steps of removal of the lanthanide(III) from a first complex and the formation of a second complex in solution prior to measurement. The performance of the system described here can be improved to be better than that of the DELFIA reagents which are optimized for the Arcus 1230. The signal is enhanced by the coating of the sample with $Gd(TTFA)_3$. Since the emitting species is bound to a solid surface, the depth of focus and optical volume of an instrument can be minimized, which in turn minimizes background noise from the solution.

Example XXXII

A Competitive Immunological Determination of Insulin in the Dry State

The procedures of Example XI of U.S. Pat. No. 6,340,744 (Ref. 5) are modified by the substitution of TRIS for HMTA, of the $Gd(TTFA)_3$-EtOH of EXAMPLE V for the optimized-cofluorescence matrix, and subsequent removal of the solvent.
A. Materials
(a) The EuMac-mono-NCS of the Most Commonly Used Materials.
(b) Insulin (Sigma Biochemicals and Reagents for Life Science Research, St. Louis, Mo., Catalog No. I 0259).
(c) A monoclonal antibody against human insulin (anti-insulin) is obtained from Fitzgerald Industries International, Inc., Concord, Mass., Catalog No. 10-I30, 1999).
(d) The Washing Buffer of EXAMPLE XXX.
(e) The Assay Buffer of EXAMPLE XXX.
B. Procedure
(a) The derivatization, or conjugation, of the EuMac-mono-NCS with insulin is achieved by the procedures described in EXAMPLE XVI, with the replacement of the anti-5-BrdU of the Most Commonly Used Materials by insulin. The europium-labeled insulin, EuMac-Insulin, is centrifuged for 2 min at 17,000 g (Hermle Z 180 Microcentrifuge) to remove any protein aggregates, and stored at 4° C. until use.
(b) Polystyrene microtiter strips (Immuno Module Maxisorp; Nalge Nunc International, Naperville, Ill., Catalog No. 469914) are coated overnight, at 4° C., with 2 µg of the anti-insulin monoclonal antibody in 100 µL of PBS per well. Subsequently, the strips are incubated for 45 min at 37° C. with 200 mL of PBS containing bovine serum albumin (10 g/L) and then washed four times with the washing buffer.
(c) 10 µL of EuMac-Insulin (20 ng) and 10 µL of insulin standards (0, 10, 50, 200, 1,000 and 10,000 ng) in 100 µL of Assay Buffer are added to the monoclonal antibody coated wells and allowed to react on an orbit shaker at 500 rpm for 90 min at 22° C.
(d) The plates are washed six times with the washing buffer.
(e) 100 µL of $Gd(TTFA)_3$-EtOH are added to each well and allowed to react with the EuMac-Insulin for 10 min on an orbit shaker (500 rpm).
(f) The wells are air dried.
(g) The microtiter tray is mounted on Varian Cary Eclipse microplate reader accessory. Time-resolved luminescence is measured for 1 sec in a Varian Cary Eclipse spectrofluorometer in time-gated mode. The emission monochromator is set at 618 nm and the emission slit adjusted to have a 10 nm band width at half maximum. The excitation is at 365 nm with a 16 nm band width at half maximum.
(h) According to the competitive determination principle (Ref. 36) the emission intensity of the sample decreases, as the amount of "cold" insulin increases.
(i) In contrast to the examples given in Soini et al., U.S. Pat. No. 4,587,233, Method for Quantitative Determination of a Biospecific Affinity Reaction, 1986; and to the description of similar uses of lanthanide luminescent labels in I. Hemmila et al. (1994) (Ref. 37), because of the use of a unitary luminescence enhancing solution the analyte of this invention can be measured in a conventional fluorometer without requiring the additional steps of removal of the lanthanide(III) from a first complex and the formation of a second complex in solution prior to measurement. The performance of the system described here can be improved to be better than that of the DELFIA reagents which are optimized for the Arcus 1230. The signal is enhanced by the coating of the sample with $Gd(TTFA)_3$. Since the emitting species is bound to a solid surface, the depth of focus and optical volume of an instrument can be minimized, which in turn minimizes background noise from the solution.

Example XXXIII

Comparative Genomic Hybridization

Introduction: The procedures for comparative genomic hybridization and analysis generally follow a course of nine broadly defined steps: (1) processing nucleic acid material including nucleic acids or oligonucleotides to generate populations of homogeneous nucleic acid fragments (typically complementary DNA, cDNA) suitable for printing onto substrate; (2) preparation of a receiving surface member with nucleic acid sequences of interest at one or more identifiable positions on a the receiving surface member; (3) isolation of two samples of nucleic acids from which hybridizing sample and reference specimens are derived; (4) synthesizing sample and reference cDNAs by copying either mRNA or DNA; (5) labeling sample and reference cDNAs with labels (presently fluorescent) that would permit them to be distinguished either during their synthesis or subsequent to their synthesis; (6) hybridizing a mixture of the labeled sample and reference cDNAs to the DNA sequences in the form of chromosomes or as an array of DNA containing spots on a receiving surface member; (7) preparation of the hybrids for visualization; (8) image acquisition of hybridization and (9) image analysis. The nucleic acid sequences of interest of step (2) can either exist as sequences present on chromosomes or as purified samples of polynucleotides.

The novel parts of the subsequent examples concern the labeling (step 5), preparation for visualization (step 7), and image acquisition (step 8). Since the rest of the procedures have been published as patents (Refs. 38, 39, 40, 41, 42, and 43), patent applications (Refs. 44, 45), articles (46, 47, 48), and web pages (Refs. 49, 50); these referenced CGH procedures are well understood by one of ordinary skill in the art.

As will be demonstrated by the following Examples, the labeling of sample and reference cDNAs with an energy transfer acceptor lanthanide(III) complex can either be performed for a direct assay where the complex is covalently bound to the cDNA or for an indirect assay where the energy transfer acceptor lanthanide(III) complex is bound to an analyte-binding species that is specific for a label. Besides the standard labels, such as biotin, this label can be a modified nucleotide, such as 5-BrdU.

Example XXXIV

Preparation of eDNA Labelled with a LnMac

The covalent labeling of DNA with a fluorophore or lumiphore can be performed by: 1) covalent coupling of the label to a nucleotide and subsequent enzymatic incorporation of the nucleotide into cDNA (Ref. 51); 2) enzymatic incorporation of a nucleotide with a reactive functionality into cDNA and subsequent covalent coupling of a label with the reactive functionality (Refs 52 and 53); and 3) covalent attachment of a preformed labeled carrier (Ref. 54)

A. Materials
(a) The EuMac-5-deoxyuridine triphosphate (Formula V) of EXAMPLE XXI of U.S. Pat. No. 6,340,744.
(b) The SmMac-5-deoxyuridine triphosphate of EXAMPLE XXI of U.S. Pat. No. 6,340,744.
(c) The procedure of EXAMPLE XXI of U.S. Pat. No. 6,340,744 is repeated with the replacement of the europium(III) by terbium(III) to produce TbMac-5-deoxyuridine.
(d) Venipuncture Human blood sample obtained from a volunteer.
(e) PUREGENE® DNA Purification Kit for whole blood or bone marrow (Gentra Systems Inc., Minneapolis Minn., Catalog No. D-5500).
(f) Human Genomic DNA (Promega, Madison Wis., Female Catalog No. G1521; Male Catalog No. G1471).
(g) SYBR® Gold Nucleic Acid Gel Stain (Catalog No. S-11494)
(h) Aminoallyl-dUTP sodium salt (aa-dUTP) Sigma, Catalog No. A0410

B. Procedure
(a) Genomic DNAs are extracted from the leukocytes present in the blood using the Puregene DNA Purification Kit. From 0.4 mL, approximately 150 µg DNA is prepared. Alternatively, human genomic DNA is purchased from Promega.
(b) The DNA is sonicated prepared for labeling as described in Ref. 50 Section 6.0, "Labeling of DNA using Random Priming" steps 1 through 5. After sonication, the number of base pairs for the fragments determined by electrophoresis on a small 1% agarose gel should range from 300 to 2000.
(c) The samples are stored at −80° C.
(d) The DNA samples are denatured by boiling for 5 minutes on a heat block at 95° C., and then are snapped cooled on ice for 10 minutes.
(e) Covalent labeling of an oligonucleotide with a LnMac: The procedures of Tasara et al. (Ref. 51) for the production of labeled templates are followed with the substitution of a LnMac-dUTP for the modified dNTP analogs employed by Tasara et al., including those described in Ref. 51. Alternatively, the "Labeling of DNA using Random Priming" protocol of the Jan Dumanski's Research Group (Ref. 50) can be employed with the replacement of the cyanine dye labeled DNTP with a LnMac-dUTP.
(f) The LnMac-mono-NCS is covalently coupled to nucleotides that have previously been incorporated with a reactive functionality. DeRisi described (Ref. 53) the incorporation by reverse transcriptase of the sodium salt of 5-[3-amino-allyl]-2'-deoxyuridine 5'-triphosphate (aa-dUTP) into cDNA. The intensity of the labeling depends upon the ratio of dTTP to aa-dUTP, with ratios between 1:1 and 3:2 being suitable for labeling first-strand yeast or mammalian cDNA. A second sample of this cDNA is subsequently labeled with Fluorolink Cy3 and Cy5 Monoreactive Dye-5 Packs (Amersham Biosciences). The procedure of DeRisi is followed with the substitution of LnMac-mono-NCS for the cyanine succinimidyl esters. In contradistinction to the findings of Randolph and Waggoner (Ref. 52), the luminescence increases in proportion to the number of LnMacs incorporated.
(g) Oligonucleotides carrying LnMac-labeled-polypeptide tails are synthesized according to the procedures of EXAMPLE XII of PCT WO 01/27625 A1 (Ref. 55).
(h) The preferred procedure from (e), (f), and (g) will be determined by electrophoretic separation of the EuMac labeled, single stranded products produced by the 3 procedures. The composition of the gel depends on the size of the DNA. For human DNA produced by the above procedures, 1% agarose is a reasonable starting concentration. The first gel is washed twice for 10 minutes in ethanol, transferred to Gd(TTFA)$_3$-EtOH, incubated for 15 minutes, and dried. A control gel is also stained by this procedure. The second EuMac labeled DNA-containing gel is stained according to the manufacturer's instructions with diluted SYBR Gold. A control gel is also stained by this procedure.

The first gel containing the EuMac labeled DNA and its control gel are inserted into a UVP Epi Chem II Darkroom and are illuminated with the long UV (ca. 365 nm) bulb and the Eu(III) emission is detected at 619 nm. The second gel containing the EuMac labeled DNA and its control gel are inserted into a UVP Epi Chem II Darkroom and are illuminated at 254 nm and the SYBR Gold emission is detected through a 537 nm filter. Both pairs of digital images of the EuMac-labeled DNA containing gels and control gels where no nucleic acid has been applied are acquired with the Retiga-1350 EX camera. The intensity of each emission band or area is measured with Fovea PhotoShop plug-in where "feature region" is available. The integrated optical density (IOD), which is the integral of the linear measurements and thus is a measurement of the total luminescence and autofluorescence emission is calculated. The ratios of the emissions from the individual bands in the EuMac and SYBR Gold gels are determined. The protocol with the highest ratio that produces a DNA that is still capable of specific hybridization is selected.

Example XXXV

Validation of Comparative Genomic Hybridization Techniques (a) Two types of hybridizations experiments are performed. The first set of experiments is intended to determine if the different labels affect the degree of DNA hybridization. For these measurements, two DNA specimens are compared. These specimens could be male and female DNA specimens or malignant and normal DNA specimens or other similar pairs. Each of the two specimens is split into four aliquots. For two of the aliquots, each DNA specimen is labeled with a different one of the LnMacs. For the other two aliquots, each DNA specimen is labeled withs a different one of the cyanine or other control fluorochrome pair. For instance, the EuMac-labeled male-DNA is co-hybridized with the ThMac-labeled female-DNA and the EuMac-labeled female-DNA is co-hybridized with the TbMac-labeled male-DNA. For these studies, the two ratios of the red and blue emissions obtained from the individual DNA spots should be inversely related and when multiplied together should yield one. The average of the products of these two ratios, obtained from all of the individual DNA spots on the arrays, will be calculated from the results obtained from the pair of co-hybridization experiments performed with the Ln-labeled-DNAs and the pair of co-hybridization experiments performed Cy-labeled-DNAs. Since the LnMacs are virtually chemically identical and are isomorphous, their ratio is found to be closer to one.

(b) The second set of experiments is intended to detect selective binding of labels to specific DNA sequences. This again involves DNA samples that have been labeled with both LnMacs and both cyanine dyes. However, only one of the DNA samples is used for this series. For instance, two Ln-labeled female DNA samples are co-hybridized and the two Cy-labeled female DNA samples are co-hybridized. For these studies, the ratios of the red to the blue emissions obtained from the individual spots should be identical for each co-hybridization experiment. The standard deviation of the ratios from all of the DNA spots is an indication of selective binding to specific gene sequences and the effects of background fluorescence. The standard deviation of the LnMac-labels is found to be lower than that of the Cy-labels.

(c) These experiments are repeated with the substitution of a flashlamp or other lightsource for the standard (Hg and/or Xe) short arc lamp. If PDCA or other energy transfer donor with a similar excitation different from 350-370 nm is employed, the light source must be capable of producing pulsed light in the region of the excitation maximum. In the case of PCDA, 280 nm light must be provided by the flashlamp and the camera must be capable of time-gating and summing the images produced by multiple flashes.

Example XXXVI

Simultaneous Use of Lanthanide Labels as Secondary Reagents for Comparative Genomic Hybridization Measurements In this Example, methods of this invention to analyze genomes by Comparative Genomic Hybridization (CGH) are exemplified by employing two luminescent species, each attached to a secondary reagent. This procedure is based on U.S. Pat. No. 5,976,790. Pinkel et al (Ref. 41) and Kallioniemi et al. (Ref. 46), which describe the following steps for CGH:
1. Removal of Repetitive Sequences and/or Disabling the Hybridization Capacity of Repetitive Sequences.
2. Labeling the Nucleic Acid Fragments of the Subject Nucleic Acids.
3. In Situ Hybridization.

Pinkel et al. 1999 (Ref. 41) summarize In Situ Hybridization as: "Generally in situ hybridization comprises the following major steps: (1) fixation of tissue or biological structure to be examined, (2) prehybridization treatment of the biological structure to increase accessibility of target DNA, and to reduce nonspecific binding, (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments."

These Authors state that their present technique is limited: "At the current stage of development of CGH, sensitivity is primarily limited by the granularity of the hybridization signals in the metaphase chromosomes. Further improvements in sensitivity will be achieved by optimization of the probe concentration and labeling, and by the averaging of the green-to-red fluorescence ratios from several metaphase spreads." An indirect labeling procedure is described below.

A. Materials
  (a) The SmMac-Streptavidin Conjugate, prepared according to EXAMPLE XXVII.
  (a) The ThMac-Streptavidin Conjugate, prepared according to EXAMPLE VIII with the substitution of the ThMac-mono-NCS for the EuMac-mono-NCS.
  (b) The EuMac-anti-digoxigenin, prepared by the procedures described in EXAMPLE XVI with the replacement of the anti-5-BrdU by anti-digoxigenin (SIGMA #D 8156).
  (c) DAPI of the Most Commonly Used Materials.
  (d) DAPI solution, 10 μM DAPI solution in TBS-Azide, pH 7.4.
  (e) The Gd Rinse Buffer of EXAMPLE XIX.
  (f) The $Gd(TTFA)_3$-EtOH of EXAMPLE V.
  (g) The Clearium Mounting Medium of the Most Commonly Used Materials.
  (h) CytoVision (Applied Imaging, San Jose, Calif.).
  (i) All other materials are as described in U.S. Pat. No. 5,976,790.

B. Procedure
  (a) Steps a through h of the procedures of EXAMPLE XX of U.S. Pat. No. 6,340,744 are followed with the substitution of SmMac-Streptavidin for SmMac-Avidin.

(b) The chromosomes are incubated with 50 μL of the 10 μM DAPI solution for 5 min.
(c) The DAPI stained chromosomes are rinsed with TBS-Azide three times.
(d) The chromosomes are then rinsed twice with 50 μL ethanol and air dried.
(e) Two drops of Gd(TTFA)$_3$-EtOH are applied and allowed to dry.
(f) The slides are rinsed twice with ethanol, removing excess liquid each time.
(g) Thirty μL Clearium Mounting Medium is pipetted onto the chromosome and cell area, making sure all of the chromosomes and cells are covered.
(h) The solvent is removed from the Clearium by mild heat generated with a heat gun.
(i) The chromosomes and cells are observed with a Cyto-Vision or similar arc illuminated automated fluorescence microscope under 365 nm excitation provided by continuous illumination with a 100 watt mercury-xenon arc. The light passes through a UV DAPI cube, which does not include an emission filter. Three removable band-pass emission filters, each of which is blocking for the other two, are located above the cube. The transmission of the first filter is centered at 619 nm and the bandwidth is approximately 10 nm at half maximum. The transmission of the second filter has half maximum cut-off points at 635 and 660 nm, and thus includes as much of the SmMac emission as possible while blocking the radiation emitted by the EuMac and all radiation below 635 nm. The third filter is a standard DAPI 450 nm emission filter (Omega 450DF65).
(j) Alternatively, one set of images is obtained with each of the 3 emission filters. All images are obtained with the flashlamp flashed at approximately 40 pulses per second. The EuMac and SmMac images are obtained after a total delay of approximately 30 μsec. The DAPI images are obtained without any delay. Two sets of control (camera noise) images with the emission totally blocked are obtained. One set is obtained without any delay and the other with the same delay as that employed for the lanthanide macrocycles.
(k) The images obtained from each set of multiple individual flashes are summed, analyzed, corrected for the camera noise background and the spatial nonuniformity of the excitation light on the slide, and converted to a format, such as JPEG 2000, which is suitable for display with conventional computer software.
(l) The ratio of the corrected summed values of the pixels from the SmMac and EuMac images is calculated and then analyzed as described by Pinkel et al. 1999 (Ref. 41).
(m) Alternatively, the procedures described above can be modified by to produce hybrids with arrays consisting of DNA oligomers, such as those described in EXAMPLE XXXIII.
(n) Alternatively, the procedures described above can be modified by replacing the SmMac-Streptavidin conjugate with the ThMac-Streptavidin and the emission filter for the SmMac by the emission filter for the ThMac and ultraviolet excitation optics of EXAMPLE XV and the methanolic solutions of EXAMPLE XIII, which are optimized employing the procedures of EXAMPLE XIV.
(o) Alternatively, the hybridizations could be validated by the procedures of EXAMPLE XXXV.
(p) The procedures employing the optimum formulation of the unitary luminescence enhancing solution with the optimum pair of energy transfer acceptor lanthanide(III) ions results in chromosome preparations with minimal background and higher signal to noise ratios compared to preparations with conventional fluorochromes and if analyzed by the procedures of EXAMPLE XXXV are found to be superior to the preparations with conventional fluorochromes.
(q) The procedure described in this example has the further advantage of simplifying the instrumentation by requiring only one excitation system, which by providing the same intensity and pattern of illumination to the sample and reference specimens increases the accuracy of ratiometric measurements, and a single dichroic mirror for three measurements. In addition, the narrow bandwidths of the emissions from both lanthanides minimize spectral overlap with each other and with the DNA stain DAPI, as well as with other fluorophores. This simplification will result in both less costly instrumentation and improved accuracy in the quantitation of the DNA probes.

Example XXXVII

Simultaneous Use of Lanthanide Labeled DNA for Comparative Genomic Hybridization A. Materials
(a) The EuMac-5-deoxyuridine (Formula VIII) of EXAMPLE XXI of U.S. Pat. No. 6,340,744.
(b) The SmMac-5-deoxyuridine of EXAMPLE XXI of U.S. Pat. No. 6,340,744 or the ThMac-5-deoxyuridine of EXAMPLE XXXIV.
(c) 50 mmol (6 g) of TRIS of the Most Commonly Used Materials and 1 g of Tergitol, obtained from Sigma-Aldrich, St. Louis, Mo., Product No. NP-40, are added to 1 L of water and the solution is adjusted to pH 8.0 with hydrochloric acid (TRIS-NP40, pH 8.0).
(d) The Gd Rinse Buffer of EXAMPLE XIX.
(e) The Gd(TTFA)$_3$-EtOH of EXAMPLE V.

B. Procedure
The procedure of Bastian et al. (Ref. 47), as described in EXAMPLE XXII of U.S. Pat. No. 6,340,744, is followed.
(a) The procedures of U.S. Pat. No. 6,340,744, EXAMPLE XXII, Step 1. DNA Isolation (a through d) are followed.
(b) The procedures of U.S. Pat. No. 6,340,744, EXAMPLE XXII, Step 2. Comparative Genomic Hybridization (a through d) are followed.
(c) The procedures of EXAMPLE XXXVI, Steps c through k, are followed.
(d) Hybridization quality is evaluated by the signal strength, the smoothness of the signal distribution along the chromosome, the lack of accentuated banding, the efficient blocking of the centromeres, and the absence of artifactual ratio variations. Hybridizations in which a concurrent gain of chromosomes 1 p, 19, and 22 is present are considered artifact prone and are not included in the analysis.

The procedures for preparing and hybridizing DNA in EXAMPLE XXXIII and EXAMPLE XXXIV and those described above can also be applied to fluorescence in situ hybridization and chromosome painting. The EuMac and SmMac labels can be excited simultaneously with DAPI and thus can replace two of the five fluorophores employed by U.S. Pat. No. 6,007,994 (1999) (Ref. 39) included by reference to combinatorially labeled oligonucleotide probes. These labeled oligonucleotide probes provide sufficient combinations to permit the visualization and simultaneous identification of all 22 autosomal human chromosomes and the human X and Y chromosomes, or defined sub-regions thereof. Such specific labeling of entire chromosomes or defined sub-regions thereof is referred to as "painting." These nucleic acid probes can also be employed for combinatorial labeling of bacteria, viruses and/or lower eukaryotes that may be present in a clinical or non-clinical preparation. Ward et al. (1999) (Ref. 39) is included by reference. Chapter 8 of Hemmila et al. (1994) (Ref. 37), which describes the use of other rare-earth complexes for similar purposes, is also included by reference.

(e) Alternatively the procedures described above can be modified by to produce hybrids with arrays consisting of DNA oligomers, such as those described in EXAMPLE XXXIII.

(f) Alternatively, the procedures described above can be modified by replacing the SmMac labeled DNA with ThMac labeled DNA and the emission filter for the SmMac by the emission filter for the TbMac and ultraviolet excitation optics of EXAMPLE XV and the unitary luminescence enhancing methanolic solutions of EXAMPLE XIII, which are optimized employing the procedures of EXAMPLE XIV.

(g) Alternatively, the hybridizations could be validated by the procedures of EXAMPLE XXXV.

(h) The procedures employing the optimum formulation of the unitary luminescence enhancing solution with the optimum pair of energy transfer acceptor lanthanide(III) ions results in chromosome preparations with minimal background and higher signal to noise ratios compared to preparations with conventional fluorochromes and if analyzed by the procedures of EXAMPLE XXXV are found to be superior to the preparations with conventional fluorochromes.

(i) The procedure described in this example has the further advantage of simplifying the instrumentation by requiring only one excitation system, which by providing the same intensity and pattern of illumination to the sample and reference specimens increases the accuracy of ratiometric measurements, and a single dichroic mirror for three measurements. In addition, the narrow bandwidths of the emissions from both lanthanides minimize spectral overlap with each other and with the DNA stain DAPI, as well as with other fluorophores. This simplification will result in both less costly instrumentation and improved accuracy in the quantitation of the DNA probes Example XXXVIII Simultaneous Use of Lanthanide Labeled DNA for Comparative Genomic Hybridization on Nucleic Acid Arrays A general description of the procedures for comparative genomic hybridization was given in EXAMPLE XXXIX. The procedures described below are exemplary. Alternatively, the referenced CGH procedures of EXAMPLE XIII can be followed.

A. Materials (a) The EuMac-5-deoxyuridine triphosphate (EuMac-d-UTP) (Formula V) of EXAMPLE XXI of U.S. Pat. No. 6,340,744.

(b) The SmMac-5-deoxyuridine triphosphate (SmMac-d-UTP) of EXAMPLE XXI of U.S. Pat. No. 6,340,744.

(c) The procedure of EXAMPLE XXI of U.S. Pat. No. 6,340,744 is repeated with the replacement of the europium(III) by terbium(III) to produce ThMac-5-deoxyuridine triphosphate (TbMac-d-UTP).

(d) The Gd Rinse Buffer of EXAMPLE XIX.

(e) The Gd(TTFA)$_3$-EtOH of EXAMPLE V.

(f) 1 Mb Human BAC Arrays with 2,632 BAC clones spotted on the array (Genome-Chip™ V1.2, Spectral Genomics, Houston, Tex.).

(g) One male and one female preparation of the human LnMac-labeled-cDNA of EXAMPLE XXXIV. Each of these preparations consists of two aliquots. One aliquot is labeled with the EuMac and the other is labeled with the ThMac. These will be referred to as LnMac-labeled-DNA(s).

(h) Sonicator with microcup horn: Ultra-sonic processor model (Sonics & Materials, Inc., Newtown, Conn., model VC-130).

(i) Human Genomic DNA (Promega, Madison Wis., Female Catalog No.G1521; Male Catalog No. G1471).

(j) DNA Clean and Concentrator™-5 (Zymo Research, Orange, Calif., Catalog No. D4005).

(k) BioPrime DNA Labeling Kit (Invitrogen, Carlsbad, Calif., Catalog No. 18094-011).

(l) Cy3-dCTP & Cy5-dCTP (Perkin Elmer Catalog No. NEL 576-577).

(m) 0.5 M EDTA, pH 8.0.

(n) 5.0M NaCl.

(o) Isopropanol.

(p) 70% Ethanol.

(q) The Clearium Mounting Medium of the Most Commonly Used Materials.

(r) Spectral Hybridization Buffer I (Spectral Genomics, Catalog No. KTHB1-1000H).

(s) Spectral HYB Buffer II (Spectral Genomics, Catalog No. KTHB2-1000H).

(t) Spectral Labeling Buffer (Spectral Genomics, Catalog No. KTLBRP-1000H).

(u) Sterile DNase/RNase-free water (Spectral Genomics, Catalog No. KTSWH-1000H).

(v) 2×SSC is an aqueous solution that contains per liter: 0.3 mol NaCl and 0.03 mol sodium citrate.

(w) Sodium dodecyl sulfate (SDS) (Sigma, Catalog No. L4390).

(x) 2×SSC-0.5% SDS is 2×SSC with the addition of 5.0 g/L of SDS.

(y) Formamide, Molecular Biology Grade (Calbiochem, San Diego, Calif., Catalog No. 344206).

(z) Filter paper Whatrnan 1001 (Fisher Scientific, Catalog No. 09-805-1A).

(aa) Rexyn I-300 Mixed bed, ion exchange resin (Fisher Scientific, Catalog No. R208-500).

(ab) 2×SSC-50% deionized formamide is a one-to-one mixture of 2×SSC and deionized formamide. The formamide is deionized by the addition of 1 g of mixed-bed, ion exchange resin for every 10 ml of formamide, and stirring for 30 to 60 min at room temperature. The resin is then removed by filtration through Whatman No. 1001 filter paper, dispensed into units of use, and stored at −20° C.

(ac) Igepal (CA-630), octylphenyl-polyethylene glycol (Sigma, Catalog No. I8896).

(ad) 2×SSC-0.1% Igepal (CA-630) is 2×SSC with the addition of 1 g/L of Igepal.

(ae) 22×60 mm cover slip.

(af) Heat Block: Digital Dry-Bath Incubator (Fisher Scientific, Fisher Isotemp* Catalog No. 125D).

(ag) Kapak* Fuji Impulse* FS-315 Shop Sealer (Fisher Scientific, Catalog No. 01-812-71, Kapak Corporation Catalog No.:FS315).

(ah) Doubly Distilled Water.

(ai) Rocking Platform Incubator: Shake 'N' Bake Hybridization Oven (Boekel Scientific, Feasterville, Pa., Model 136400).
(aj) GenoSensor Reader System (Vysis, Downers Grove, Ill., model No. 30-145200.
(ak) Tank of high purity nitrogen gas.
(al) 1.5 ml Eppendorf tubes with locking caps.
(am) SpectralWare™ BAC Array Analysis Software (Spectral Genomics).
(an) Hybridization Chamber (Corning Costar, No.:2551; Fisher Scientific, Catalog No. 07-200-271).
(ao) Kapak Heat-Sealable Pouch (Fisher Scientific, 01-812-25A).

B. Procedure (a) The human male and female DNA samples prepared in step (d) of the procedures of EXAMPLE XXXIV are labeled with Cy3 and Cy5 by the procedures described in Step 2: Differentially label DNA with Cy3-dCTP and Cy5-dCTP (Ref. 57). These will be referred to as Cy-labeled-DNA(s).
(b) The LnMac-labeled-DNA and Cy-labeled DNA samples are tested by agarose gel electrophoresis as described in Ref. 57; and the size of the majority of the labeled DNA fragments prior to denaturation is found to be in the range of 100-500 base pairs.
(c) Enzymatic activity is stopped by the addition of 0.5 M EDTA, pH 8.0 and heating at 72° C. for 10 min (Ref. 57).
(d) The samples are cooled on ice to before proceeding with hybridization, or stored at −20° C. until required (Ref. 57).
(e) One or more pairs DNA samples, where one member of the pair is labeled with a first LnMac and the other labeled with a second LnMac, are mixed. This can be accompanied by one or more control experiments where a pair of DNA samples, one of which is labeled with a first cyanine dye and the other is labeled with a second cyanine dye, are mixed. For the purposes of clarity, the description of the rest of the process of comparative genetic hybridization will be limited to one pair of LnMac-labeled-DNA samples. The DNA preparation procedures of Ref. 57 are followed. For this description the volume of each of the labeled DNA samples will be 110 μL. All Spectral Hybridization Buffers are stored at −20° C. until needed. The DNA is precipitated by the sequential addition of 45 μL of Spectral Hybridization Buffer I, 12.9 μL of 5.0 M NaCL, and 130 μL of isopropanol. The contents are mixed at each step with a vortex mixer. The mixture is briefly centrifuged and incubated in the dark at room temperature for 20 min. The supernatant is carefully removed from the DNA after centrifugation at greater than 10,000 g for 20 min. For the LnMacs, the precipitate is visually inspected under ultraviolet light. Visible light is sufficient for cyanine dyes. The pellets are rinsed by the addition of 500 μL of 70% ethanol followed by centrifugation and subsequent removal of as much of the supernatant as possible. The pellets are air-dried for 10 min in the dark at room temperature and can be stored at 20° C.
(f) The DNA hybridization procedures of Ref. 57 are followed. The sample is first prepared for denaturation, as follows. Sterile DNase/RNase-free water (10 μL) is added to the DNA pellets, followed by a 10 sec centrifugation to collect the sample, incubation for 10 min in the dark at room temperature, checking that the sample has been suspended, addition of 30 μL of Spectral Hybridization Buffer II, and mixing the sample well by pipetting. The DNA is then denatured to single strands by incubation in a heat block at 72° C. for to min. This is immediately followed by cooling in an ice-water slurry for 5 min, to prevent renaturation. The sample is re-collected by a brief centrifugation and then incubated a 37° C. for 30 min. The sample is pipetted as a line of liquid down the center of the Human BAC Array slide, which has been previously kept desiccated at room temperature. The sample is spread and protected by the application of a 22×60 mm cover-slip, avoiding the formation of air bubbles. The slide is then placed in a hybridization chamber, which is kept hydrated by the addition of 10 μL of water to the wells located on both sides of each chamber. The slides are kept horizontal for the rest of the hybridization procedure. The chamber is closed and protected from light by wrapping with aluminum foil. The wrapped chamber, together with a wet paper towel which serves to prevent evaporation, is placed in a Kapak Pouch, which is then heat sealed. The pouch is then incubated at 37° C. for 16 hours.
(g) The Post-hybridization wash procedures of Ref. 57 are followed. 1) The 2×SSC-50% deionized Formamide, 2×SSC-0.1% Igepal (CA-630), and 0.2×SSC solutions are heated to 50° C. 2) The Kapak Pouch is opened and the chamber is removed and opened. 3) The slide with its cover-slip is inserted in a Petri dish, covered with 2×SSC-0.5% SDS, and the cover-slip is gently removed. The Petri dish is then inserted into a rocking platform incubator, and the slide is rocked and washed for approximately 5 sec. 4) The slide is transferred using a pair of forceps to a fresh Petri dish, which contains 2×SSC-50% Formamide prewarmed to 50° C. The slide containing Petri dish is then incubated and rocked in a rocking platform incubator for 20 min. 5) The slide is transferred using a pair of forceps to a fresh Petri dish, which contains 2×SSC-0.1% Igepal prewarmed to 50° C. The slide containing the Petri dish is then incubated and rocked in a rocking platform incubator for 20 min. 6) The slide is transferred using a pair of forceps to a fresh Petri dish, which contains 2×SSC that had been prewarmed to 50° C. The slide containing Petri dish is then incubated and rocked in a rocking platform incubator for 20 min. 7) The slide is washed twice at room temperature with doubly distilled water. For each wash, the slide is transferred using a pair of forceps to a fresh Petri dish and then incubated and rocked in a rocking platform incubator for 5 sec. 7) The slide is then immediately blow dried with a stream of nitrogen gas. It can then be protected from light by storage in a desiccator that is protected from light.
(h) In the case of arrays to which Ln-labeled-DNA is bound, the procedures of EXAMPLE XIV are followed.
(i) Alternatively, the procedures of van Zyl, US Application 20040175717, (Ref. 37) are followed with the substitution of the Ln-labeled-DNAs for the dUTP-Cy3™-labeled-DNA and dUTP-Cy5™-labeled-DNA.
(j) Thirty μL Clearium Mounting Medium is pipetted onto the array areas, making sure that each array on the slide is completely covered.
(k) The solvent is removed from the Clearium by mild heat generated with a heat gun.
(l) In the case of TTFA containing unitary solutions, the arrays are analyzed with the GenoSensor Reader System or similar arc illuminated system. The excitation filter and dichroic mirror employed in analyzing DAPI stained samples is used with the emission filters of EXAMPLE XXXVI.

(m) In the case of PCDA containing unitary solutions, the arrays are analyzed with the GenoSensor Reader System or similar arc illuminated system which includes the modifications of EXAMPLE XV and the Eu(III) emission filter of EXAMPLE XXVI.

(n) In the case of Cy-labeled-DNAs, the manufacturer's filter settings are employed.

(o) The emissions of the individual spots on the arrays are measured and analyzed following the manufacturer's instructions and with the use of the manufacturer's software.

(p) Alternatively, The hybridizations could be validated by the procedures of EXAMPLE XXXV.

(q) Alternatively, if the time-gated system of EXAMPLE XX is employed with if necessary the procedures of EXAMPLE XV, the removal of the background emission from the preparation including the microscope slide produces superior results for the Ln-labeled-DNAs to those produced by the arc lamp. The contaminating signal produced by the Cy-labeled-DNAs or DAPI is minimal. The procedures of EXAMPLE XXXV are followed. The luminescence ratios obtained from cohybridization experiments with pairs of DNA preparations from a male and a female or a tumor and control normal tissue from the same patient in which the members of each pair of DNA preparations were labeled of with each of two LnMacs result in two ratios of luminescence emissions from the two LnMacs from the individual DNA spots. The first ratio is obtained when first member of the pair is labeled with a first LnMac and the second member of the pair is labeled with the second LnMac. The second ratio is obtained when the first member of the pair is labeled with a second LnMac and the second member of the pair is labeled with the first LnMac. The first ratio is inversely related to the second ratio and when the first and second ratios are multiplied together the result is very close to one. This is establishes that the luminescence ratios are a true measurement of the ratio of hybridization.

(r) The procedures employing the optimum formulation of the unitary luminescence enhancing solution with the optimum pair of energy transfer acceptor lanthanide(III) ions results in arrays where the individual samples (spots) have minimal background and higher signal to noise ratios compared to preparations with conventional fluorochromes and if analyzed by the procedures of EXAMPLE XXXV are found to be superior to the preparations with conventional fluorochromes.

(s) The procedure described in this example has the further advantage of simplifying the instrumentation by requiring only one excitation system, which by providing the same intensity and pattern of illumination to the sample and reference specimens increases the accuracy of ratiometric measurements, and a single dichroic mirror for three measurements. In addition, the narrow bandwidths of the emissions from both lanthanides minimize spectral overlap with each other and with the DNA stain DAPI, as well as with other fluorophores. This simplification will result in both less costly instrumentation and improved accuracy in the quantitation of the DNA probes.

Example XXXIX

Two Photon Excitation of the EuMac Labelled Cells Dried from a Gadolinium(TTFA)$_3$ Solution A. Materials (a) A standard glass microscope slide with EuMac-di-NCS labelled cells prepared according to the procedures of EXAMPLE XIX. A very thin layer of Clearium was allowed to dry.

B. Procedure (a) The slides were examined with a laser scanning LSM510 NLO/Combi system Zeiss confocal microscope equipped with a Coherent Mira Ti-sapphire laser and a C-Apochromat 40×1.2 N.A. water-corrected objective. The excitation was at 800 nm, and the emission between 510 and 685 nm was detected. Each pixel was 0.15 by 0.15 nm and the scanning dimensions were both 76.8 nm. A 90 µm pinhole, which corresponds to one airy unit (about 1.1 µm full width at half-maximum for no zoom) was used. The laser pulse width was 100 fs and the pulse rate was 76 mhz (every 12 ns), which should produce about 500 pulses in 6.4 microsecond dwell time on the pixel. Each line was scanned four times and the result averaged. The optical zoom was 3. The image was displayed with the Zeiss LSM5 image browser and copied into Adobe Photoshop were it was transformed into grayscale and inverted.

(b) In spite of the minimal integration time, the image shown in FIG. 18 has minimal background indicating that signal to noise was excellent. Thus, it is possible to use lanthanide labels with emission enhancement by a second lanthanide for two photon laser scanning confocal microscopy. Since the long wavelengths used for excitation are minimally scattered by biological materials, the detection of analyte-binding species located significantly below the surface of the material will be possible, particularly when red or near infrared emitting lanthanides are used. Thus, two photon excitation can be applied to the examples of this patent.

REFERENCES

1. L. M. Vallarino and R. C. Leif, U.S. Pat. No. 5,373,093, "Macrocycle complexes of Yttrium, the Lanthanides and the Actinides having Peripheral Coupling Functionalities", 1994.
2. L. M. Vallarino and R. C. Leif, U.S. Pat. No. 5,696,240, "complexes of Yttrium, the Lanthanides and the Actinides having Peripheral Coupling Functionalities Continuation-In-Part", 1997.
3. R. C. Leif, P. M. Harlow, and L. M. Vallarino, "Production, Fixation, and Staining of Cells on Slides for Maximum Photometric Sensitivity". Proceedings of Biochemical Diagnostic Instrumentation, Progress in Biomedical Optics. R. F. Bonner, G. E. Cohn, T. M. Laue, and A. V. Priezzhev Eds.; SPIE Proceedings Series 2136, pp. 255-262 (1994).
4. N. Sabbatini, L. De Cola, L. M. Vallarino, and G. Blasse, "Radiative and Nonradiative Transitions in the Eu(III) Hexaaza Macrocyclic Complex [Eu($C_{22}H_{26}N_6$)($CH_3COO$)]($CH_3COO$)Cl 2$H_2O$," *J. Phys. Chem.*, Vol. 91, pp. 4681-4685, 987.
5. R. C. Leif and L. M. Vallarino, U.S. Pat. No. 6,340,744, "A Reagent System and Method for Increasing the Luminescence of Lanthanide(III) Macrocyclic Complexes", 2002 and United States Patent Application 20020132992, Sep. 19, 2002.
6. R. C. Leif. and L. M. Vallarino. U.S. Pat. No. 6,750,005, "A Reagent System and Method for Increasing the Luminescence of Lanthanide(III) Macrocyclic Complexes", (2004).
7. Y-Y Xu and I. A. Hemmila, "Co-fluorescence enhancement system based on pivaloyltrifluoroacetone and yttrium for the simultaneous detection of europium, terbium, samarium and ysprosium", Analytica Chimica Acta, Vol. 256 pp. 9-16 (1992).

8. C. Tong, Y. Zhub, and W. Liua, "Study on the co-luminescence system of Dy—Gd-1,6-bis(1'phenyl-3'-methyl-5'-pyrazol-4'-one)hexanedione-cetyltrimethylammonium bromide and its analytical application", Analyst, Vol. 126, pp. 1168-1171 (2001).

9. Y. Yang, Q. Su, and G. Zhao, "Photoacoustic study of the co-fluorescence effect of lanthanide ternary complexes in solid states", Journal of Molecular Structure, Vol. 525 pp. 47-52 (2000).

10. G. Blasse, G. J. Dirksen, N. Sabbatini, S. Perathoner, J. M. Lehn, B. Alpha, "Luminescence properties in [Tb_bpy.b-py.bpy]3. cryptate: a low-temperature solid-state study", J. Phys. Chem. Vol. 92, pp. 2419-2422. (1998).

11. A. J. Bromm Jr., R. C. Leif, J. R. Quagliano, and L. M. Vallarino, "The Addition of a Second Lanthanide Ion to Increase the Luminescence of Europium(III) Macrocyclic Complexes", Proceedings of Optical Diagnostics of Living Cells II, D. L. Farkas, R. C. Leif, B. J. Tromberg, Editors, SPIE Progress in Biomedical Optics,. A. Katzir series Editor, Vol. 3604, ISBN 0-8194-3074-9, pp. 263-272, 1999.

12. J. R. Quagliano, R. C. Leif, L. M. Vallarino, and S. A. Williams, "Methods to Increase the Luminescence of Lanthanide(III) Macrocyclic Complexes", Optical Diagnostics of Living Cells III, D. L. Farkas and R. C. Leif, Editors, Proceedings of SPIE Vol. 3921. pp. 124-133, 2000.

13. R. C. Leif, M. C. Becker, L. M. Vallarino J. W. Williams, and S. Yang, "Progress in the Use of Quantum Dye® Eu(III)-Macrocycles", in Manipulation and Analysis of Biomolecules, Cells and Tissues, D. V. Nicolau, J. Enderlein, and R. C. Leif Editors, SPIE Proceedings Vol. 4962, pp. 341-353 (2003).

14 R. C. Leif, M. C. Becker, A. Bromm Jr., N. Chen, A. E. Cowan, L. M. Vallarino, S. Yang, and R. M. Zucker, Lanthanide Enhanced Luminescence (LEL) with one and two photon excitation of Quantum Dyes® Lanthanide(III)-Macrocycles, in Manipulation and Analysis of Biomolecules, Cells, and Tissues, D. V. Nicolau, J. Enderlein, R. C. Leif, and D. Farkas, Editors, SPIE Proceedings Vol. 5322 pp. 187-199(2004).

15. R. C. Leif and L. M. Vallarino, PCT WO 01/27625 A1 (PCT/US00/27787), "Conjugated Polymer Tag Complexes", 2001.

16. R. C. Leif, M. C. Becker, A. J. Bromm Jr., L. M. Vallarino, S. A. Williams, and S. Yang, "Increasing the Luminescence of Lanthanide(III) Macrocyclic Complexes by the Use of Polymers and Lanthanide Enhanced Luminescence", Optical Diagnostics of Living Cells IV, D. L. Farkas and R. C. Leif, Editors, SPIE BIOS Proceeding Volume 4260 pp. 184-197 (2001).

17. X. Xiao, M. E. Herring, J. Haushalter, S. Lee, K. S. Kalogerakis, and G. W. Faris, "Optical Property Measurements of A Novel Type of Upconverting Reporter," in Genetically Engineered and Optical Probes for Biomedical Applications, A. P. Savitsky, D. J. Bornhop, R. Raghavachari, and S. I. Achilefu Editors, Proceedings of SPIE Vol. 4967 pp. 172-178 (2003).

18. D. A. Zarling, M. Rossi, N. A. Peppers, J. Kane, G. W. Faris, M. J. Dyer, S. Y. Ng, and L. V. Schneider, U.S. Pat. No. 5,698,397, "Up-Converting Reporters for Biological and Other Assays Using Laser Excitation Techniques", 1997.

19. K. W. Kardos, R. S. Niedbala, J. L. Burton, D. E. Cooper, D. A. Zarling, M. Rossi, N. A. Peppers, J. Kane, G. W. Faris, M. J. Dyer, S. Y. Ng, and L. V. Schneider, U.S. Pat. No. 6,159,686, "Up-Converting Reporters for Biological and Other Assays Using Laser Excitation Techniques", 2000.

20. K. N. Raymond, S. Petoud, S. M. Cohen, J. Xu, U.S. Pat. No. 6,515,113, "Phthalamide lanthanide complexes for use as luminescent markers", 2003.

21. K. N. Raymond, S. Petoud, S. M. Cohen, J. Xu, U.S. Pat. No. 6,406,297, "Salicylamide-lanthanide complexes for use as luminescent markers", 2002.

22. Y. Murthy and R. H. Suva, US Application 20,040,082, 768, "Metal chelates and methods of using them for time-resolved fluorescence", 2004.

23. G. Jones, II and D. Yan, U.S. Pat. No. 6,402,986, "Compositions and methods for luminescence lifetime comparison", 2002.

24. G. Mathis, J-M Lehn, U.S. Pat. No. 4,927,923, "Macropolycyclic rare earth complexes and application as fluorescent tracers", 1990.

25. J-M Lehn, G. Mathis, B. Alpha, R. Deschenaux, E. Jolu, U.S. Pat. No. 5,162,508, "Rare earth cryptates, processes for their preparation, synthesis intermediates and application as fluorescent tracers", 1992.

26. J-M Lehn, G. Mathis, B. Alpha, R. Deschenaux, E. Jolu, U.S. Pat. No. 5,534,622, "Rare earth cryptates, processes for their preparation, synthesis intermediates and application as fluorescent tracers", 1996.

27. J. W. Hofstraat, US Application 20020187563, "Diagnostic Neodymium(III), Ytterbium(III), or Erbium(III) Ion-ligand Complexes" 2002.

28. F. Hausch and A. Jäschke, "Multifunctional dinucleotide analogs for the generation of complex RNA conjugates", Tetrahedron 57 pp. 1261-1268. (2001).

29. Q. Yang, S. He, and L. Li, (Abstract) "NMR Study of the Complexes of Eu(La) with Pyridine-2,6-Dicarboxylic acid," Hebei Shifan Daxue Xuebao, Ziran Kexueban, 19, pp. 63-66 (1995).

30. A. Kawski, "Excitation Energy Transfer and Its Manifestation in Isotropic Media;" Photochem Photobiol 38, pp. 487 (1983).

31. R. C. Leif, M. C. Becker, A. J. Bromm Jr., L. M. Vallarino, J. W. Williams, S. A. Williams, and S. Yang, "Optimizing the Luminescence of Lanthanide(III) Macrocyclic Complexes for the Detection of anti-5-BrdU", Optical Diagnostics of Living Cells V, D. L. Farkas and R. C. Leif, Editors, SPIE Proceedings Vol. 4622 pp. 250-261 (2002).

32. APO-BRDU Protocol, Phoenix Flow Systems, 6790 Top Gun St., Suite 1, San Diego, Calif. 92121-4121, Tel. (858) 453-5095; http://www.phnxflow.com/.

33. R. C. Leif "Methods for Preparing Sorted Cells as Monolayer Specimens". In Living Color, Protocols in Flow Cytometry and Cell Sorting, Editors. R. A. Diamond and S. DeMaggio, Springer, ISBN 3-540-65149-7, pp. 592-619, 2000.

34. ABSOLUTE-S™ Protocol, Phoenix Flow Systems, 6790 Top Gun St., Suite 1, San Diego, Calif. 92121-4121, Tel. (858) 453-5095; http://www.phnxflow.com/.

35. X. Li, F. Traganos, M. R. Melamed, and Z. Darzynkiewicz, "Detection of 5-bromo-2-deoxyuridine incorporated into DNA by labeling strand breaks induced by photolysis (SBIP)". Int. J. Oncol. Vol. 4 pp. 1157-1161, 1994.

36. E. Benjamini and S. Leskowitz, "Immunology A Short Course (Second Edition) Wiley-Liss, ISBN 0-471-56751-5, PP. 117-119, 1991.

37. I. Hemmila et al. "Bioanalytical applications of labeling technologies, A review of trends and new opportunities in biospecific assay, based on the product offering of Wallac, an EG&G company, Edited by I. Hemmila et al. (1994)

38. D. C. Ward, P. R Langer, and A. A. Waldrop, III, U.S. Pat. No. 5,449,767, "Modified Polynucleotides and Methods of Preparing Same." (1995).
39. D. C. Ward, M. Speicher, S. G. Ballard, and J. T. Wilson, U.S. Pat. No. 6,007,994, "Multi-parametric fluorescence in situ hybridization." (1999).
40. D. Pinkel, D. Albertson, J. W. Gray, U.S. Pat. No. 5,830,645, "Comparative fluorescence hybridization to nucleic acid arrays" (1998).
41. D. Pinkel, J. W. Gray, A. Kallioniemi, O-P. Kallioniemi, F. Waldman, M. Sakamoto, U.S. Pat. No. 5,976,790, "Comparative Genomic Hybridization (CGH)" (1999).
42. J. W. Gray, D. Pinkel, D. Albertson, C. Collins, R. Baldocchi, U.S. Pat. No. 6,465,182, "Comparative fluorescence hybridization to nucleic acid arrays" (2002).
43. D. Pinkel, D. Albertson, J. W. Gray U.S. Pat. No. 6,562,565, "Comparative fluorescence hybridization to nucleic acid arrays." (2003).
44. J. R. Piper, US Patent Application 20030124589, "Imaging microarrays" (2003).
45. L van Zyl, US Application 20040175717, "Methods and kits for labeling and hybridizing cDNA for microarray analysis." (2004).
46. A. Kallioniemi, O-P. Kallioniemi, J. Piper, M. Tanner, T. Stokke, L. Chen, H. S. Smith, D. Pinkel, J. W. Gray§, and F. M. Waldman, "Detection and Mapping of Amplified DNA Sequences in Breast Cancer by Comparative Genomic Hybridization", Proc. Natl. Acad. Sci. USA. 91, pp. 2156-2160 (1994).
47. B. C. Bastian, P. E. LeBoit, H. Hamm, E-B. Brocker, and D. Pinkel, "Chromosomal Gains and Losses in Primary Cutaneous Melanomas Detected by Comparative Genomic Hybridization," Cancer Research 58 pp. 2170-2175 (1998).
48. A. S. Ishkanian, C. A. Malloff, S. K. Watson, R. J deLeeuw, B. Chil, B. P. Coe, A. Snijders, D. G. Albertson, D. Pinkel, M. A. Marra, V. Ling, C. MacAulay, and W. L. Lam, "A tiling resolution DNA microarray with complete coverage of the human genome", Nature Genetics 36 pp. 299-303 (2004).
49. S. DeVries and F. Waldman, "CGH of Direct Labeled Test DNA vs Normal DNA", Laboratory Protocols for the Waldman Lab (http://cc.ucsf.edu/people/waldman/Protocols/directcgh.html) (visited 2004).
50. Jan Dumanski's Research Group, "Molecular Oncology Microarray Protocols" Department of Genetics and Pathology, Rudbeck Laboratory SE-751 85 Uppsala, Sweden (http://puffer.genpat.uu.se/chrom_22_array/protocol.pdf) (visited 2004).
51. T. Tasara, B. Angerer, M. Damond, H. Winter, S. Dorhofer, U. Hübscher, and M. Amacker, "Incorporation of reporter molecule-labeled nucleotides by DNA polymerases. II. High-density labeling of natural DNA," Nucleic Acids Research, 31, pp. 2636-2646 (2003).
52. J. B. Randolph and A. S. Waggoner, "Stability, specificity and fluorescence brightness of multiply-labeled fluorescent DNA probes," Nucleic Acids Research, 25, pp. 2923-2929 (1997).
53. J. DeRisi, "Protocol 14 Indirect Fluorescent Labeling of DNA with Amino-Ally) Dyes," in DNA Microarrays: A Molecular Cloning Manual, edited by David Bowtell and Joseph Sambrook, Cold Spring Harbor Laboratory Press, pp. 187-193 (2002).
54. J. Haralambidis, K. Angus, S. Pownall, L. Duncan, M. Chai, and G. W. Tregear, "The Preparation of Polyamide-Oligonucleotide Probes Containing Multiple Non-radioactive Labels," Nucleic Acids Research 18, pp. 501-505 (1990).
55. R. C. Leif and L. M. Vallarino, PCT WO 01/27625 A1, "Conjugated Polymer Tag Complexes" (2001).
56. G. Giller, T. Tasara, B. Angerer, K. Mühlegger, M. Amacker, and H. Winter, "Incorporation of reporter molecule-labeled nucleotides by DNA polymerases. I. Chemical synthesis of various reporter group-labeled 2'-deoxyribonucleoside-5'-triphosphates," Nucleic Acids Research, 31, pp. 2630-2635 (2003).
57. Anonymous, "Protocol for SpectralChip™ 2600", Spectral Genomics, P/N 36-0001-00 rev 2, Effective Date: Sep. 2, 2004 (2004).
58. A. M. Adeyiga, P. M. Harlow, L. M. Vallarino, and R. C. Leif, "Advances in the Development of Lanthanide Macrocyclic Complexes as Luminescent Bio-Markers". Advanced Techniques in Analytical Cytology, Optical Diagnosis of Living Cells and Biofluids, T. Askura, D. L. Farkas, R. C. Leif, A. V. Priezzhev, and B. J. Tromberg Eds.; A. Katzir Series Editor, Progress Biomedical Optics Series Editor SPIE Proceedings Series, Vol. 2678, pp. 212-220, 1996.
59. R. C. Leif and L. M. Vallarino, "Rare-Earth Chelates as Fluorescent Markers in Cell Separation and Analysis". ACS Symposium Series 464, Cell Separation Science and Technology, D. S. Kompala and P. W. Todd Editors, American Chemical Society, Washington, D.C., pp 41-58, 1991.

The invention claimed is:

1. A luminescence enhancing combination comprising a unitary solution consisting essentially of solvent and a luminescence-enhancing amount of at least one energy transfer donor selected from the group consisting of a fluorophore and a lumiphore; and
a first solid comprising an energy transfer acceptor lanthanide ion complex not bound to said energy transfer donor,
wherein when the solution dries in the presence of the first solid it results in a second solid wherein the luminescence of the energy transfer acceptor lanthanide ion complex is enhanced by light that is absorbed by at least one of said energy transfer donors not bound to the energy transfer acceptor lanthanide ion,
and further wherein the luminescence enhancing solution does not comprise a micellar solution.

2. A unitary luminescence enhancing combination according to claim 1, in which the lumiphore is selected from the group consisting of an organic molecule, metal ion, and metal ion complex.

3. A unitary luminescence enhancing combination according to claim 1, further comprising a surfactant, wherein the concentration of surfactant is less than the critical micellar concentration.

4. A unitary luminescence enhancing combination according to claim 1, wherein the energy transfer donor is a lanthanide complex comprising lanthanide ion that differs from the lanthanide ion in the energy acceptor lanthanide ion complex.

5. A unitary luminescence enhancing combination according to claim 2, in which the metal ion of the donor metal ion complex is a lanthanide ion other than the energy transfer acceptor lanthanide ion.

6. A combination according to claim 1 in which the concentration of the energy transfer donor species is in the range of from $1 \times 10^{-6}$ moles per liter to saturation, preferably from $1 \times 10^{-5}$ moles per liter to $1 \times 10^{-2}$ moles per liter.

7. A method for analysis of an insoluble or insolubilized sample suspected of containing at least one analyte, said method comprising the steps of:
a) contacting the sample with a solution that contains a solvent and an energy transfer acceptor lanthanide ion complex that is conjugated to an analyte-binding species, such that the conjugation to the analyte-binding species can be achieved either directly or indirectly through a bridging molecule, and/or by being a tag of a tagged-polymer-conjugate of said member;
b) incubating the sample with the solution under binding conditions, whereby the member of the specific combining pair binds to the analyte;
c) removing excess members of the specific combining pair;
d) adding to the sample a single-phase, non-micellar luminescence enhancing solution;
e) removing the solvent of the single-phase, non-micellar luminescence enhancing solution to produce a homogeneous solid composition that includes both an energy transfer donor compound and the energy transfer acceptor complex, the energy transfer donor compound not bound to the energy transfer acceptor complex, the solid composition having the characteristic that the energy transfer acceptor complex is enhanced by light absorbed by the unbound energy transfer donor compound;
f) subjecting the homogeneous solid composition to excitation energy in the range of 200-1500 nm, whereby enhanced luminescence in the range of 350-2000 nm is generated;
g) monitoring the luminescence of the homogeneous solid composition for at least one of the following:
1) presence and/or concentration and/or location of the energy transfer acceptor lanthanide ion complex; and
2) presence and/or concentration and/or location of the product of the interaction of the analyte with the energy transfer acceptor lanthanide ion complex which is conjugated to an analyte-binding species.

8. The combination according to claim 1 wherein the fluorophore or lumiphore energy transfer donor compound is an ionic compound of gadolinium (III).

9. The combination according to claim 1 wherein the fluorophore or lumiphore energy transfer donor compound is a complex of gadolinium (III).

10. A combination according to claim 1 in which the lanthanide ion complex has the formula

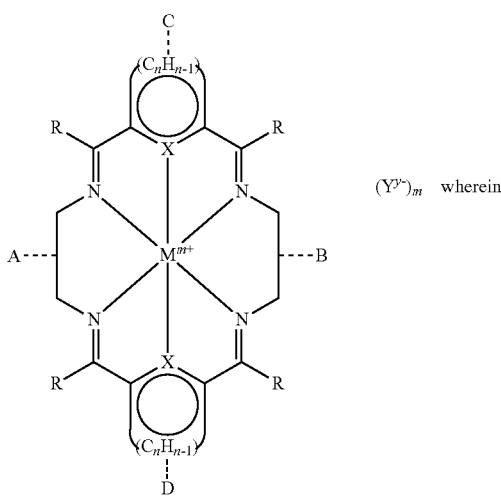

$(Y^{y-})_m$ wherein

M is a metal ion selected from the group consisting of a lanthanide having atomic number 57-71, an actinide having atomic number 89-103 and yttrium (III) having atomic number 39;
R is a substituent selected from the group consisting of hydrogen, straight-chain and branched alkyl, aryl-substituted alkyl, aryl, and alkyl-substituted aryl, with the proviso that such substituent does not limit the solubility of the resultant complex,
X is selected from the group consisting of nitrogen, sulfur and oxygen and forms a part of a ring structure selected from the group consisting of pyridine, thiophene or furan, respectively, at the positions marked X;
n is 2 or 3;
Y is an anion, with the proviso that such anion does not limit the solubility of the resultant complex or otherwise interfere with either the coupling procedure or the energy transfer leading to fluorescence;
m is the ionic charge of the metal ion in the macrocyclic complex;
$y^-$ is the ionic charge of the anion Y in the macrocyclic complex; and
A, B, C, and D are substituents independently selected from the group consisting of hydrogen, straight-chain alkyl, branched-chain alkyl, aryl-substituted alkyl, aryl, alkyl-substituted aryl, reactive functionality, functionalized alkyl, functionalized aryl-substituted alkyl, functionalized aryl, and functionalized alkyl-substituted aryl.

11. A combination according to claim 1 wherein the energy transfer acceptor lanthanide ion complex includes a cryptate.

12. A combination according to claim 1 in which the energy transfer lumiphore is selected from the group consisting of an organic ligand, a salt of an organic ion, a metal ion complex of an organic ligand and mixtures thereof that after excitation emits energy absorbed by the energy transfer acceptor lanthanide ion complex.

13. A combination according to claim 1 in which the energy transfer acceptor lanthanide ion complex is covalently attached to an analyte-binding species.

14. A combination according to claim 1 in which the energy transfer acceptor lanthanide ion complex includes a macrocycle.

15. A method for analysis of a soluble sample suspected of containing at least one analyte, said method comprising the steps of:
a) contacting the sample while in a first solution with a solid support to which is bound a first member of a specific combining pair that binds to said at least one analyte;
b) incubating the sample with the first solution under binding conditions, whereby said at least one analyte binds to said first member of a specific combining pair;
c) removing the first solution if necessary;
d) contacting the sample with a second solution that contains a solvent and an energy transfer acceptor lanthanide ion complex that is conjugated to a second analyte-binding species specific for said at least one analyte, wherein the conjugation of the lanthanide ion complex to the second analyte-binding species is achieved by a method selected from the group consisting of direct or indirect conjugation through a bridging molecule, conjugation by virtue of the lanthanide ion complex being a tag of a tagged-polymer-conjugate of said second analyte-binding species, and combinations thereof, and further wherein said second analyte binding species is a member of a specific binding pair that binds to said at least one analyte;
e) incubating the bound sample with the second solution of the second analyte-binding species under binding conditions, whereby the second analyte-binding species binds to the analyte;
f) removing excess of the second analyte-binding species;
g) adding to the sample a single-phase non-micellar luminescence enhancing solution;
h) removing the solvent of the single-phase, non-micellar luminescence enhancing solution to produce a homogeneous solid composition that includes both an energy transfer donor compound and the bound energy transfer acceptor complex, the energy transfer donor compound not bound to the energy transfer acceptor complex, the solid composition having the characteristic that the energy transfer acceptor complex is enhanced by light absorbed by the unbound energy transfer donor compound;
i) subjecting the homogeneous solid composition to excitation energy in the range of 200-1500 nm, whereby enhanced luminescence in the range of 350-2000 nm is generated;
j) monitoring the luminescence of the homogeneous solid composition for at least one of the following:
   a. presence and/or concentration and/or location of the energy transfer acceptor lanthanide ion complex; and
   b. presence and/or concentration and/or location of the product of the interaction of the analyte with the energy transfer acceptor lanthanide ion complex which is conjugated to an analyte-binding species.

16. A method for analysis of a soluble sample suspected of containing at least one analyte, said method comprising the steps of:
a) contacting a sample which is in a first solution with a second solution that contains a solvent and an energy transfer acceptor lanthanide ion complex that is conjugated to an analyte-binding species, such that the conjugation to the analyte-binding species is achieved directly or indirectly through a bridging molecule or by virtue of being a tag of a tagged-polymer-conjugate of said analyte-binding species, wherein the sample and the analyte-binding species are not identical;
b) incubating the sample with the combined solution under binding conditions, whereby the member of the specific combining pair binds to the analyte;
c) transferring the free and bound sample to a container that contains a solid support to which is attached a second analyte-binding species specific for said analyte, and wherein said second analyte-binding species is a first member of a specific combining pair that binds to said analyte or is an analyte-binding species that is a different member of a specific binding pair that binds to said analyte;
d) incubating the sample bound to the first analyte-binding species with the second analyte-binding species that is bound to the solid support;
e) removing excess first analyte-binding species;
f) adding to the bound sample a single-phase, non-micellar luminescence enhancing solution having the characteristic that after drying it results in a solid that enhances the luminescence of an energy transfer acceptor lanthanide ion complex and comprises unbound energy transfer donor;
g) removing the solvent of the single-phase, non-micellar luminescence enhancing solution to produce a homogeneous solid composition that includes both the energy transfer donor compound and the bound energy transfer acceptor complex, the energy transfer donor compound not bound to the energy transfer acceptor complex, wherein the unbound energy transfer donor is in large excess to the lanthanide ion;
h) subjecting the homogeneous solid composition to excitation energy in the range of 200-1500 nm, whereby enhanced luminescence in the range of 350-2000 nm is generated;
i) monitoring the luminescence of the homogeneous solid composition for at least one of the following:
   a. presence and/or concentration and/or location of the energy transfer acceptor lanthanide ion complex; and
   b. presence and/or concentration and/or location of the product of the interaction of the analyte with the energy transfer acceptor lanthanide ion complex which is conjugated to an analyte-binding species.

* * * * *